(12) United States Patent
Becker et al.

(10) Patent No.: US 10,752,605 B2
(45) Date of Patent: *Aug. 25, 2020

(54) TREPROSTINIL DERIVATIVE COMPOUNDS AND METHODS OF USING SAME

(71) Applicant: CORSAIR PHARMA, INC., South San Francisco, CA (US)

(72) Inventors: Cyrus K. Becker, Fremont, CA (US); Meenakshi S. Venkatraman, Fremont, CA (US); Xiaoming Zhang, Sunnyvale, CA (US)

(73) Assignee: Corsair Pharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,664

(22) Filed: May 21, 2019

(65) Prior Publication Data

US 2019/0292163 A1  Sep. 26, 2019

Related U.S. Application Data

(63) Continuation of application No. 15/686,422, filed on Aug. 25, 2017, now Pat. No. 10,344,012, which is a continuation of application No. 15/157,574, filed on May 18, 2016, now Pat. No. 9,776,982, which is a continuation of application No. 14/153,498, filed on Jan. 13, 2014, now Pat. No. 9,371,264.

(60) Provisional application No. 61/751,608, filed on Jan. 11, 2013.

(51) Int. Cl.
| | |
|---|---|
| C07D 313/00 | (2006.01) |
| C07C 69/712 | (2006.01) |
| C07D 317/40 | (2006.01) |
| C07D 321/00 | (2006.01) |
| C07D 257/06 | (2006.01) |
| C07D 263/24 | (2006.01) |
| C07D 265/30 | (2006.01) |
| C07D 295/088 | (2006.01) |
| C07D 211/60 | (2006.01) |
| C07D 295/145 | (2006.01) |
| C07D 307/20 | (2006.01) |
| C07C 219/16 | (2006.01) |
| C07C 235/20 | (2006.01) |
| C07D 453/02 | (2006.01) |
| C07C 59/54 | (2006.01) |
| C07C 69/734 | (2006.01) |
| C07C 235/34 | (2006.01) |
| C07D 207/08 | (2006.01) |
| C07D 263/26 | (2006.01) |
| C07D 317/34 | (2006.01) |
| A61K 9/70 | (2006.01) |
| A61K 31/165 | (2006.01) |
| A61K 31/216 | (2006.01) |
| A61K 31/335 | (2006.01) |
| C07C 59/31 | (2006.01) |

(52) U.S. Cl.
CPC .......... *C07D 313/00* (2013.01); *A61K 9/7023* (2013.01); *A61K 31/165* (2013.01); *A61K 31/216* (2013.01); *A61K 31/335* (2013.01); *C07C 59/31* (2013.01); *C07C 59/54* (2013.01); *C07C 69/712* (2013.01); *C07C 69/734* (2013.01); *C07C 219/16* (2013.01); *C07C 235/20* (2013.01); *C07C 235/34* (2013.01); *C07D 207/08* (2013.01); *C07D 211/60* (2013.01); *C07D 257/06* (2013.01); *C07D 263/24* (2013.01); *C07D 263/26* (2013.01); *C07D 265/30* (2013.01); *C07D 295/088* (2013.01); *C07D 295/145* (2013.01); *C07D 307/20* (2013.01); *C07D 317/34* (2013.01); *C07D 317/40* (2013.01); *C07D 321/00* (2013.01); *C07D 453/02* (2013.01); *C07C 2601/02* (2017.05); *C07C 2601/14* (2017.05); *C07C 2601/16* (2017.05); *C07C 2602/42* (2017.05); *C07C 2603/14* (2017.05)

(58) Field of Classification Search
CPC .................................................... C07D 313/00
See application file for complete search history.

(56) References Cited

U.S. PATENT DOCUMENTS

| | | |
|---|---|---|
| 3,598,122 A | 8/1971 | Zaffaroni |
| 4,144,317 A | 3/1979 | Higuchi et al. |
| 4,201,211 A | 5/1980 | Chandrasekaran et al. |
| 4,262,003 A | 4/1981 | Urquhart et al. |

(Continued)

FOREIGN PATENT DOCUMENTS

| | | |
|---|---|---|
| EP | 0496548 A1 | 7/1992 |
| EP | 1628654 A2 | 3/2006 |

(Continued)

OTHER PUBLICATIONS

Cochrane et al., "A macrolactonization approach to the total synthesis of the antimicrobial cyclic depsipeptide Li-F04a and diastereosiomeric analogues", Beilstein Journal of Organic Chemistry, vol. 8, 1344-1351 (2012).

(Continued)

*Primary Examiner* — Shawquia Jackson
(74) *Attorney, Agent, or Firm* — The Marbury Law Group, PLLC

(57) ABSTRACT

Compounds represented by formulae I, II, III, and IV including pro-drugs for treprostinil and prostacyclin analogs. Uses include treatment of pulmonary hypertension (PH) or pulmonary arterial hypertension (PAH). The structures of the compounds can be adapted to the particular application for a suitable treatment dosage. Transdermal applications can be used.

19 Claims, No Drawings

(56) References Cited

U.S. PATENT DOCUMENTS

| | | |
|---|---|---|
| 4,306,075 A | 12/1981 | Aristoff |
| 4,306,076 A | 12/1981 | Nelson |
| 4,338,457 A | 7/1982 | Aristoff |
| 4,349,689 A | 9/1982 | Aristoff |
| 4,379,454 A | 4/1983 | Campbell et al. |
| 4,420,632 A | 12/1983 | Aristoff |
| 4,525,586 A | 6/1985 | Aristoff |
| 4,668,814 A | 5/1987 | Aristoff |
| 4,683,330 A | 7/1987 | Aristoff |
| 5,028,628 A | 7/1991 | Tadepalli et al. |
| 5,071,657 A | 12/1991 | Oloff et al. |
| 5,088,977 A | 2/1992 | Sibalis |
| 5,153,222 A | 10/1992 | Tadepalli et al. |
| 5,328,453 A | 7/1994 | Sibalis |
| 5,797,898 A | 8/1998 | Santini, Jr. et al. |
| 5,853,751 A | 12/1998 | Masiz |
| 5,972,974 A | 10/1999 | Keenan |
| 6,242,482 B1 | 6/2001 | Shorr et al. |
| 6,264,990 B1 | 7/2001 | Knepp et al. |
| 6,635,274 B1 | 10/2003 | Masiz et al. |
| 6,638,528 B1 | 10/2003 | Kanios |
| 6,700,025 B2 | 3/2004 | Moriarty et al. |
| 6,809,223 B2 | 10/2004 | Moriarty et al. |
| 7,199,157 B2 | 4/2007 | Wade et al. |
| 7,375,139 B2 | 5/2008 | Aldred |
| 7,384,978 B2 | 6/2008 | Phares et al. |
| 7,417,070 B2 | 8/2008 | Phares et al. |
| 7,537,590 B2 | 5/2009 | Santini, Jr. et al. |
| 7,544,713 B2 | 6/2009 | Phares et al. |
| 8,232,316 B2 | 7/2012 | Phares et al. |
| 8,242,305 B2 | 8/2012 | Batra et al. |
| 8,252,839 B2 | 8/2012 | Phares et al. |
| 8,349,892 B2 | 1/2013 | Phares |
| 8,410,169 B2 | 4/2013 | Phares et al. |
| 8,435,944 B2 | 5/2013 | Dipietro et al. |
| 8,481,782 B2 | 7/2013 | Batra et al. |
| 8,497,393 B2 | 7/2013 | Batra et al. |
| 8,519,178 B2 | 8/2013 | Hogan et al. |
| 8,524,939 B2 | 9/2013 | Wei et al. |
| 8,536,363 B2 | 9/2013 | Phares et al. |
| 8,591,941 B2 | 11/2013 | Kanios et al. |
| 8,609,134 B2 | 12/2013 | Yoneto et al. |
| 8,617,591 B2 | 12/2013 | Schacht et al. |
| 8,658,837 B2 | 2/2014 | Wei et al. |
| 8,747,897 B2 | 6/2014 | Kidane et al. |
| 8,748,657 B2 | 6/2014 | Batra et al. |
| 8,809,334 B2 | 8/2014 | Clozel |
| 8,846,021 B2 | 9/2014 | Charles |
| 8,877,710 B2 | 11/2014 | Johansson |
| 8,940,930 B2 | 1/2015 | Batra et al. |
| 8,957,240 B2 | 2/2015 | Hogan et al. |
| 9,050,311 B2 | 6/2015 | Batra et al. |
| 9,102,660 B2 | 8/2015 | Batra et al. |
| 9,156,786 B2 | 10/2015 | Batra et al. |
| 9,199,908 B2 | 12/2015 | Phares et al. |
| 9,255,064 B2 | 2/2016 | Malinin et al. |
| 9,278,901 B2 | 3/2016 | Phares et al. |
| 9,346,738 B2 | 5/2016 | Ghone et al. |
| 9,371,264 B2 | 6/2016 | Becker et al. |
| 9,394,227 B1 | 7/2016 | Zhang et al. |
| 9,422,223 B2 | 8/2016 | Phares et al. |
| 9,469,600 B2 | 10/2016 | Malinin et al. |
| 9,505,704 B2 | 11/2016 | Gao et al. |
| 9,505,737 B2 | 11/2016 | Becker et al. |
| 9,643,911 B2 | 5/2017 | Zhang et al. |
| 2002/0099034 A1 | 7/2002 | Moriarty et al. |
| 2003/0108512 A1 | 6/2003 | Shorr et al. |
| 2004/0176645 A1 | 9/2004 | Moriarty et al. |
| 2005/0080140 A1 | 4/2005 | Hatae et al. |
| 2005/0085540 A1 | 4/2005 | Phares et al. |
| 2005/0165110 A1 | 7/2005 | Wade et al. |
| 2005/0165111 A1 | 7/2005 | Wade et al. |
| 2005/0282901 A1 | 12/2005 | Phares et al. |
| 2007/0078095 A1 | 4/2007 | Phares et al. |
| 2007/0078182 A1 | 4/2007 | Phares et al. |
| 2007/0082948 A1 | 4/2007 | Phares et al. |
| 2007/0254032 A1 | 11/2007 | Kidane et al. |
| 2008/0200449 A1 | 8/2008 | Olschewski et al. |
| 2008/0249167 A1 | 10/2008 | Phares et al. |
| 2008/0280986 A1 | 11/2008 | Wade et al. |
| 2009/0036465 A1 | 2/2009 | Roscigno et al. |
| 2009/0163738 A1 | 6/2009 | Batra et al. |
| 2010/0076083 A1 | 3/2010 | Olschewski et al. |
| 2010/0166700 A1 | 7/2010 | Charles |
| 2010/0282622 A1 | 11/2010 | Phares |
| 2010/0324313 A1 | 12/2010 | Hogan et al. |
| 2011/0092599 A1 | 4/2011 | Wade et al. |
| 2011/0118213 A1 | 5/2011 | Phares et al. |
| 2011/0136818 A1 | 6/2011 | Clozel |
| 2011/0268732 A1 | 11/2011 | Johansson |
| 2011/0294815 A1 | 12/2011 | Harbeson |
| 2011/0319641 A1 | 12/2011 | Batra et al. |
| 2012/0010159 A1 | 1/2012 | Rothblatt et al. |
| 2012/0129941 A1 | 5/2012 | Wade et al. |
| 2012/0184622 A1 | 7/2012 | Freissmuth et al. |
| 2012/0190888 A1 | 7/2012 | Batra et al. |
| 2012/0197041 A1 | 8/2012 | Batra et al. |
| 2012/0216801 A1 | 8/2012 | Olschewski et al. |
| 2012/0283470 A1 | 11/2012 | Batra et al. |
| 2012/0295980 A1 | 11/2012 | Phares et al. |
| 2013/0040898 A1 | 2/2013 | Johansson |
| 2013/0053581 A1 | 2/2013 | Wei et al. |
| 2013/0096200 A1 | 4/2013 | Wade et al. |
| 2013/0165389 A1 | 6/2013 | Schellenberger |
| 2013/0184295 A1 | 7/2013 | Sprague et al. |
| 2013/0261187 A1 | 10/2013 | Phares et al. |
| 2013/0267734 A1 | 10/2013 | Batra et al. |
| 2013/0274261 A1 | 10/2013 | Sands |
| 2013/0289304 A1 | 10/2013 | Batra et al. |
| 2013/0317245 A1 | 11/2013 | Wei et al. |
| 2013/0317249 A1 | 11/2013 | Hogan et al. |
| 2013/0331593 A1 | 12/2013 | McGowan et al. |
| 2013/0337534 A1 | 12/2013 | Charles |
| 2013/0344038 A1 | 12/2013 | Freissmuth et al. |
| 2014/0018430 A1 | 1/2014 | Freissmuth et al. |
| 2014/0018431 A1 | 1/2014 | Wade et al. |
| 2014/0024856 A1 | 1/2014 | Giust et al. |
| 2014/0044797 A1 | 2/2014 | Johansson et al. |
| 2014/0193379 A1 | 7/2014 | Jeffs et al. |
| 2014/0249093 A1 | 9/2014 | Vetter et al. |
| 2014/0256730 A1 | 9/2014 | Becker et al. |
| 2014/0275616 A1 | 9/2014 | Batra et al. |
| 2014/0288314 A1 | 9/2014 | Batra et al. |
| 2014/0296150 A1 | 10/2014 | Hersel et al. |
| 2014/0303245 A1 | 10/2014 | Sprogoee et al. |
| 2014/0303252 A1 | 10/2014 | Kidane et al. |
| 2014/0322207 A1 | 10/2014 | Johansson |
| 2014/0323567 A1 | 10/2014 | Laing |
| 2014/0329824 A1 | 11/2014 | Clozel |
| 2015/0005374 A1 | 1/2015 | Phares et al. |
| 2015/0050714 A1 | 2/2015 | Charles |
| 2015/0057325 A1 | 2/2015 | Johansson et al. |
| 2015/0087688 A1 | 3/2015 | Hersel et al. |
| 2015/0105582 A1 | 4/2015 | Batra et al. |
| 2015/0126761 A1 | 5/2015 | Jain et al. |
| 2015/0126764 A1 | 5/2015 | Hogan et al. |
| 2015/0148414 A1 | 5/2015 | Malinin et al. |
| 2015/0166503 A1 | 6/2015 | Becker et al. |
| 2015/0175529 A1 | 6/2015 | Malinin et al. |
| 2015/0259274 A1 | 9/2015 | Phares et al. |
| 2015/0299091 A1 | 10/2015 | Batra et al. |
| 2015/0376106 A1 | 12/2015 | Batra et al. |
| 2016/0030371 A1 | 2/2016 | Phares et al. |
| 2016/0051505 A1 | 2/2016 | Phares et al. |
| 2016/0152548 A1 | 6/2016 | Gao et al. |
| 2016/0243064 A1 | 8/2016 | Trehan et al. |
| 2016/0256425 A1 | 9/2016 | Malinin et al. |
| 2016/0289158 A1 | 10/2016 | Chambournier et al. |
| 2016/0318844 A1 | 11/2016 | Malinin et al. |
| 2016/0355455 A1 | 12/2016 | Phares et al. |
| 2016/0368854 A1 | 12/2016 | Zhang et al. |

(56) References Cited

U.S. PATENT DOCUMENTS

| | | |
|---|---|---|
| 2016/0368855 A1 | 12/2016 | Zhang et al. |
| 2016/0368889 A1 | 12/2016 | Becker et al. |

FOREIGN PATENT DOCUMENTS

| | | |
|---|---|---|
| EP | 2252570 A1 | 11/2010 |
| EP | 2427054 A1 | 3/2012 |
| EP | 2674413 A1 | 12/2013 |
| EP | 2792353 A2 | 10/2014 |
| EP | 2792353 A3 | 10/2014 |
| EP | 2841109 A1 | 3/2015 |
| EP | 2861554 A2 | 4/2015 |
| EP | 2978313 A1 | 2/2016 |
| EP | 3060041 A2 | 8/2016 |
| EP | 3068752 A1 | 9/2016 |
| WO | WO 00/57701 A1 | 10/2000 |
| WO | WO 01/93862 A1 | 12/2001 |
| WO | WO 02/053517 A2 | 7/2002 |
| WO | WO 02/053517 A3 | 7/2002 |
| WO | WO 03/049676 A2 | 6/2003 |
| WO | WO 03/049676 A3 | 6/2003 |
| WO | WO 2005/007081 | 1/2005 |
| WO | WO 2005/007081 A3 | 1/2005 |
| WO | WO 2005/058303 A1 | 6/2005 |
| WO | WO 2005/058329 A1 | 6/2005 |
| WO | WO 2007/100902 A2 | 9/2007 |
| WO | WO 2007/100902 A3 | 9/2007 |
| WO | WO 2007/127216 A2 | 11/2007 |
| WO | WO 2007/127216 A3 | 11/2007 |
| WO | WO 2007/134292 A3 | 11/2007 |
| WO | WO 2008/002929 A2 | 1/2008 |
| WO | WO 2008/002929 A3 | 1/2008 |
| WO | WO 2008/049000 A2 | 4/2008 |
| WO | WO 2008/049000 A3 | 4/2008 |
| WO | WO 2008/098196 A1 | 8/2008 |
| WO | WO 2009/078965 A1 | 6/2009 |
| WO | WO 2009/152160 | 12/2009 |
| WO | WO 2009/158010 A1 | 12/2009 |
| WO | WO 2010/018549 A2 | 2/2010 |
| WO | WO 2010/018549 A3 | 2/2010 |
| WO | WO 2010/075861 A2 | 7/2010 |
| WO | WO 2010/075861 A3 | 7/2010 |
| WO | WO 2010/129757 A1 | 11/2010 |
| WO | WO 2011/005505 A2 | 1/2011 |
| WO | WO 2011/005505 A3 | 1/2011 |
| WO | WO 2011/015630 A1 | 2/2011 |
| WO | WO 2011/123813 A2 | 10/2011 |
| WO | WO 2011/123813 A3 | 10/2011 |
| WO | WO 2011/134478 A2 | 11/2011 |
| WO | WO 2011/134478 A3 | 11/2011 |
| WO | WO 2011/153363 A1 | 12/2011 |
| WO | WO 2012/006273 A1 | 1/2012 |
| WO | WO 2012/009816 | 1/2012 |
| WO | WO 2012/088607 A1 | 7/2012 |
| WO | WO 2012/095511 A1 | 7/2012 |
| WO | WO 2012/107363 A1 | 8/2012 |
| WO | WO 2012/107364 A1 | 8/2012 |
| WO | WO 2012/143012 A1 | 10/2012 |
| WO | WO 2013/022846 | 2/2013 |
| WO | WO 2013/024051 | 2/2013 |
| WO | WO 2013/024052 | 2/2013 |
| WO | WO 2013/024053 A1 | 2/2013 |
| WO | WO 2013/143548 A1 | 10/2013 |
| WO | WO 2013/160340 A1 | 10/2013 |
| WO | WO 2013/174848 A2 | 11/2013 |
| WO | WO 2013/174848 A3 | 11/2013 |
| WO | WO 2014/022373 A1 | 2/2014 |
| WO | WO 2014/089385 A2 | 6/2014 |
| WO | WO 2014/089385 A3 | 6/2014 |
| WO | WO 2014/110094 A1 | 7/2014 |
| WO | WO 2014/110491 A1 | 7/2014 |
| WO | WO 2014/150203 A1 | 9/2014 |
| WO | WO 2014/160638 A1 | 10/2014 |
| WO | WO 2014/179295 A1 | 11/2014 |
| WO | WO 2014/203278 A2 | 12/2014 |
| WO | WO 2014/203278 A3 | 12/2014 |
| WO | WO 2015061720 A2 | 4/2015 |
| WO | WO 2015073314 A1 | 5/2015 |
| WO | WO 2015061720 A3 | 6/2015 |
| WO | WO 2015138423 A1 | 9/2015 |
| WO | WO 2015138423 A9 | 11/2015 |
| WO | WO 2016010538 A1 | 1/2016 |
| WO | WO 2016055819 A1 | 4/2016 |
| WO | WO 2016081658 A1 | 5/2016 |
| WO | WO 2016120311 A1 | 8/2016 |
| WO | WO 2016176555 A1 | 11/2016 |
| WO | WO 2016205202 A1 | 12/2016 |

OTHER PUBLICATIONS

Gannes L Z et al., "Natural abundance variations in stable isotopes and their potential uses in animal physiological ecology", Comp Biochem Physiol Mol Integr Physiol, 119:725-737 (1998).

*Handbook of Reagents of Organic Synthesis*: Activating Agents and Protecting Groups, Pearson and Rousch (Ed.), John Wiley & Sons (1999).

Shiina, Isamu, "Total Synthesis of Natural 8- and 9-Membered lactones: Recent Advancements in Medium Sized Ring Formations", Chemical Reviews 107, 239-273 (2007).

Smith, Michael B. et al. "March's Advanced Organic Chemistry: Reactions, Mechanisms and Structure", 6$^{th}$ Ed., Wiley & Sons (2007).

Thayer, Chemical & Engineering News, Jun. 18, 2007, vol. 85. Issue 25, pp. 17-30.

Wada E et al., "Natural abundance of carbon, nitrogen, and hydrogen isotope ratios in biogenic substances: present and future," Seikagaku, , 66:15-29 (English portions included). (1994).

Wuts, Peter G. and Greene, Theodora W., "Greene's Protective Groups in Organic Synthesis", 4$^{th}$ Ed., John Wiley & Sons (2007).

Invitation to pay additional fees with partial international search report received in connection with international patent application No. PCT/US2014/046920; dated Sep. 11, 2014.

International Search Report and Written Opinion received in connection with international patent application No. PCT/US2014/011260; dated May 6, 2014.

Findlay et al., Prostaglandins, Leukotrienes and Essential Fatty Acids, vol. 48, Issue No. 2, 1993, pp. 167-174.

Geiger et al., Biomaterials, vol. 31, Issue No. 10, 2010, pp. 2903-2911.

Zhang et al., "Treprostinil Derivatives and Compositions and Uses Thereof" U.S. Appl. No. 14/829,180, filed Aug. 18, 2015.

Hea-Jeong Doh et al., Synthesis and Evaluation of Ketorolac Ester Prodrugs for Transdermal Delivery, J. of Pharmaceutical Sciences, vol. 92, No. 5, May 2003.

Schanz, et al., "Topical treatment of erectile dysfunction with prostaglandin E1 ethyl ester", J. Dtsch Dermatol. Ges., 7:1055-59 (2009).

Rautio et al., "Prodrugs: design and clinical applications", Nature Reviews: Drug Discovery 2008, 7, 2008, 255-270.

Paudel et al., "Challenges and Opportunities in dermal/transdermal Delivery", Ther Deliv., 2010, 1, 109-131.

TREPROSTINIL DERIVATIVE COMPOUNDS AND METHODS OF USING SAME

DESCRIPTION OF RELATED APPLICATIONS

This application claims priority to U.S. provisional application 61/751,608 filed Jan. 11, 2013 which is incorporated herein by reference in its entirety for all purposes.

BACKGROUND

Pulmonary hypertension (PH) or pulmonary arterial hypertension (PAH) is a disease which can result in death and is characterized by increased pulmonary artery pressure and pulmonary vascular resistance. A need exists for better compounds and methods for treating PH and PAH. See, for example, US Patent Publication No. 2013/0274261. Many valuable pharmacologically active compounds, including some of interest with respect to PH and PAH, cannot be effectively administered orally for various reasons and are generally administered via intravenous or intramuscular routes. These routes of administration generally require intervention by a physician or other health care professional, and can entail considerable discomfort as well as potential local trauma to the patient. One example of such a compound is treprostinil and derivatives thereof, which has been used in the treatment of PH and PAH. See, for example, WO 2005/007081. The core chemical formula is (herein also labeled, Compound A):

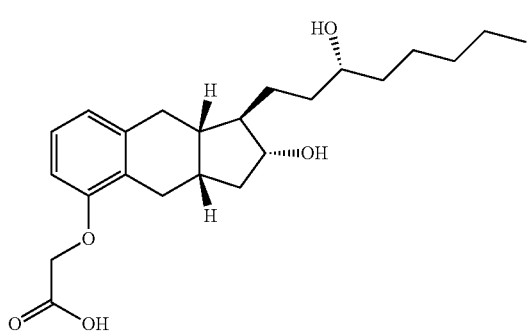 [SMILES: CCCCC[C@@H](O)CC[C@@H]1[C@H]2Cc3cccc(OCC(=O)O)c3C[C@H]2C[C@H]1O]

including pharmaceutically acceptable salts such as the sodium salt.

Accordingly, there is a clinical need in providing treprostinil by improved formulations and methods, e.g., either orally or transdermally. More particularly, there is a need for a safe and effective method for increasing the systemic availability of treprostinil via administration of treprostinil or treprostinil analogs.

The application of transdermal drug delivery technology to the administration of a wide variety of drugs has been proposed and various systems for accomplishing this are disclosed in numerous technical journals and U.S. Pat. Nos. 3,598,122, 4,144,317, 4,201,211, 4,262,003, and 4,379,454, all of which are incorporated herein by reference, are representative of various transdermal drug delivery systems of the prior art, which systems have the ability of delivering controlled amounts of drugs to patients for extended periods of time ranging in duration from several hours to several days. None of the above patents nor any other prior art of which the inventors are aware describes a transdermal delivery system which is intended to deliver treprostinil or its derivatives nor are they aware of data on skin permeability or therapeutic transdermal delivery rates adequate to design such a system.

SUMMARY

Embodiments described herein including compounds, compositions, and devices, as well as methods of making and methods of using the same.

One embodiment provides a compound represented by Formula (I)

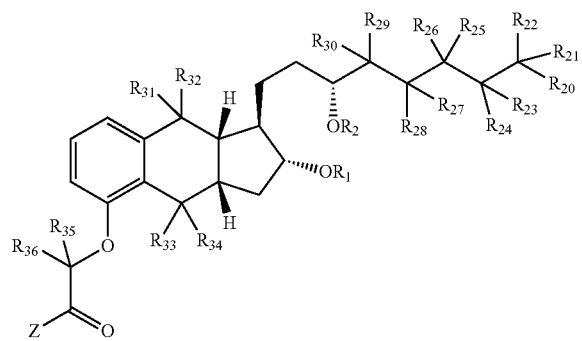

wherein, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently H or deuterium;

Z is —OH, —$OR_{11}$, —$N(R_{11})R_{12}$, —$SR_{11}$, or $P_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from the group consisting of:

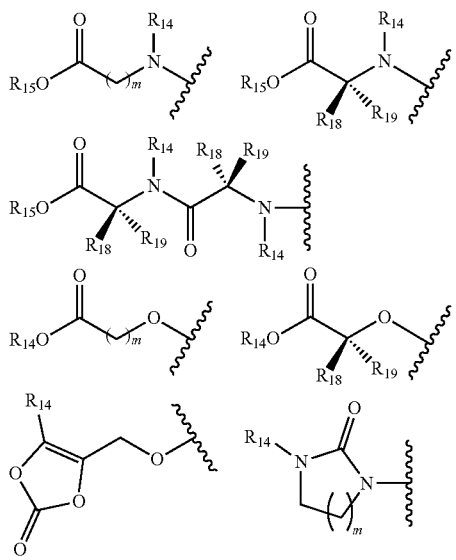

-continued

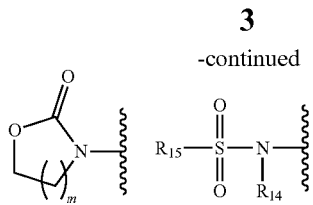

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the list consisting of alkyl, halo, haloalkyl, hydroxy, and alkoxy, haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

and, $R_1$ and $R_2$ are independently H or $P_2$, wherein at least one of $R_1$ and $R_2$ is $P_2$, wherein $P_2$ is selected from the group consisting of:

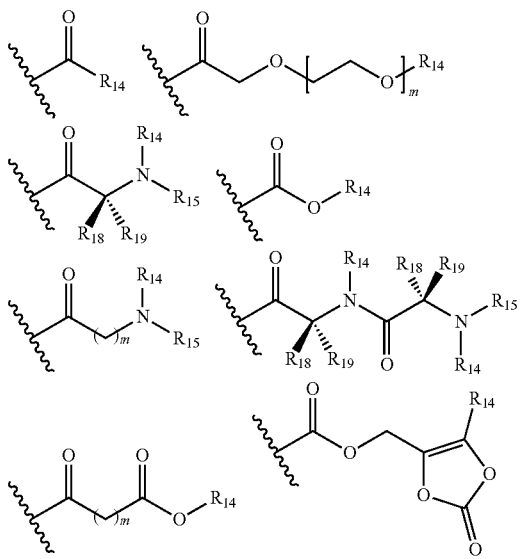

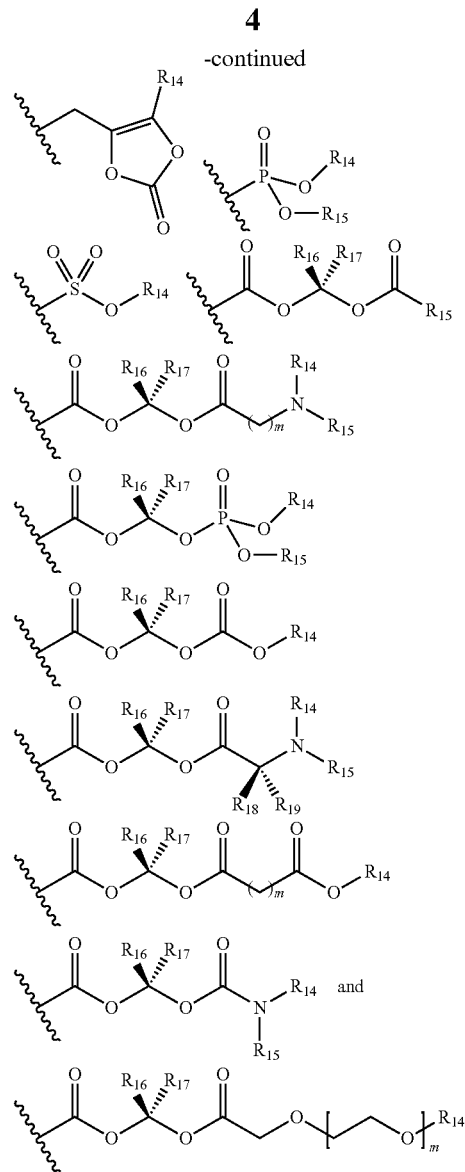

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, and polymorphs of the compounds of Formula I.

In another embodiment, the parameters of Formula I are defined as follows:

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently H or deuterium;

Z is —$OR_{11}$, —$N(R_{11})R_{12}$, —$SR_{11}$, or $P_1$;

$R_{11}$ is branched alkyl, haloalkyl, halocycloalkyl, heteroalkyl, substituted heteroalkyl, cycloheteroalkyl, substituted cycloheteroalkyl, bicycloalkyl, alkylcycloalkyl, substituted alkylcycloalkyl, alkylcycloheteroalkyl, substituted alkylcycloheteroalkyl, alkylaryl, substituted alkylaryl, heteroaryl, substituted heteroaryl, alkylheteroaryl, substituted alkylheteroaryl;

$R_{12}$ is H, branched alkyl, haloalkyl, heteroalkyl, cycloheteroalkyl, alkylcycloalkyl, alkylcycloheteroalkyl, aryl, or heteroaryl;

$P_1$ is selected from the group consisting of:

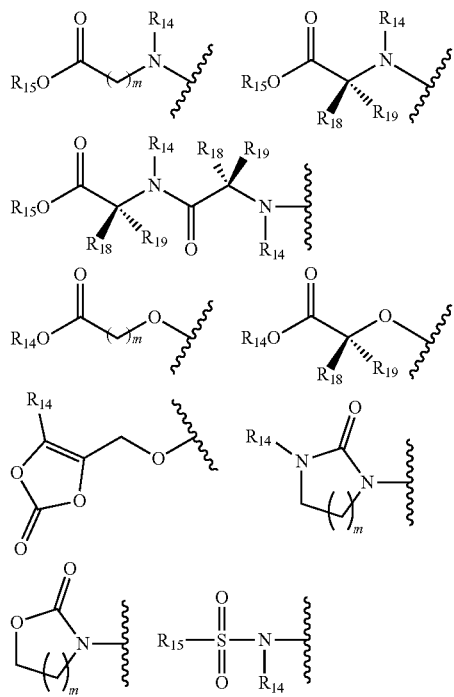

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —$CONH_2$, aryl, and heteroaryl, wherein the aryl or heteroaryl are unsubstituted or substituted from the list consisting of alkyl, halo, haloalkyl, hydroxy, and alkoxy, haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

and, $R_1$ and $R_2$ are independently H or $P_2$, wherein $P_2$ is selected from the group consisting of:

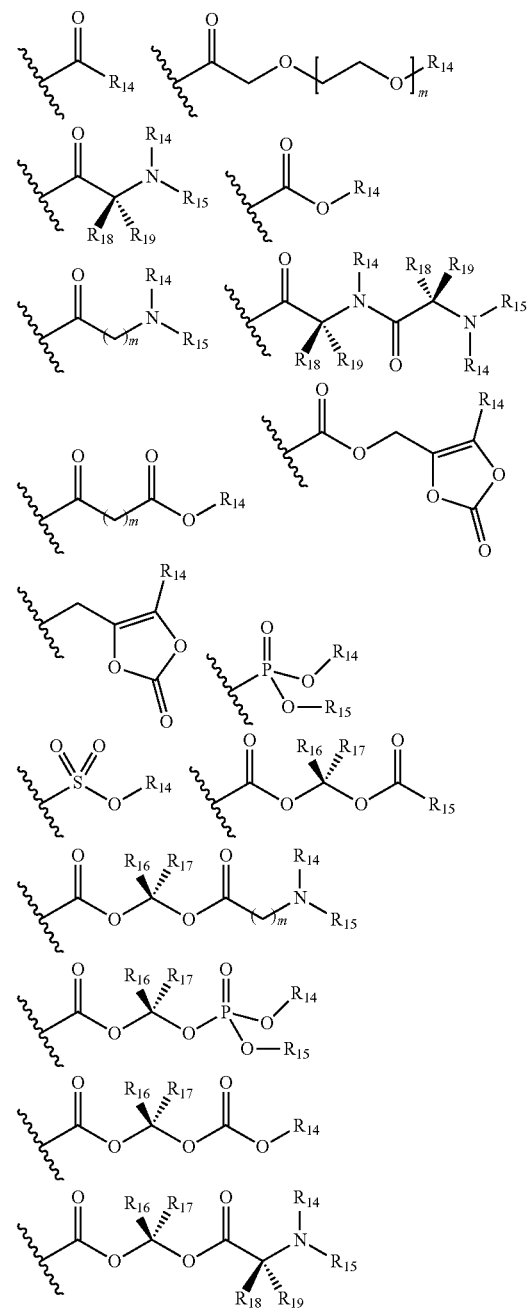

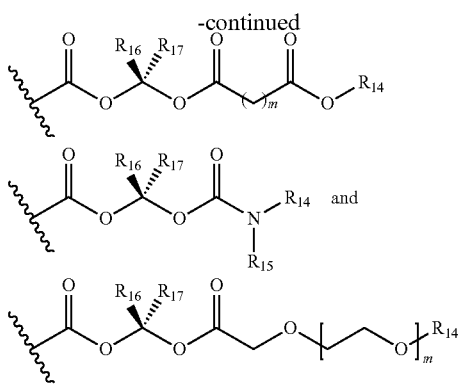

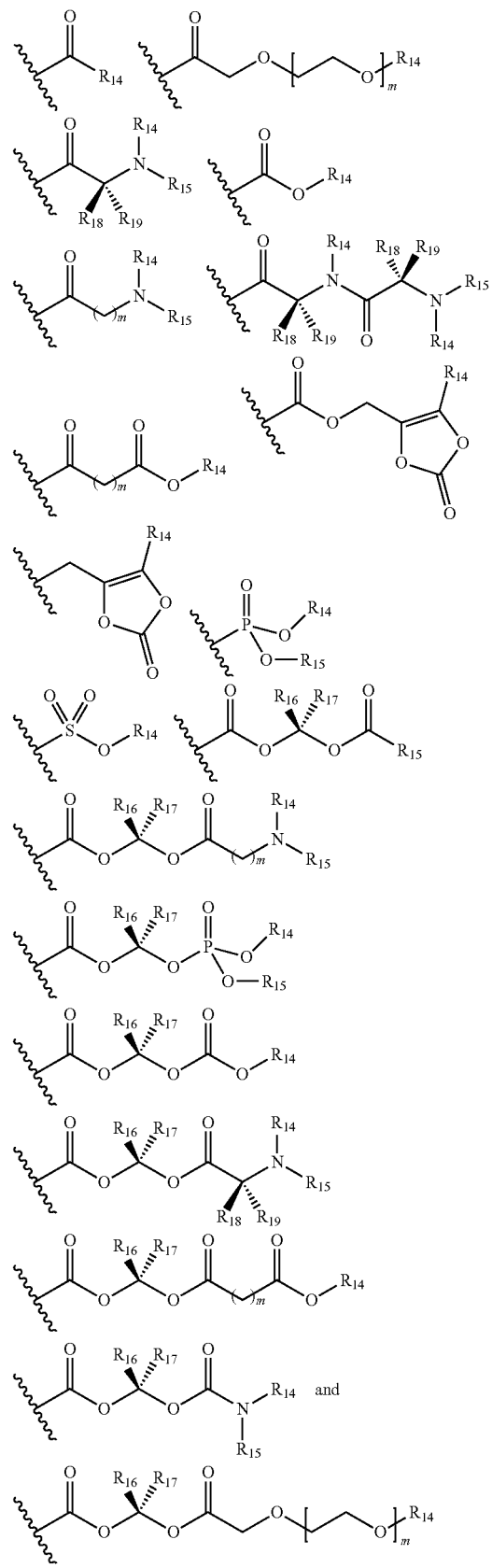

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, and polymorphs of the compounds of Formula I.

In another embodiment, provided is a compound represented by Formula II:

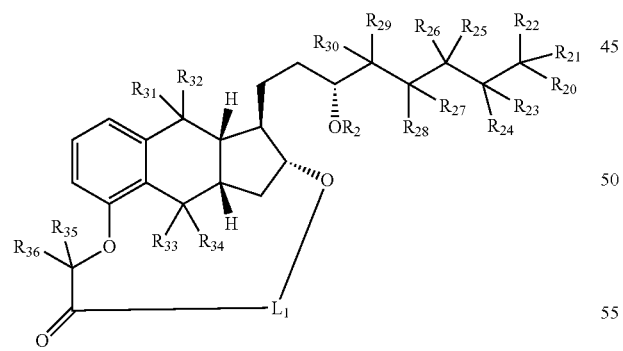

wherein, $R_2$ is selected from the group consisting of H and $P_2$;

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;

$L_1$ is a selected from the group consisting of —O-alkylene-C(O)—, —O-alkylene-OC(O)—, or a bond; wherein $P_2$ is selected from the group consisting of:

wherein, m is 1, 2, 3, or 4;
$R_{14}$ and $R_{15}$ are as defined above;
$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;
$R_{16}$ and $R_{17}$ are independently in each occurrence H or alkyl;
$R_{16}$ and $R_{17}$ taken together with the atoms to which they attach optionally form a 3- to 6-membered ring;
$R_{18}$ and $R_{19}$ are as defined above;
$R_{14}$ and $R_{18}$ taken together with the atoms to which they attach optionally form a 5- to 7-membered ring;
$R_{14}$ and $R_{19}$ taken together with the atoms to which they attach optionally form a 5- to 7-membered ring;
wherein Formula II includes enantiomers, pharmaceutically acceptable salts, and polymorphs of the compounds of Formula II.

In another embodiment, a compound is represented by Formula III:

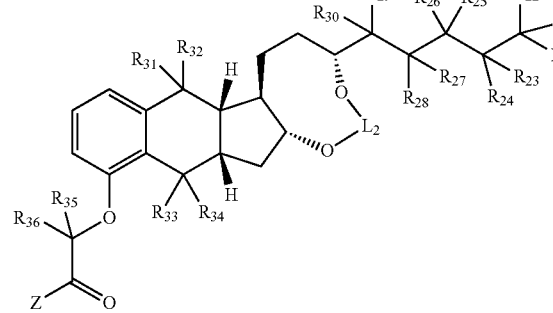

$L_2$ is selected from the group consisting of:

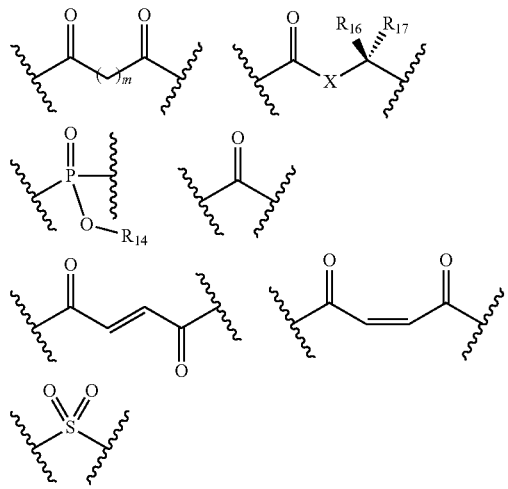

wherein,
m is 1, 2, 3, or 4;
X is $NR_{14}$, or O;
$R_{14}$ is selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, substituted heteroarylalkyl;

$R_{16}$ and $R_{17}$ are independently in each occurrence H or alkyl;
$R_{16}$ and $R_{17}$ taken together with the atoms to which they attach optionally form a 3- to 6-membered ring; and
$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;
wherein Z is —OH, —$OR_{11}$, —$N(R_{11})R_{12}$, —$SR_{11}$, or $P_1$;
$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;
$R_{12}$ is H, haloalkyl, heteroalkyl, cycloheteroalkyl, alkylcycloalkyl, alkylcycloheteroalkyl, aryl, or heteroaryl;
$P_1$ is selected from the group consisting of:

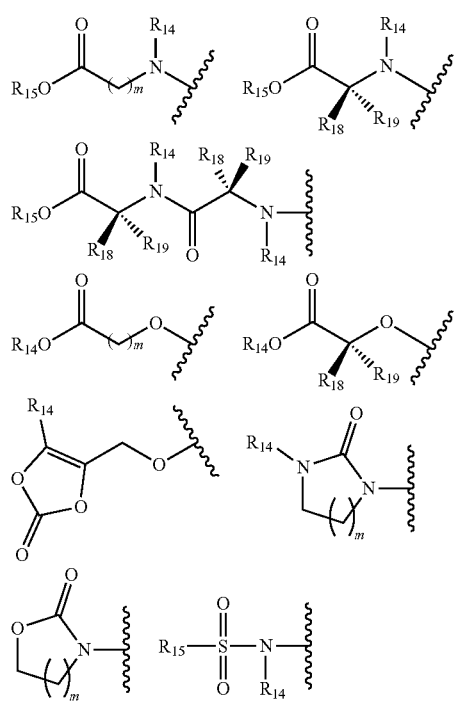

wherein,
m is 1, 2, 3, or 4;
$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;
$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;
$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —$CONH_2$, aryl, and heteroaryl, wherein the aryl or heteroaryl are unsubstituted or substituted from the list consisting of alkyl, halo, haloalkyl, hydroxy, and alkoxy, haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

wherein Formula III includes enantiomers, pharmaceutically acceptable salts, and polymorphs of the compounds of Formula III.

Another embodiment provides a compound represented by Formula IV:

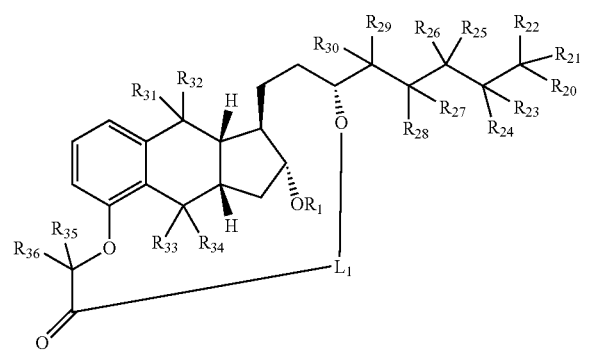

$R_1$ is selected from the group consisting of H and $P_2$;

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;

$L_1$ is a selected from the group consisting of —O-alkylene-C(O)—, —O-alkylene-OC(O)—, or a bond; wherein $P_2$ is selected from the group consisting of:

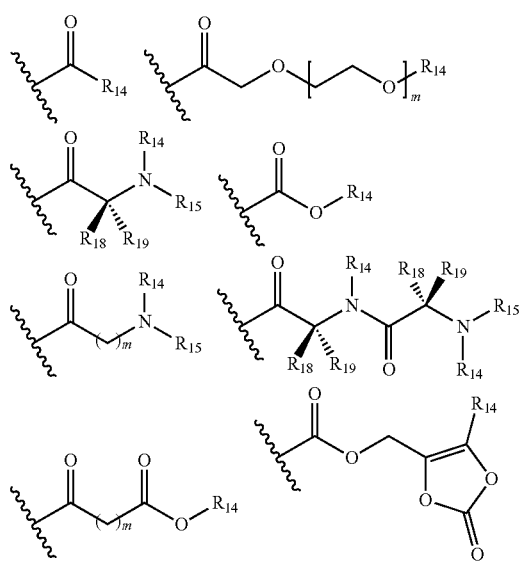

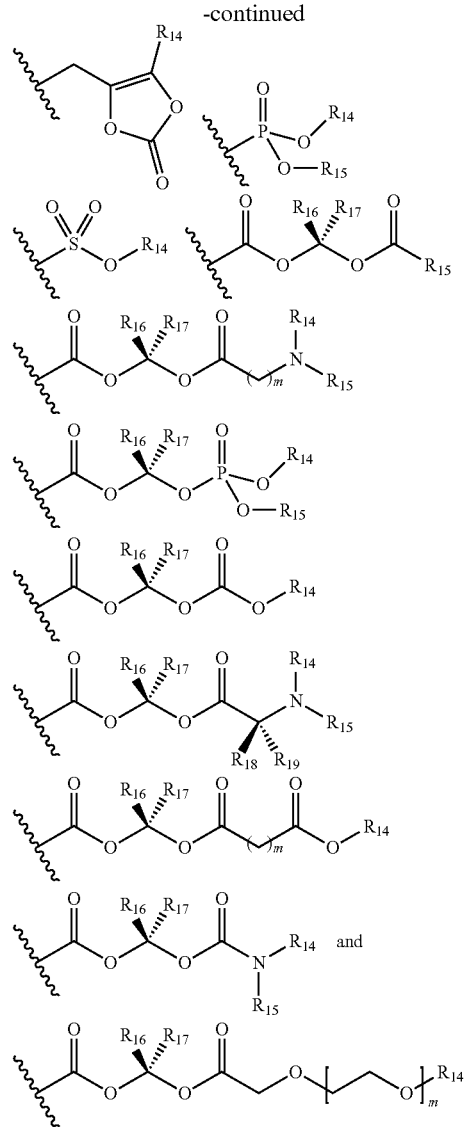

wherein,
m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the list consisting of alkyl, halo, haloalkyl, hydroxy, and alkoxy, haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula IV includes enantiomers, pharmaceutically acceptable salts, and polymorphs of the compounds of Formula IV.

Compositions are also provided including a composition comprising at least one compound according to Formula I, II, III, and IV and at least one other component. In one embodiment, the composition is formulated for transdermal delivery. In another embodiment, the composition is formulated for transdermal delivery with a patch. In one embodiment, the composition can further comprise at least one solvent. In one embodiment, the amount of the compound according to Formula I, II, III, or IV is adapted to provide a useful delivery profile for treatment of a human. In one embodiment, the treatment is carried out on a subject, such as a mammal, but the subject is not a human.

At least one advantage for at least one embodiment includes ability to tailor the chemical structure of a pharmaceutically useful motif for a particular uses including treatment and prophylactic use against, for example, PH and PAH. For example, the drug delivery profile can be adapted for a particular application.

At least one additional advantage for at least one embodiment includes ability to use the compounds to provide better bioavailability including use in transdermal drug delivery applications.

DETAILED DESCRIPTION

Introduction

Priority U.S. provisional application 61/751,608 filed Jan. 11, 2013 is incorporated herein by reference in its entirety for all purposes including the chemical formulae and claims, including Formula I, Formula II, and Formula III, as well as Schemes 1-4, examples, and the tables of structures on pages 14-16.

Various prostacyclin analogs, including treprostinil, and methods for their use are known. For example, they can be used in promoting vasodilation, inhibiting platelet aggregation and thrombus formation, stimulating thrombolysis, inhibiting cell proliferation (including vascular remodeling), providing cytoprotection, and preventing atherogenesis and inducing angiogenesis. Through these prostacyclin-mimetic mechanisms, these compounds may be used in the treatment of/for: pulmonary hypertension, ischemic diseases (e.g., peripheral vascular disease, Raynaud's phenomenon, Scleroderma, myocardial ischemia, ischemic stroke, renal insufficiency), heart failure (including congestive heart failure), conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation, and other emerging therapeutic areas where prostacyclin treatment appears to have a beneficial role. These compounds may also demonstrate additive or synergistic benefit in combination with other cardiovascular agents (e.g., calcium channel blockers, phosphodiesterase inhibitors, endothelial antagonists, and antiplatelet agents).

Treprostinil is a chemically stable analog of prostacyclin. Although treprostinil sodium (Remodulin®) is approved by the Food and Drug Administration (FDA) for subcutaneous administration, treprostinil as the free acid has an absolute oral bioavailability of less than 10% and a very short systemic half life due to significant metabolism.

Definitions

Herein, listings of chemical groups represented by multiple chemical formulae are provided (e.g., $P_1$, $P_2$, $L_1$, and $L_2$). As used herein, these group listings also describe any combination of subgroups of the chemical formulae in the group listing as well as any single formula in the group listing.

The term "alkyl," as used herein, refers to a monovalent saturated hydrocarbon group. $C_1$-$C_8$ alkyl is an alkyl having from 1 to 8 carbon atoms and includes, for example, $C_1$-$C_3$ alkyl, $C_1$-$C_5$ alkyl, and $C_1$-$C_7$ alkyl. An alkyl may be linear or branched. Examples of alkyl groups include methyl, ethyl, n-propyl, isopropyl, n-butyl, isobutyl, sec-butyl, t-butyl, n-pentyl, isopentyl, neopentyl and n-hexyl.

The term "haloalkyl," as used herein, refers monovalent saturated hydrocarbon group attached to a one or more halogen selected from Cl and F. Specific examples include 2-fluoroethyl, 2,2-difluoroethyl, 2-fluoropropyl, and 2,2-difluoropropyl.

The term "heteroalkyl," as used herein, refers to a monovalent saturated hydrocarbon group attached to one or more hetero atoms selected from O, N, and S, $C_1$-$C_8$ heteroalkyl is an alkyl having from 1 to 8 carbon atoms followed by a heteroatom selected from O, N, S and includes, for example, $C_1$-$C_3$—OH, $C_1$-$C_5$—SH, and $C_1$-$C_7$—NH$_2$. It also includes C1-C2-O—C3-C4-OH, and C1-C2-NH—C3-C4-OH The term "cycloalkyl," as used herein, refers to a monocyclic, bicyclic, or tricyclic monovalent saturated hydrocarbon ring system. The term "$C_3$-$C_{14}$ cycloalkyl" refers to a cycloalkyl wherein the number of ring carbon atoms is from 3 to 14. Examples of $C_3$-$C_{14}$ cycloalkyl include $C_3$-$C_{10}$ cycloalkyl and $C_3$-$C_6$ cycloalkyl. Bicyclic and tricyclic ring systems include fused, bridged and spirocyclic ring systems. More particular examples of cycloalkyl groups include cyclopropyl, cyclobutyl, cyclopentyl, cyclohexyl, cycloheptyl, cis- and trans-decalynil, norbornyl, adamantyl, and spiro[4.5]decanyl.

The term "cycloheteroalkyl," as used herein, refers to a monocyclic, bicyclic, or tricyclic monovalent saturated ring system wherein from 1 to 4 ring atoms are heteroatoms independently selected from the group consisting of O, N and S. The term "3 to 14-membered cycloheteroalkyl" refers to a cycloheteroalkyl wherein the number of ring atoms is from 3 to 14. Examples of 3 to 14-membered cycloheteroalkyl include 3 to 10-membered cycloheteroalkyl and 3 to 6-membered cycloheteroalkyl. Bicyclic and tricyclic ring systems include fused, bridged and spirocyclic ring systems. More particular examples of cycloheteroalkyl groups include azepanyl, azetidinyl, aziridinyl, imidazolidinyl, morpholinyl, oxazolidinyl, oxazolidinyl, piperazinyl, piperidinyl, pyrazolidinyl, pyrrolidinyl, quinuclidinyl, tetrahydrofuranyl, thiomorpholinyl, and α-methyl-1,3-dioxol-2-onyl.

The term "alkylcycloalkyl," as used herein, refers to a monocyclic, bicyclic, or tricyclic monovalent saturated hydrocarbon ring system. The term "$C_3$-$C_{14}$ cycloalkyl"

refers to a cycloalkyl wherein the number of ring carbon atoms is from 3 to 14. Examples of $C_3$-$C_{14}$ cycloalkyl include $C_3$-$C_{10}$ cycloalkyl and $C_3$-$C_6$ cycloalkyl. Bicyclic and tricyclic ring systems include fused, bridged, and spirocyclic ring systems linked to an alkyl group which refers to a monovalent saturated hydrocarbon group. $C_1$-$C_8$ alkyl is an alkyl having from 1 to 8 carbon atoms and includes, for example, $C_1$-$C_3$ alkyl, $C_1$-$C_5$ alkyl, and $C_1$-$C_7$ alkyl. Particular examples include cyclopropyl methyl, cyclopropyl ethyl, and cyclohexyl ethyl.

The term "alkylheterocycloalkyl," as used herein, refers to an alkyl that refers to a monovalent saturated hydrocarbon group. $C_1$-$C_8$ alkyl is an alkyl having from 1 to 8 carbon atoms and includes, for example, $C_1$-$C_3$ alkyl, $C_1$-$C_5$ alkyl, and $C_1$-$C_7$ alkyl attached to cycloalkyl which refers to a monocyclic, bicyclic, or tricyclic monovalent saturated ring system wherein from 1 to 4 ring atoms are heteroatoms independently selected from the group consisting of O, N, and S. The term "3 to 14-membered heterocycloalkyl" refers to a heterocycloalkyl wherein the number of ring atoms is from 3 to 14. Examples of 3 to 14-membered heterocycloalkyl include 3 to 10-membered heterocycloalkyl and 3 to 6-membered heterocycloalkyl. Bicyclic and tricyclic ring systems include fused, bridged and spirocyclic ring systems. Specific examples include N-ethylmorpholine, N-ethylpiperidine, 4-ethylpiperidine, 1-methyl-4-ethylpiperidine, and N-ethylpiperazine.

The term "aryl," as used herein, refers to a monovalent aromatic carbocyclic ring system, which may be a monocyclic, fused bicyclic, or fused tricyclic ring system. The term "$C_6$-$C_{14}$ aryl" refers to an aryl having from 6 to 14 ring carbon atoms. An example of $C_6$-$C_{14}$ aryl is $C_6$-$C_{10}$ aryl. More particular examples of aryl groups include phenyl, naphthyl, anthracyl, and phenanthryl.

The term "heteroaryl," as used herein, refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, tetrazolyl, etc; unsaturated condensed heterocyclyl group containing 1 to 5 nitrogen atoms, for example, indolyl, isoindolyl, benzimidazolyl, quinolyl, benzotrazolyl, tetrazolopyridazinyl, etc.; unsaturated 3- to 6-membered heteromonocyclic group containing 1 to 2 oxygen atoms and 1 to 3 nitrogen atoms, for example, oxazolyl, oxadiazolyl, etc.; unsaturated condensed heterocyclyl group containing 1 to 2 oxygen atoms and 1 to 3 nitrogen atoms; unsaturated 3- to 6-membered heteromonocyclic group containing 1 to 2 sulfur atoms and 1 to 3 nitrogen atoms, for example, thiazolyl, thiadiazolyl, etc.; and unsaturated condensed heterocyclyl group containing 1 to 2 sulfur atoms and 1 to 3 nitrogen atoms.

The term "alkylaryl," as used herein, refers to aryl-substituted alkyl radicals such as benzyl, diphenyl methyl, and phenylethyl.

The term "alkylheteroaryl," as used herein, refers to heteroaryl-substituted alkyl radicals such as imidazolylmethyl, thiazolylmethyl, and pyridylethyl.

As used herein, the terms described herein such as alkyl, haloalkyl, heteroalkyl, cycloalkyl, cycloheteroalkyl, alkylcycloalkyl, alkylheterocycloalkyl, aryl, heteroaryl, alkylaryl, and alkylheteroaryl, are understood to cover in some optional embodiments wherein they form rings. For example, as described further herein, in some cases, optionally, groups such as $R_{14}$, $R_{15}$, $R_{16}$, $R_{17}$, $R_{18}$, and $R_{19}$ can form rings with other groups $R_{14}$, $R_{15}$, $R_{16}$, $R_{17}$, $R_{18}$, and $R_{19}$.

The term substituted refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, alkylsulfonyl, alkylsulfonylalkyl, alkoxy, alkoxy, aryloxy, aminocarbonyl, alkylaminocarbonyl, arylaminocarbonyl, alkoxycarbonyl, aryloxycarbonyl, alkylhalo, amino, trifluoromethyl, cyano, nitro, alkylamino, arylamino, alkylaminoalkyl, arylaminoalkyl, hydroxyl, alkyloxyalkyl, carboxyalkyl, alkoxycarbonylalkyl, aminocarbonylalkyl, acyl, carbonyl, carboxylic acid sulfonic acid, phosphonic acid, aryl, heteroaryl, heterocyclic, and aliphatic. It is understood that the substituent may be further substituted within the normal limits of the skilled artisan. A moiety or group may be optionally substituted which means the group may or may not have one or more substituents.

The term "compound" as used herein, is also intended to include salts, solvates, and hydrates thereof. The specific recitation of "salt," "solvate," or "hydrate," in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

Isotopes and Isotopic Abundance

It will be recognized that some variation of natural isotopic abundance occurs in a synthesized compound depending upon the origin of chemical materials used in the synthesis. Thus, a preparation of treprostinil will inherently contain small amounts of deuterated isotopologues. The concentration of naturally abundant stable hydrogen and carbon isotopes, notwithstanding this variation, is small and immaterial with respect to the degree of stable isotopic substitution of compounds of this invention. See, for instance, Wada E et al, *Seikagaku* 1994, 66:15; Ganes L Z et al, *Comp Biochem Physiol Mol Integr Physiol* 1998, 119: 725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In some embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

In other embodiment, a compound of the invention contains less than 10%, preferably less than 6%, and more preferably less than 3% of all other isotopologues combined, including a form that lacks any deuterium. In certain aspects, the compound contains less than "X"% of all other isotopologues combined, including a form that lacks any deuterium; where X is any number between 0 and 10 (e.g., 1, 0.5, 0.001), inclusive. Compositions of matter that contain greater than 10% of all other isotopologues combined are referred to herein as "mixtures" and must meet the parameters set forth below. These limits of isotopic composition and all references to isotopic composition herein, refer solely to the relative amounts of deuterium/hydrogen present in the active, free base form of the compound of Formula I or II, and do not include the isotopic composition of hydrolyzable portions of prodrugs, or of counterions.

The term "isotopologue" refers to species that differ from a specific compound of this invention only in the isotopic composition of their molecules or ions.

Core Structure Formula I

In one embodiment, the present invention provides a compound represented by Formula I:

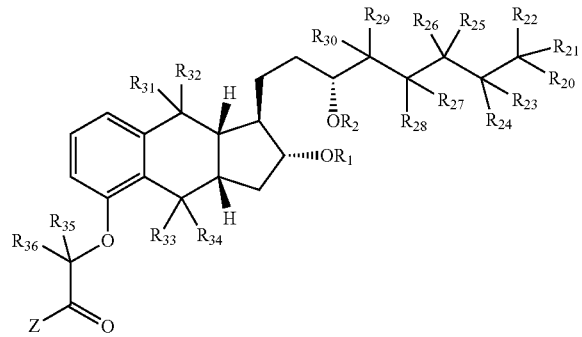

At least two sub-embodiments are provided to define further Formula I.

In a first sub-embodiment of Formula I, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently H or deuterium;

Z is —OH, —$OR_{11}$, —$N(R_{11})R_{12}$, —$SR_{11}$, or $P_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from the group consisting of:

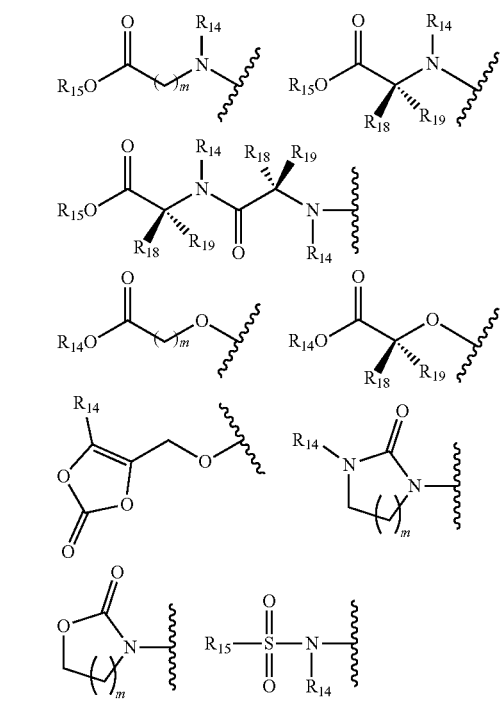

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the list consisting of alkyl, halo, haloalkyl, hydroxy, and alkoxy, haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

and, $R_1$ and $R_2$ are independently H or $P_2$, wherein at least one of $R_1$ and $R_2$ is $P_2$, wherein $P_2$ is selected from the group consisting of:

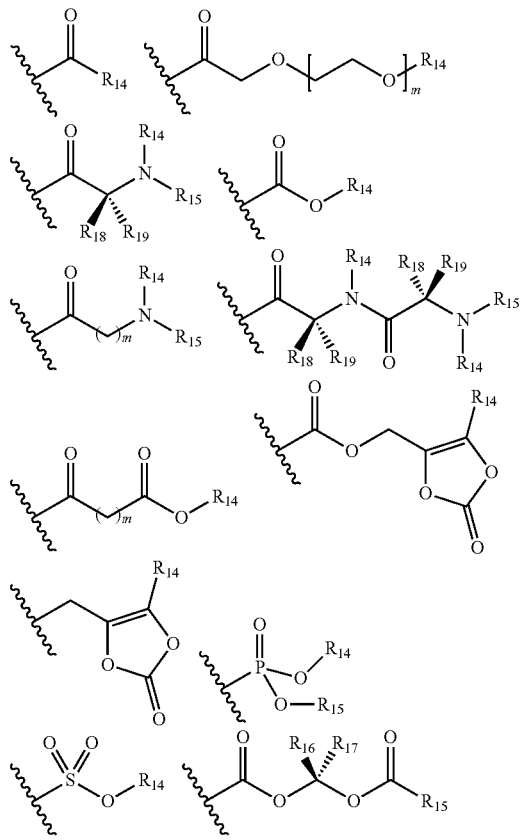

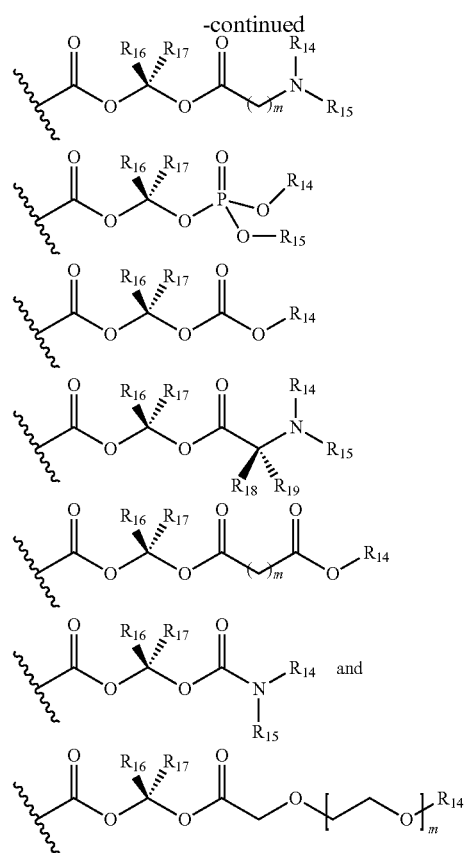

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, and polymorphs of the compounds of Formula I. In this Formula I, the Z, $R_1$, and $R_2$ groups are not linked to each other, in contrast to Formulae II, III, and IV described herein.

In one embodiment, $R_1$ is $P_2$ and $R_2$ is H. In another embodiment, $R_1$ is H and $R_2$ is $P_2$. In another embodiment, $R_1$ is $P_2$ and $R_2$ is $P_2$.

The group $P_2$ can be more particularly described. In one embodiment, $P_2$ is selected from the group consisting of:

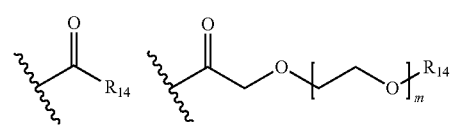

-continued
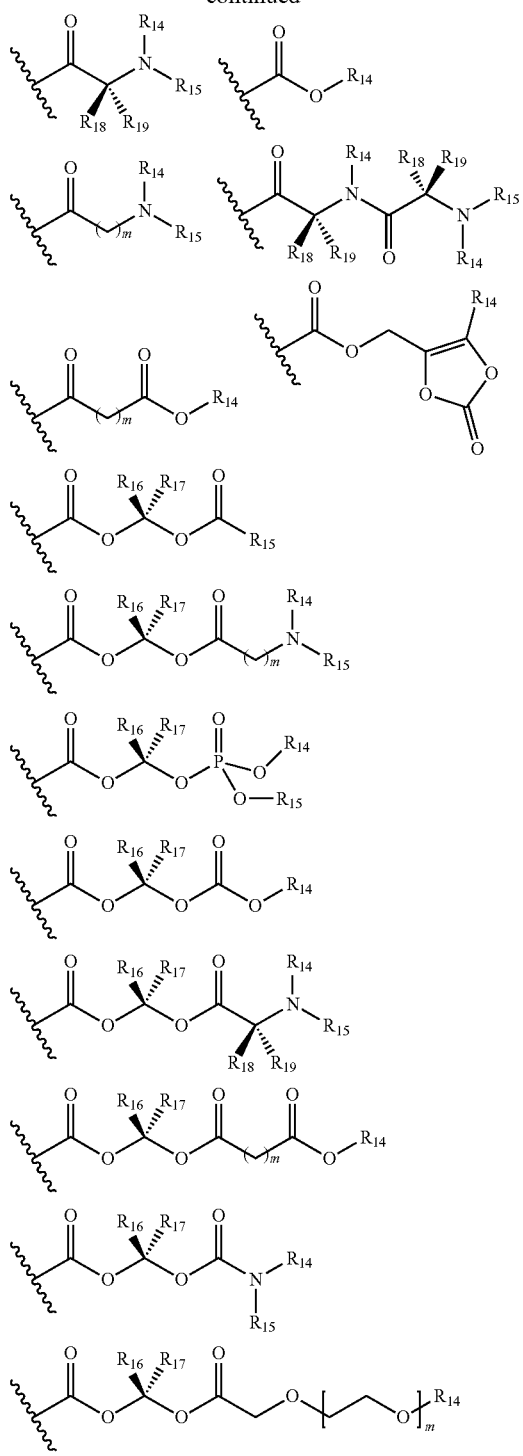
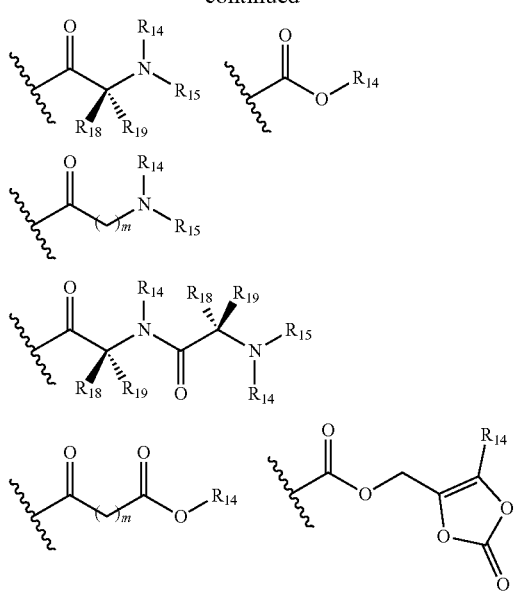
In another embodiment, P$_2$ is selected from the group consisting of:
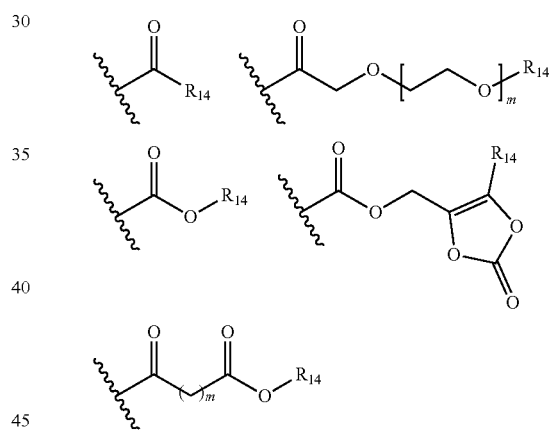
In another embodiment, P$_2$ is selected from the group consisting of:
In another embodiment, P$_2$ is selected from the group consisting of:
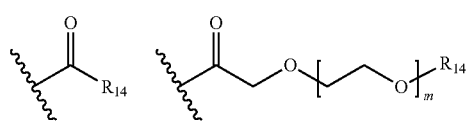
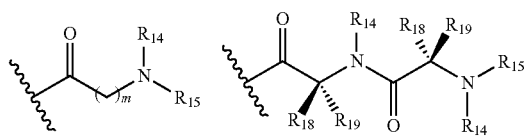
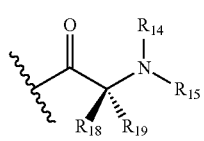

In another embodiment, $P_2$ is selected from the group consisting of:
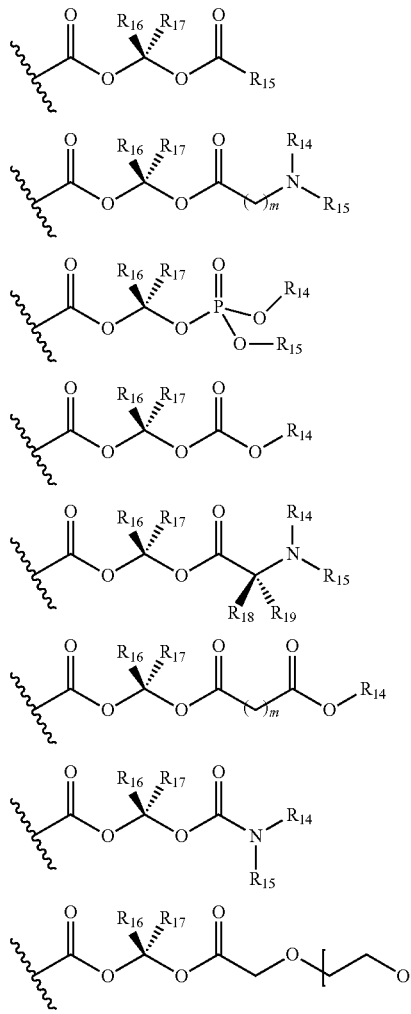
In another embodiment, $P_2$ is selected from the group consisting of:
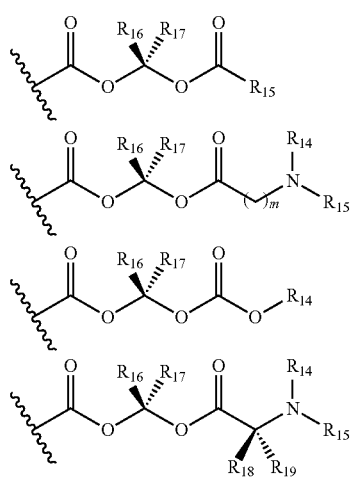
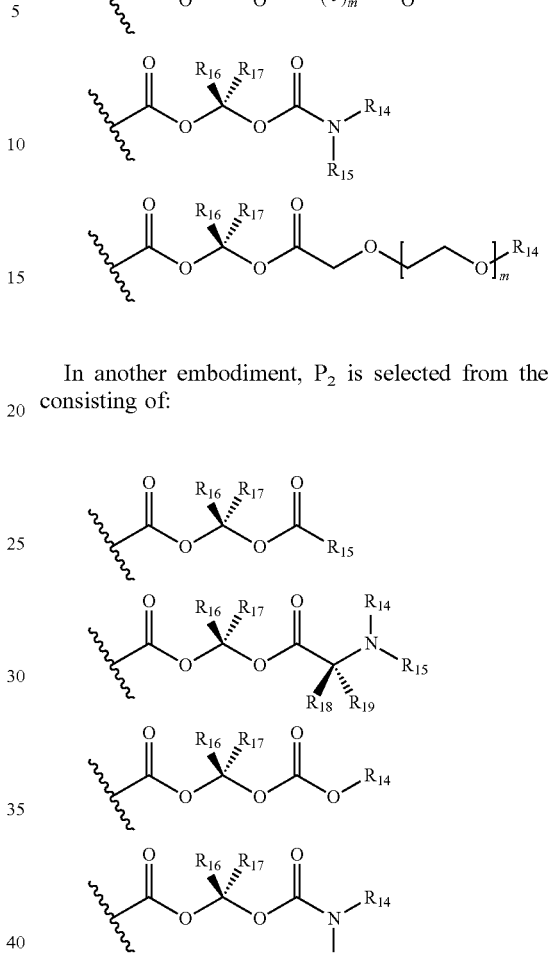
In another embodiment, $P_2$ is selected from the group consisting of:
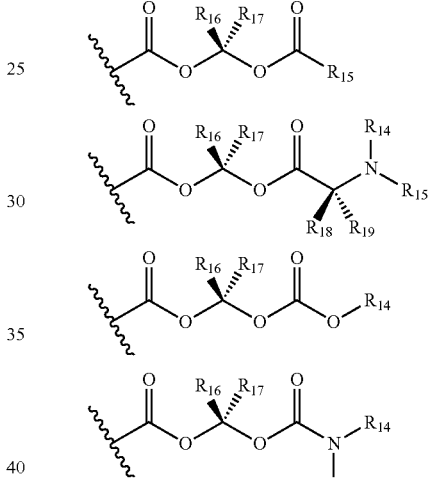
In another embodiment, $P_2$ is selected from the group consisting of:
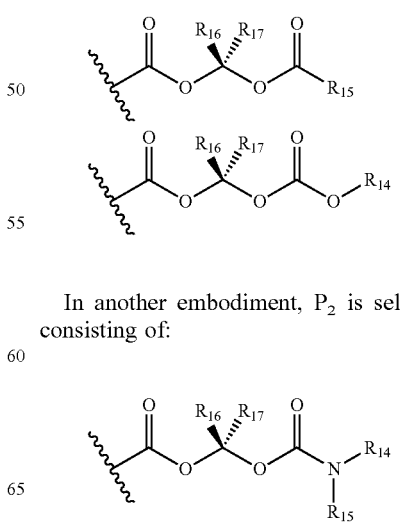

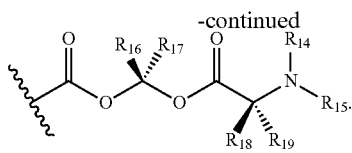

In another embodiment, P$_2$ is selected from the group consisting of:

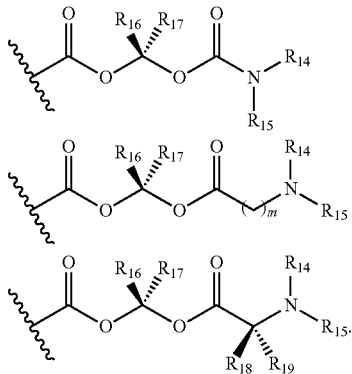

In another embodiment, P$_2$ is selected from the group consisting of:

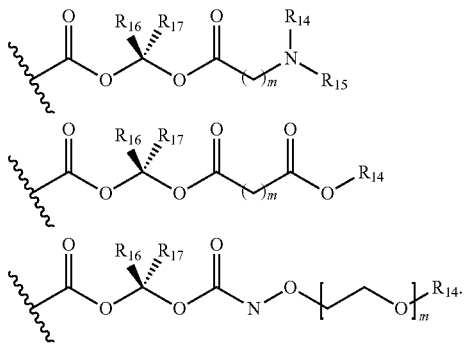

In one embodiment, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, and R$_{36}$ are H.

In one embodiment, Z is —OR$_{11}$, —N(R$_{11}$)R$_{12}$, or P$_1$. In another embodiment, Z is P$_1$. In another embodiment, Z is —OH, —OR$_{11}$, —N(R$_{11}$)R$_{12}$, or P$_1$. In another embodiment, Z is —OH.

In one embodiment, Z is not —OH and R$_{11}$ is not unsubstituted or substituted benzyl.

In a second sub-embodiment of Formula I,
R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, and R$_{36}$ are independently H or deuterium;
Z is —OR$_{11}$, —N(R$_{11}$)R$_{12}$, —SR$_{11}$, or P$_1$;
R$_{11}$ is branched alkyl, haloalkyl, halocycloalkyl, heteroalkyl, substituted heteroalkyl, cycloheteroalkyl, substituted cycloheteroalkyl, bicycloalkyl, alkylcycloalkyl, substituted alkylcycloalkyl, alkylcycloheteroalkyl, substituted alkylcycloheteroalkyl, alkylaryl, substituted alkylaryl, heteroaryl, substituted heteroaryl, alkylheteroaryl, substituted alkylheteroaryl;
R$_{12}$ is H, branched alkyl, haloalkyl, heteroalkyl, cycloheteroalkyl, alkylcycloalkyl, alkylcycloheteroalkyl, aryl, or heteroaryl;

P$_1$ is selected from the group consisting of:

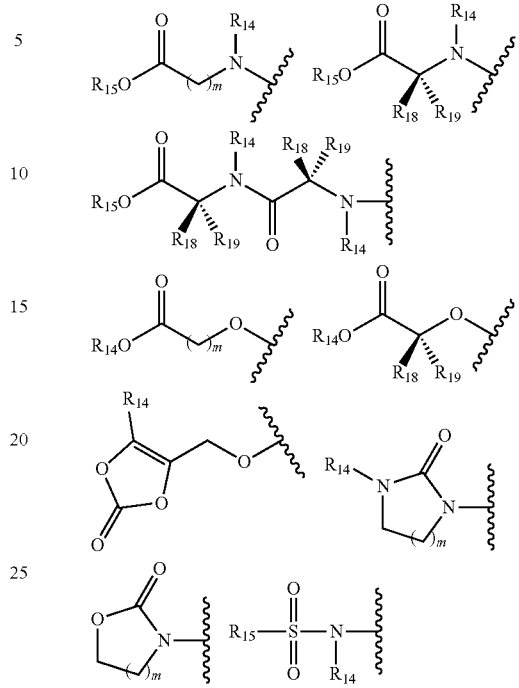

wherein, m is 1, 2, 3, or 4;

R$_{14}$ and R$_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

R$_{14}$ and R$_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

R$_{18}$ and R$_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the list consisting of alkyl, halo, haloalkyl, hydroxy, and alkoxy, haloalkoxy;

R$_{14}$ and R$_{18}$ taken together with the atoms to which they attach optionally form a 5- to 7-membered ring;

R$_{14}$ and R$_{19}$ taken together with the atoms to which they attach optionally form a 5- to 7-membered ring;

R$_{15}$ and R$_{18}$ taken together with the atoms to which they attach optionally form a 5- to 7-membered ring;

R$_{15}$ and R$_{19}$ taken together with the atoms to which they attach optionally form a 5- to 7-membered ring;

and, R$_1$ and R$_2$ are independently H or P$_2$, wherein $P_2$ is selected from the group consisting of:

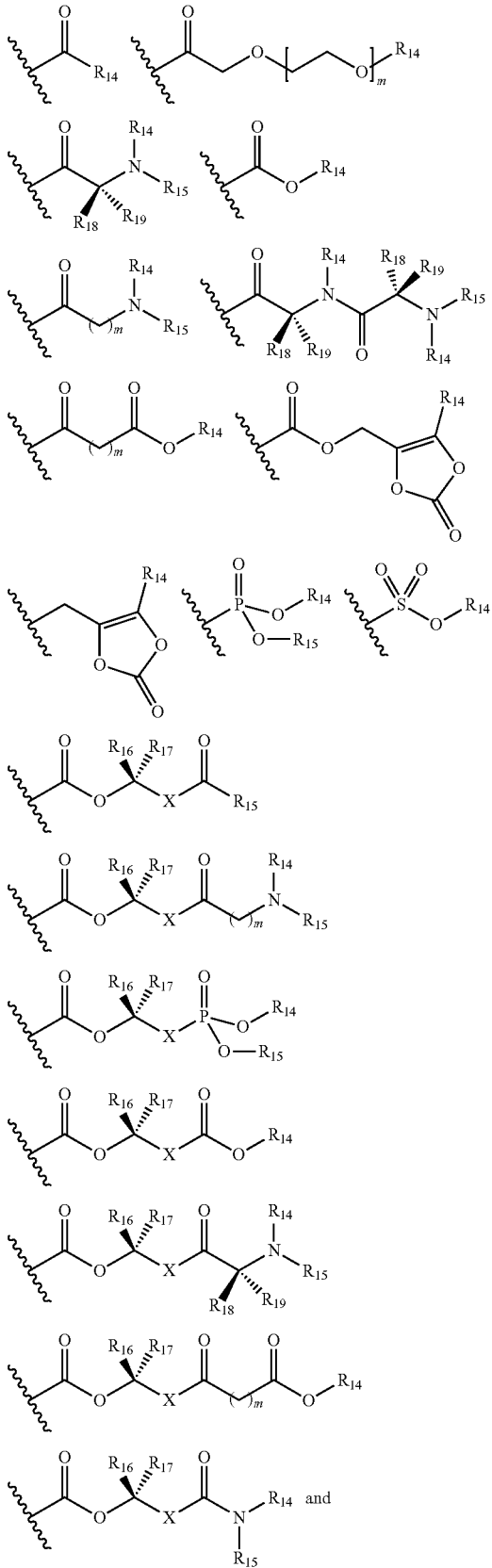

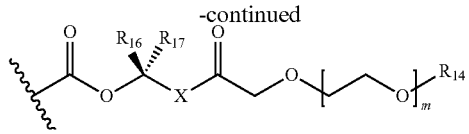

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, and polymorphs of the compounds of Formula I.

In one embodiment, Z is —$OR_{11}$. In one embodiment, Z is —$N(R_{11})R_{12}$. In one embodiment, Z is —$SR_{11}$. In one embodiment, Z is $P_1$. In one embodiment, Z is $OR_{11}$ and $R_{11}$ is bicycloalkyl, alkylcycloalkyl, or alkylcycloheteroalkyl. In one embodiment, Z is $P_1$.

In one embodiment, $R_{11}$ is haloalkyl, or more particularly, fluoroalkyl.

In one embodiment, $R_1$ is hydrogen or $R_2$ is hydrogen. In one embodiment, $R_1$ is hydrogen and $R_2$ is $P_2$. In one embodiment, $R_1$ is $P_2$ and $R_2$ is hydrogen. In one embodiment, $R_1$ and $R_2$ are hydrogen. In one embodiment, $R_1$ and $R_2$ are $P_2$.

In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are deuterium.

In one embodiment, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are hydrogen.

Formula IA

One particular sub-embodiment also for formula I is a compound represented by Formula (IA):

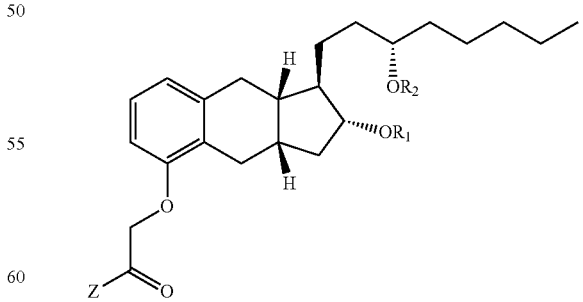

wherein,

Z is —OH, —$OR_1$, or $P_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, P₁ is selected from the group consisting of:

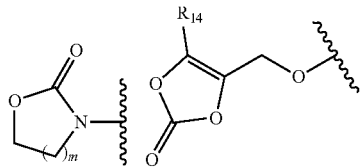

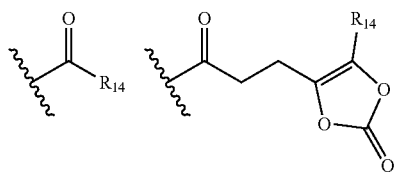

wherein, m is 1, 2, 3, or 4;

R$_{14}$ is selected from the group consisting of H, alkyl, cycloalkyl, alkylcycloalkyl, haloalkyl, aryl, heteroaryl, arylalkyl, heteroarylalkyl, substituted aryl, substituted heteroaryl, substituted arylalkyl, and substituted heteroarylalkyl;

and, R₁ and R₂ are independently H or P₂, wherein at least one of R₁ and R₂ is P₂, wherein P₂ is selected from the group consisting of:

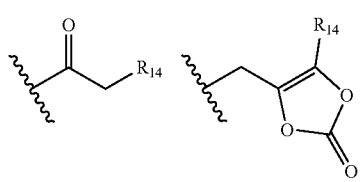

wherein,

R$_{14}$ and R$_{15}$ are independently in each occurrence selected from the group consisting of H, alkyl, cycloalkyl, alkylcycloalkyl, haloalkyl, aryl, heteroaryl, arylalkyl, heteroarylalkyl, substituted aryl, substituted heteroaryl, substituted arylalkyl, and substituted heteroarylalkyl;

R$_{14}$ and R$_{15}$ taken together with the atoms to which they attach optionally form a 5- to 7-membered ring;

wherein Formula IA includes enantiomers, pharmaceutically acceptable salts, and polymorphs of the compounds of Formula IA.

Specific Compounds for Formula I

The following are specific compounds for formula I (noting Compound A which as discussed hereinabove is the control, not a pro-drug):

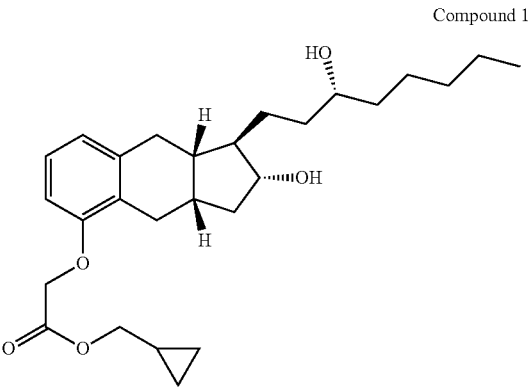 [SMILES: CCCCC[C@@H](O)CC[C@@H]1[C@H]2Cc3cccc(OCC(=O)OCC4CC4)c3C[C@H]2C[C@H]1O]

[2-Hydroxy-1-(3-hydroxy-octyl)-2,3,3a,4,9,9a-hexahydro-1H-cyclopenta[b]naphthalen-5-yloxy]-acetic acid cyclopropylmethyl ester

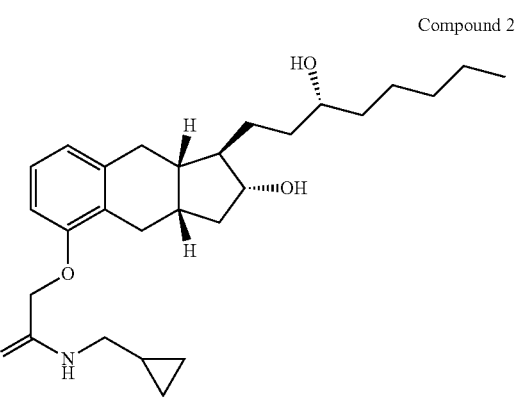

N-Cyclopropylmethyl-2-[2-hydroxy-1-(3-hydroxy-octyl)-2,3,3a,4,9,9a-hexahydro-1H-cyclopenta[b]naphthalen-5-yloxy]-acetamide

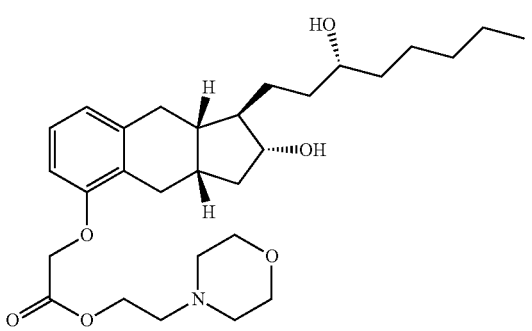

[2-Hydroxy-1-(3-hydroxy-octyl)-2,3,3a,4,9,9a-hexahydro-1H-cyclopenta[b]naphthalen-5-yloxy]-acetic acid 2-morpholin-4-yl-ethyl ester

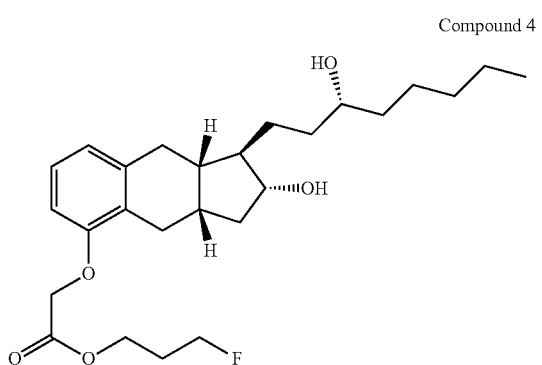 [SMILES: CCCCC[C@@H](O)CC[C@@H]1[C@H]2Cc3cccc(OCC(=O)OCCCF)c3C[C@H]2C[C@H]1O]

Compound 4

[2-Hydroxy-1-(3-hydroxy-octyl)-2,3,3a,4,9,9a-hexahydro-1H-cyclopenta[b]naphthalen-5-yloxy]-acetic acid 3-fluoro-propyl ester

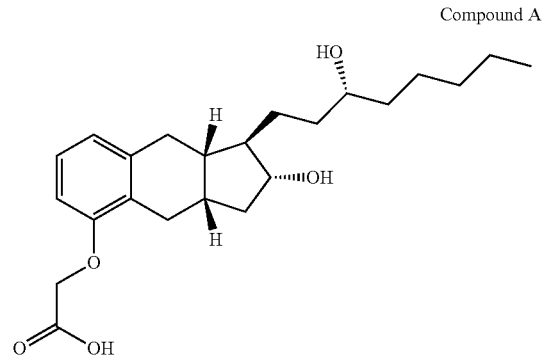 [SMILES: CCCCC[C@@H](O)CC[C@@H]1[C@H]2Cc3cccc(OCC(=O)O)c3C[C@H]2C[C@H]1O]

Compound A

[2-Hydroxy-1-(3-hydroxy-octyl)-2,3,3a,4,9,9a-hexahydro-1H-cyclopenta[b]naphthalen-5-yloxy]-acetic acid

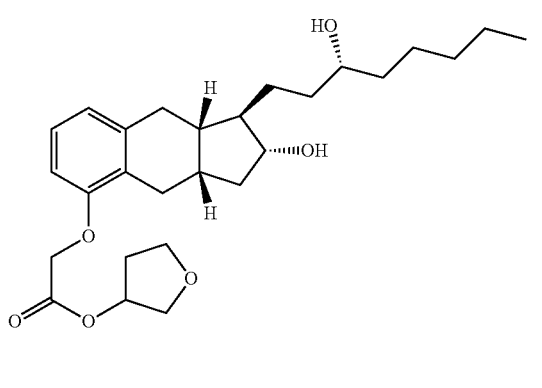

Compound 5

[2-Hydroxy-1-(3-hydroxy-octyl)-2,3,3a,4,9,9a-hexahydro-1H-cyclopenta[b]naphthalen-5-yloxy]-acetic acid tetrahydro-furan-3-yl ester

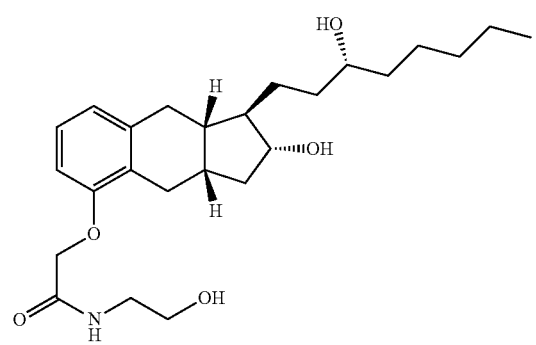

Compound 7

N-(2-Hydroxy-ethyl)-2-[2-hydroxy-1-(3-hydroxy-octyl)-2,3,3a,4,9,9a-hexahydro-1H-cyclopenta[b]naphthalen-5-yloxy]-acetamide

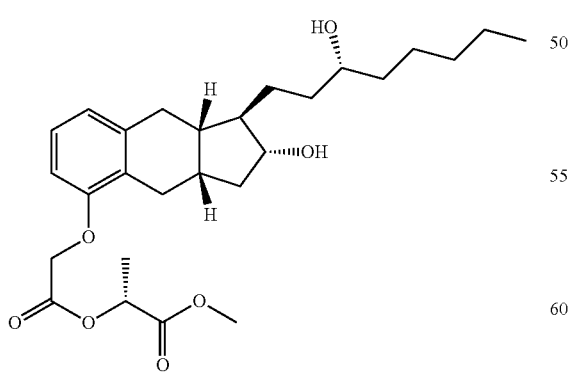

Compound 6

2-{2-[2-Hydroxy-1-(3-hydroxy-octyl)-2,3,3a,4,9,9a-hexahydro-1H-cyclopenta[b]naphthalen-5-yloxy]-acetoxy}-propionic acid methyl ester

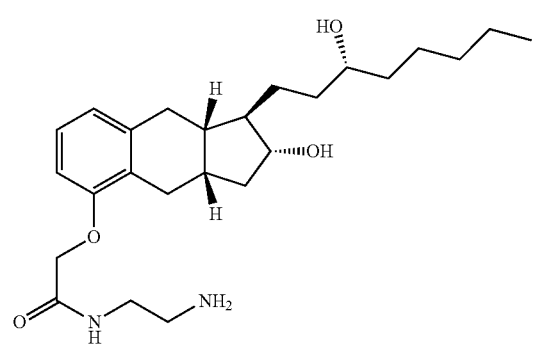

Compound 8

N-(2-Amino-ethyl)-2-[2-hydroxy-1-(3-hydroxy-octyl)-2,3,3a,4,9,9a-hexahydro-1H-cyclopenta[b]naphthalen-5-yloxy]-acetamide

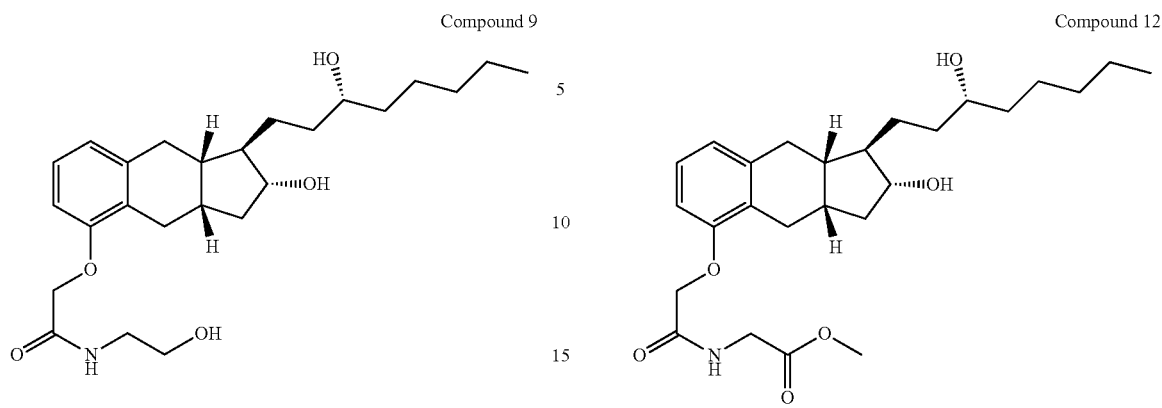

Compound 9

[2-Hydroxy-1-(3-hydroxy-octyl)-2,3,3a,4,9,9a-hexahydro-1H-cyclopenta[b]naphthalen-5-yloxy]-acetic acid 2-hydroxy-ethyl ester Compound 12

{2-[2-Hydroxy-1-(3-hydroxy-octyl)-2,3,3a,4,9,9a-hexahydro-1H-cyclopenta[b]naphthalen-5-yloxy]-acetylamino}-acetic acid methyl ester

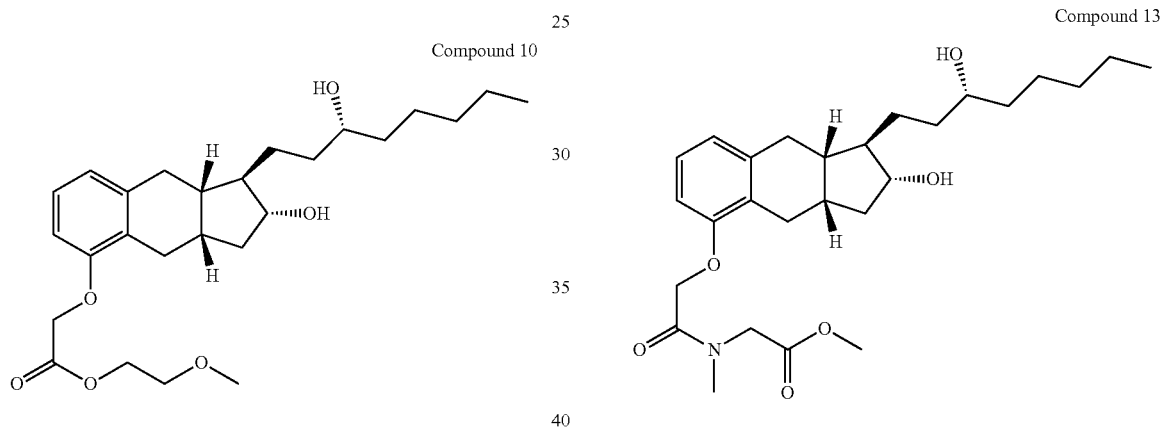

Compound 10

[2-Hydroxy-1-(3-hydroxy-octyl)-2,3,3a,4,9,9a-hexahydro-1H-cyclopenta[b]naphthalen-5-yloxy]-acetic acid 2-methoxy-ethyl ester Compound 13

({2-[2-Hydroxy-1-(3-hydroxy-octyl)-2,3,3a,4,9,9a-hexahydro-1H-cyclopenta[b]naphthalen-5-yloxy]-acetyl}-methyl-amino)-acetic acid methyl ester

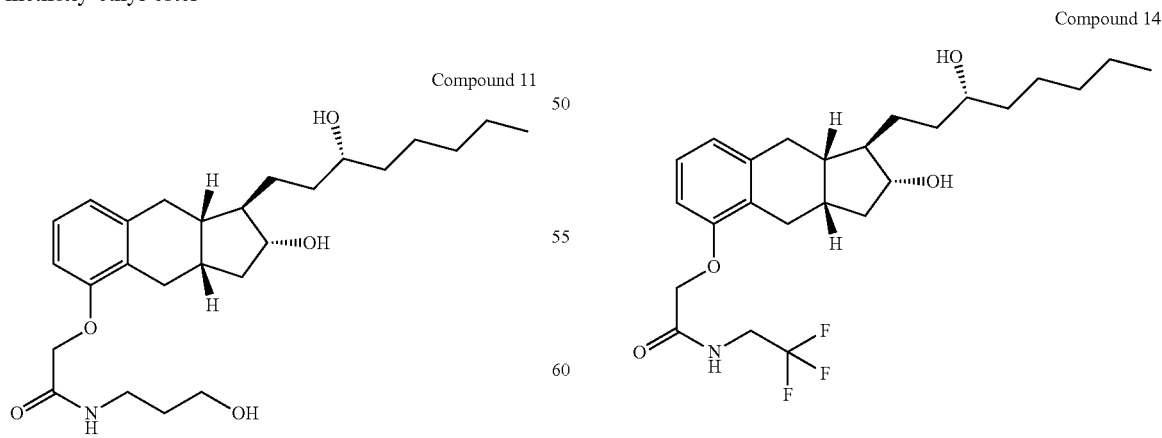

Compound 11

2-[2-Hydroxy-1-(3-hydroxy-octyl)-2,3,3a,4,9,9a-hexahydro-1H-cyclopenta[b]naphthalen-5-yloxy]-N-(3-hydroxy-propyl)-acetamide Compound 14

2-[2-Hydroxy-1-(3-hydroxy-octyl)-2,3,3a,4,9,9a-hexahydro-1H-cyclopenta[b]naphthalen-5-yloxy]-N-(2,2,2-trifluoro-ethyl)-acetamide Compound 15

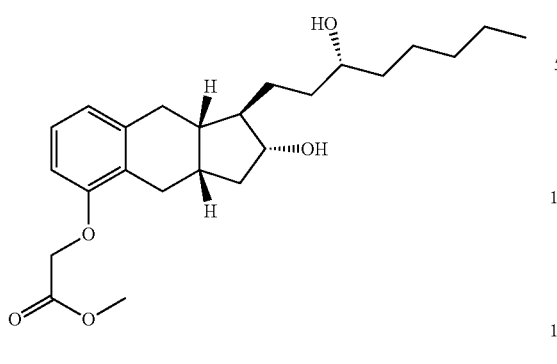

[2-Hydroxy-1-(3-hydroxy-octyl)-2,3,3a,4,9,9a-hexahydro-1H-cyclopenta[b]naphthalen-5-yloxy]-acetic acid methyl ester Compound 16

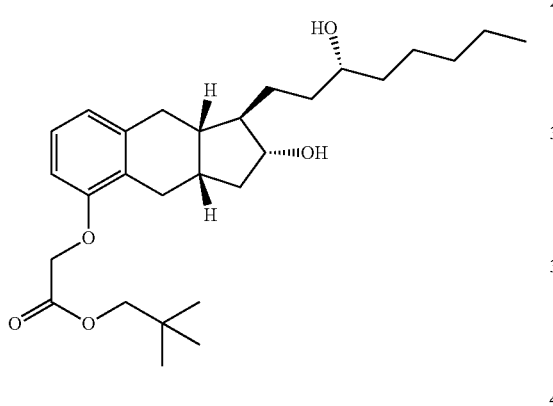

[2-Hydroxy-1-(3-hydroxy-octyl)-2,3,3a,4,9,9a-hexahydro-1H-cyclopenta[b]naphthalen-5-yloxy]-acetic acid 2,2-dimethyl-propyl ester Compound 17

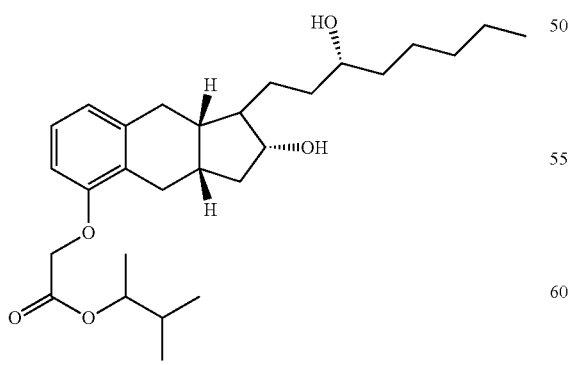

[2-Hydroxy-1-(3-hydroxy-octyl)-2,3,3a,4,9,9a-hexahydro-1H-cyclopenta[b]naphthalen-5-yloxy]-acetic acid 1,2-dimethyl-propyl ester Compound 18

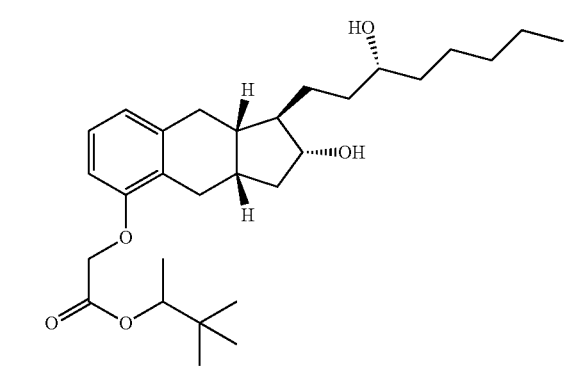

[2-Hydroxy-1-(3-hydroxy-octyl)-2,3,3a,4,9,9a-hexahydro-1H-cyclopenta[b]naphthalen-5-yloxy]-acetic acid 1,2,2-trimethyl-propyl ester Compound 19

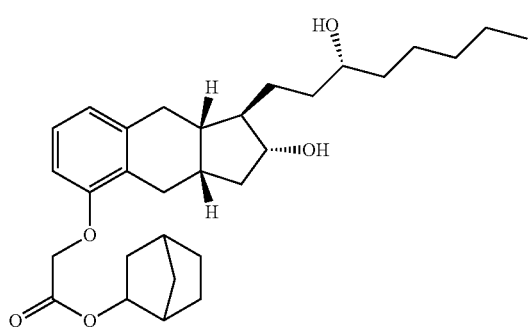

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester Compound 20

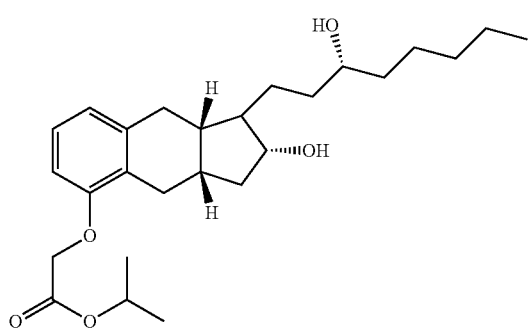

[2-Hydroxy-1-(3-hydroxy-octyl)-2,3,3a,4,9,9a-hexahydro-1H-cyclopenta[b]naphthalen-5-yloxy]-acetic acid isopropyl ester

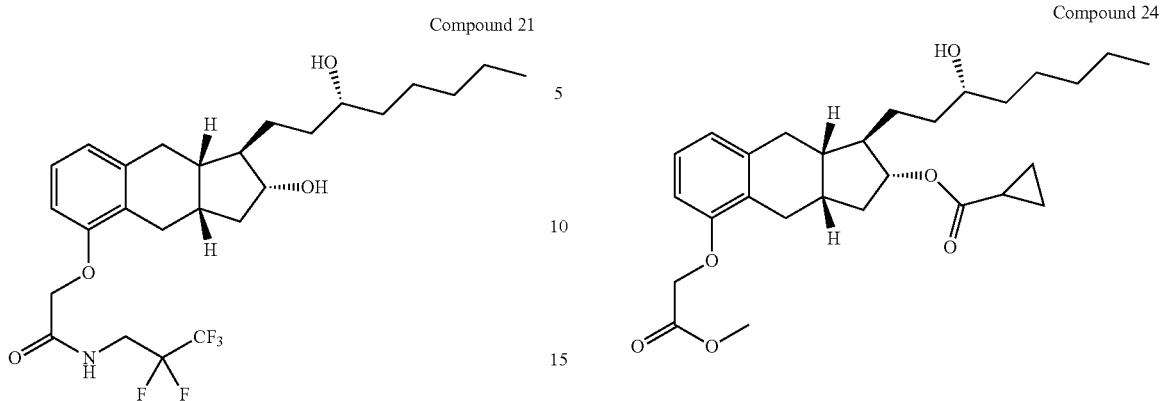

2-[2-Hydroxy-1-(3-hydroxy-octyl)-2,3,3a,4,9,9a-hexa-hydro-1H-cyclopenta[b]naphthalen-5-yloxy]-N-(2,2,3,3-pentafluoro-propyl)-acetamide Cyclopropanecarboxylic acid 1-(3-hydroxy-octyl)-5-methoxycarbonylmethoxy-2,3,3a,4,9,9a-hexahydro-1H-cyclopenta[b]naphthalen-2-yl ester

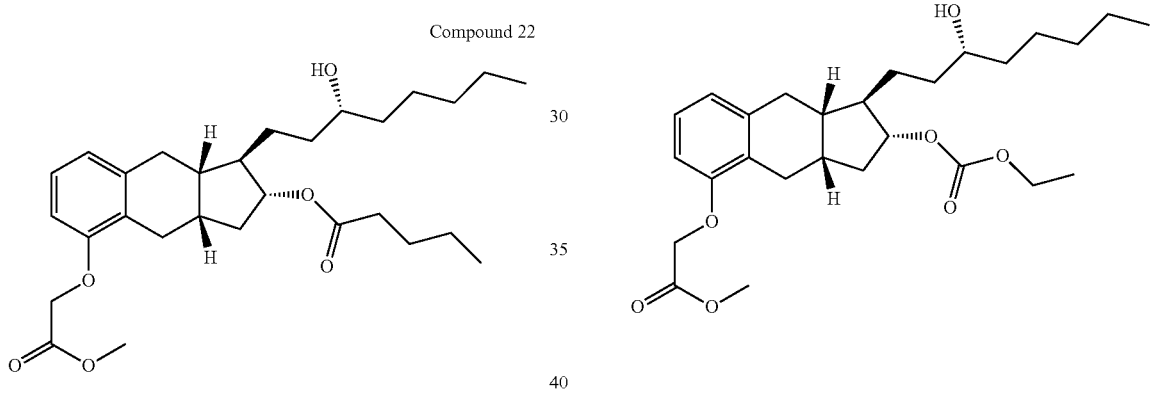

Pentanoic acid 1-(3-hydroxy-octyl)-5-methoxycarbonyl-methoxy-2,3,3a,4,9,9a-hexahydro-1H-cyclopenta[b]naphthalen-2-yl ester

[2-Ethoxycarbonyloxy-1-(3-hydroxy-octyl)-2,3,3a,4,9,9a-hexahydro-1H-cyclopenta[b]naphthalen-5-yloxy]-acetic acid methyl ester

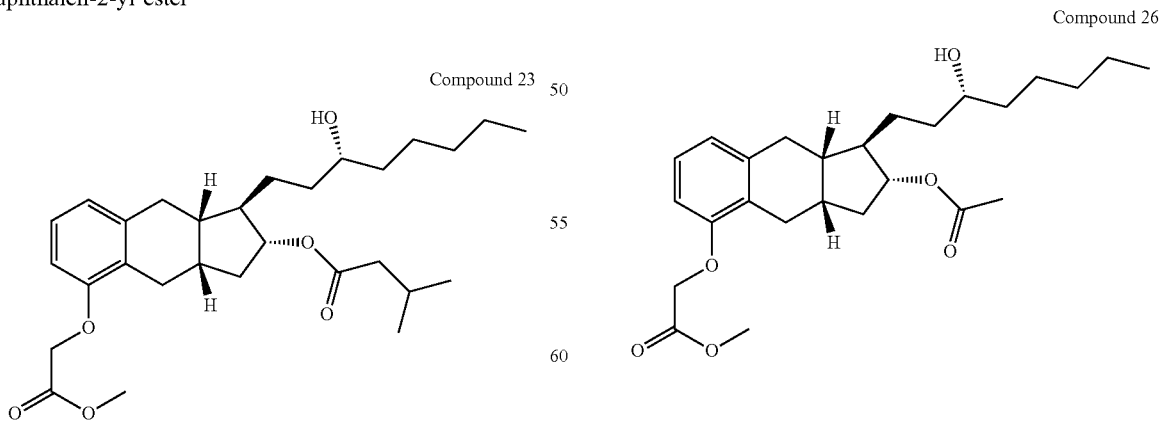

3-Methyl-butyric acid 1-(3-hydroxy-octyl)-5-methoxycar-bonylmethoxy-2,3,3a,4,9,9a hexahydro-1H-cyclopenta[b]naphthalen-2-yl ester

[2-Acetoxy-1-(3-hydroxy-octyl)-2,3,3a,4,9,9a-hexahydro-1H-cyclopenta[b]naphthalen-5-yloxy]-acetic acid methyl ester

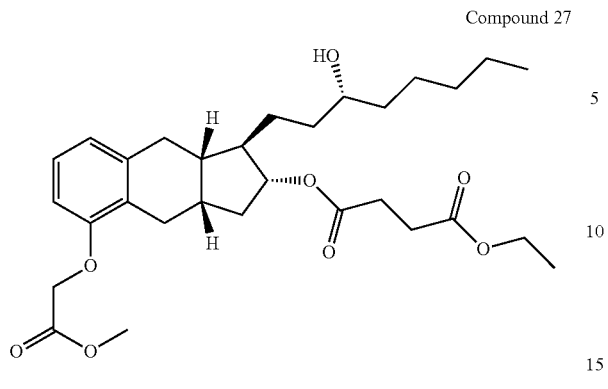

Compound 27

Succinic acid ethyl ester 1-(3-hydroxy-octyl)-5-methoxycarbonylmethoxy-2,3,3a,4,9,9a-hexahydro-1H-cyclopenta[b]naphthalen-2-yl ester

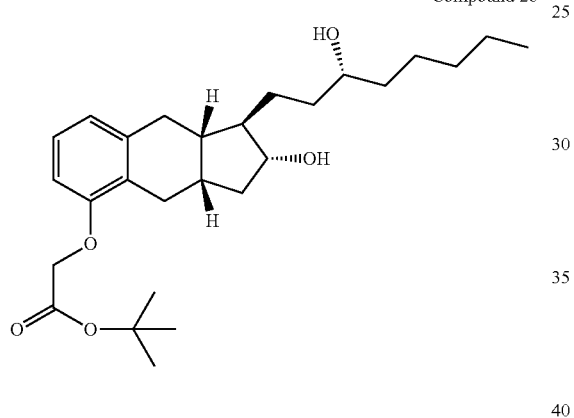

Compound 28

[2-Hydroxy-1-(3-hydroxy-octyl)-2,3,3a,4,9,9a-hexahydro-1H-cyclopenta[b]naphthalen-5-yloxy]-acetic acid tert-butyl ester

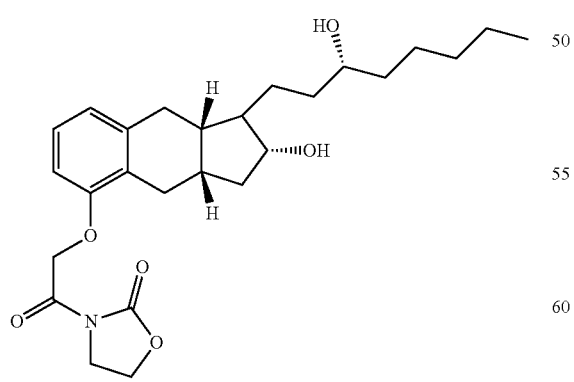

Compound 29

3-{2-[2-Hydroxy-1-(3-hydroxy-octyl)-2,3,3a,4,9,9a-hexahydro-1H-cyclopenta[b]naphthalen-5-yloxy]-acetyl}-oxazolidin-2-one

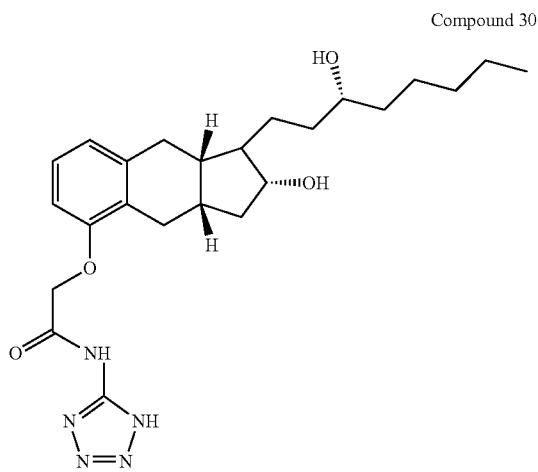 [SMILES: CCCCC[C@@H](O)CCC1[C@H](O)C[C@@H]2Cc3c(cccc3OCC(=O)Nc3nnn[nH]3)C[C@H]12]

Compound 30

2-[2-Hydroxy-1-(3-hydroxy-octyl)-2,3,3a,4,9,9a-hexahydro-1H-cyclopenta[b]naphthalen-5-yloxy]-N-(1H-tetrazol-5-yl)-acetamide

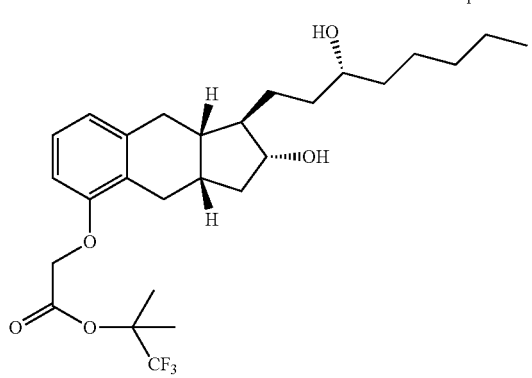

Compound 31

[2-Hydroxy-1-(3-hydroxy-octyl)-2,3,3a,4,9,9a-hexahydro-1H-cyclopenta[b]naphthalen-5-yloxy]-acetic acid 2,2,2-trifluoro-1,1-dimethyl-ethyl ester Compound 32

[2-Hydroxy-1-(3-hydroxy-octyl)-2,3,3a,4,9,9a-hexahydro-1H-cyclopenta[b]naphthalen-5-yloxy]-acetic acid 1,2,2-trimethyl-propyl ester Compound 33

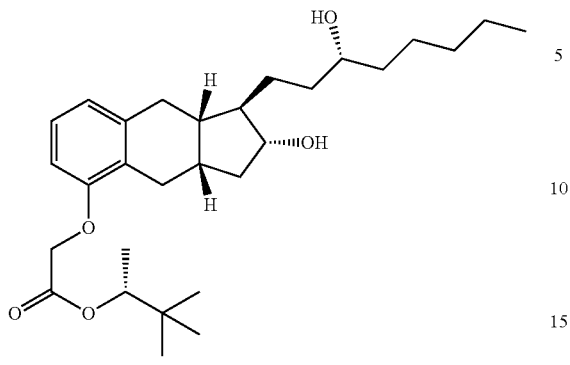

[2-Hydroxy-1-(3-hydroxy-octyl)-2,3,3a,4,9,9a-hexahydro-1H-cyclopenta[b]naphthalen-5-yloxy]-acetic acid 1,2,2-trimethyl-propyl ester Compound 36

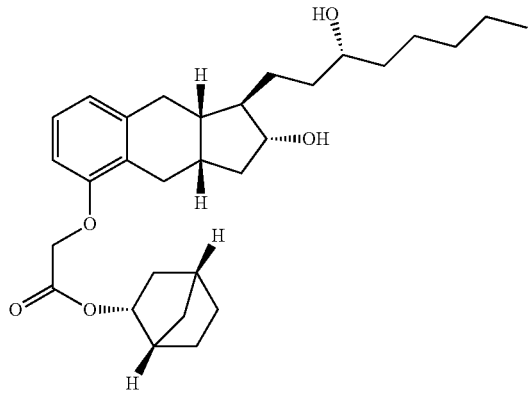

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester Compound 34

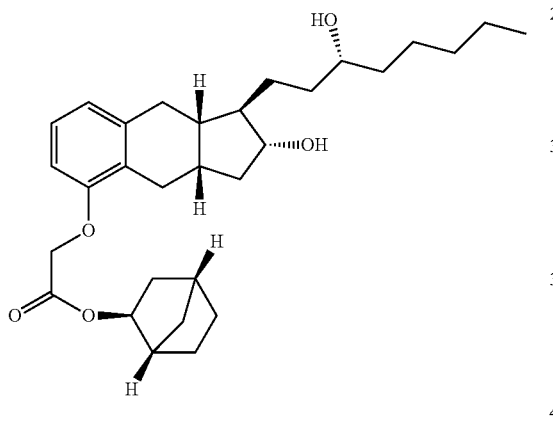

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester Compound 37

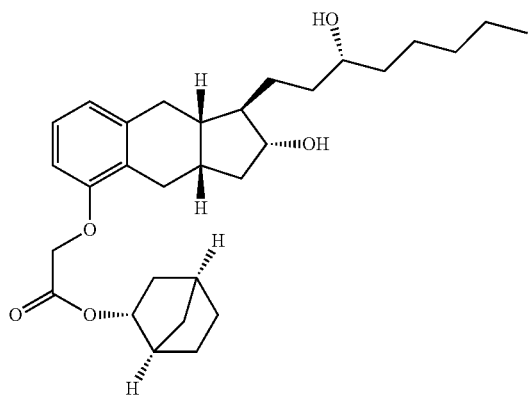

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester Compound 35

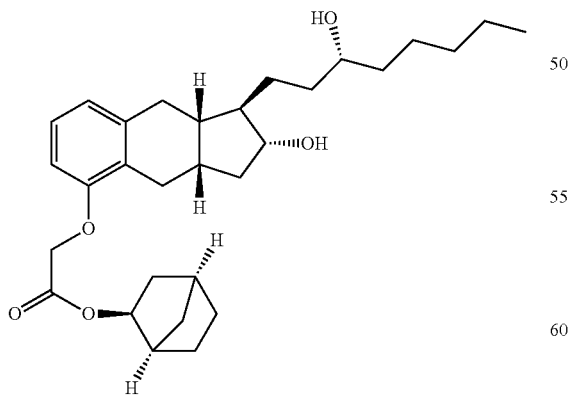

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester Compound 38

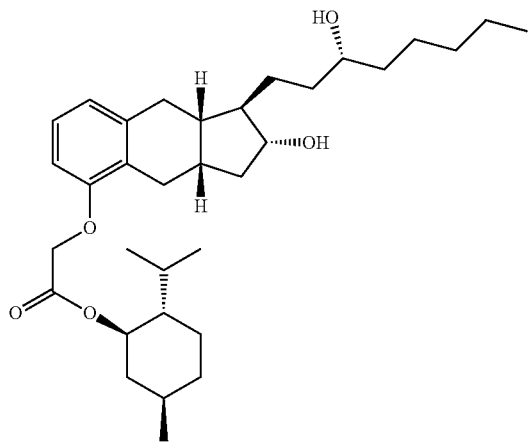

[2-Hydroxy-1-(3-hydroxy-octyl)-2,3,3a,4,9,9a-hexahydro-1H-cyclopenta[b]naphthalen-5-yloxy]-acetic acid 2-isopropyl-5-methyl-cyclohexyl ester Compound 39

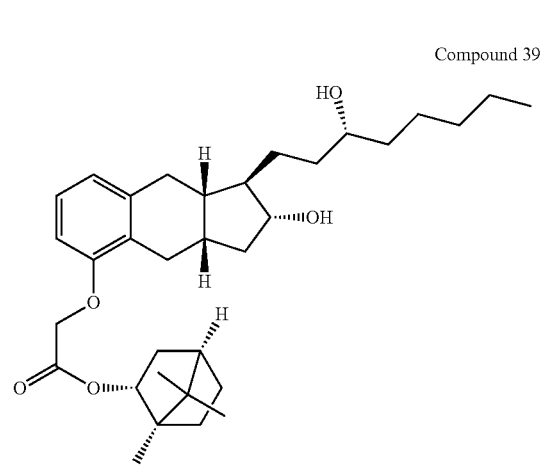 [SMILES: CCCCC[C@@H](O)CC[C@@H]1[C@H]2Cc3cccc(OCC(=O)O[C@@H]4C[C@H]5CC[C@]4(C)C5(C)C)c3C[C@H]2C[C@H]1O]

[2-Hydroxy-1-(3-hydroxy-octyl)-2,3,3a,4,9,9a-hexahydro-1H-cyclopenta[b]naphthalen-5-yloxy]-acetic acid 1,7,7-trimethyl-bicyclo[2.2.1]hept-2-yl ester Compound 40

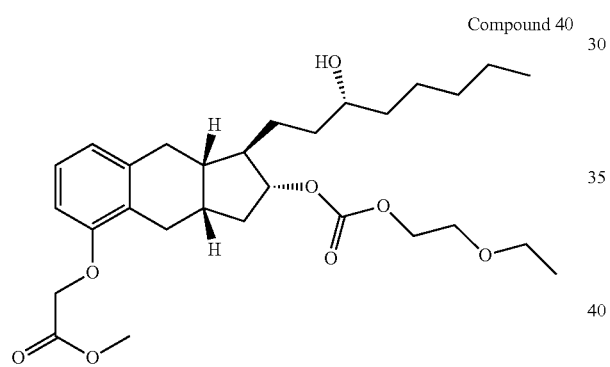

[2-(2-Ethoxy-ethoxycarbonyloxy)-1-(3-hydroxy-octyl)-2,3,3a,4,9,9a-hexahydro-1H-cyclopenta[b]naphthalen-5-yloxy]-acetic acid methyl ester Compound 41

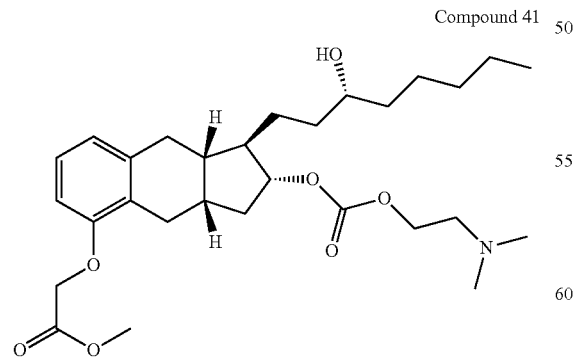 [SMILES: CCCCC[C@@H](O)CC[C@@H]1[C@H]2Cc3cccc(OCC(=O)OC)c3C[C@H]2C[C@H]1OC(=O)OCCOCC]

[2-(2-Dimethylamino-ethoxycarbonyloxy)-1-(3-hydroxy-octyl)-2,3,3a,4,9,9a-hexahydro-1H-cyclopenta[b]naphthalen-5-yloxy]-acetic acid methyl ester Compound 42

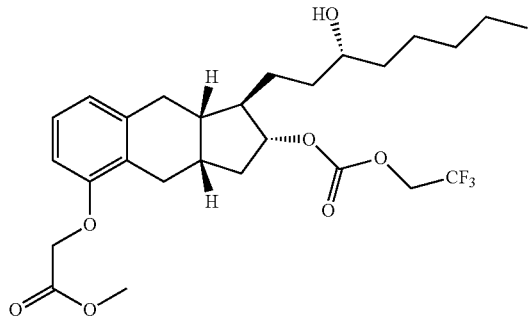

[1-(3-Hydroxy-octyl)-2-(2,2,2-trifluoro-ethoxycarbonyloxy)-2,3,3a,4,9,9a-hexahydro-1H-cyclopenta[b]naphthalen-5-yloxy]-acetic acid methyl ester Compound 43

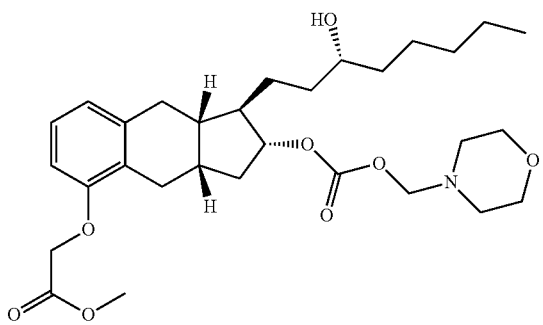

3-Morpholin-4-yl-propionic acid 1-(3-hydroxy-octyl)-5-methoxycarbonylmethoxy-2,3,3a,4,9,9a-hexahydro-1H-cyclopenta[b]naphthalen-2-yl ester Compound 44

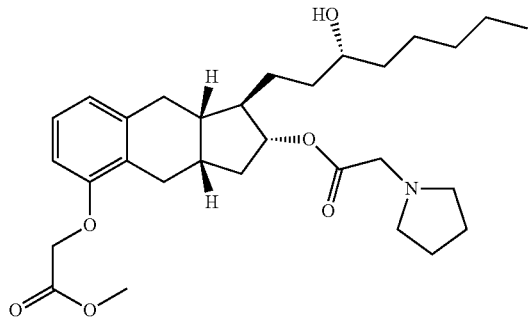

[1-(3-Hydroxy-octyl)-2-(2-pyrrolidin-1-yl-acetoxy)-2,3,3a,4,9,9a-hexahydro-1H-cyclopenta[b]naphthalen-5-yloxy]-acetic acid methyl ester

45

Compound 45

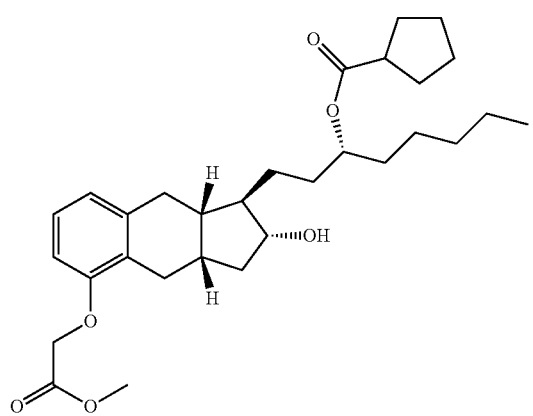

Cyclopentanecarboxylic acid 1-[2-(2-hydroxy-5-methoxy-carbonylmethoxy-2,3,3a,4,9,9a-hexahydro-1H-cyclopenta[b]naphthalen-1-yl)-ethyl]-hexyl ester

Compound 46

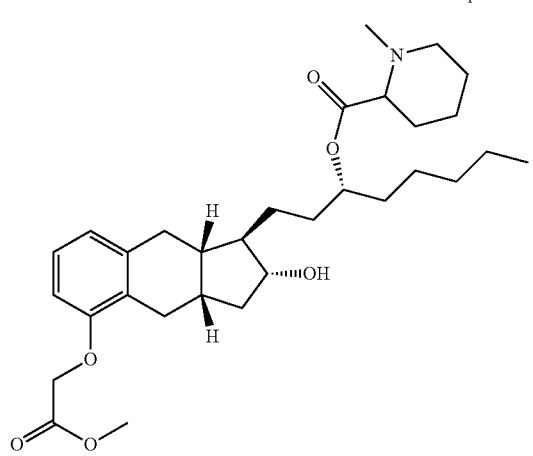

1-Methyl-piperidine-2-carboxylic acid 1-[2-(2-hydroxy-5-methoxycarbonylmethoxy-2,3,3a,4,9,9a-hexahydro-1H-cyclopenta[b]naphthalen-1-yl)-ethyl]-hexyl ester

Compound 47

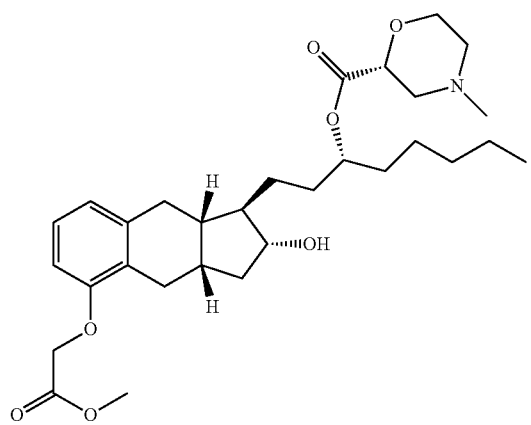

46

4-Methyl-morpholine-2-carboxylic acid 1-[2-(2-hydroxy-5-methoxycarbonylmethoxy-2,3,3a,4,9,9a-hexahydro-1H-cyclopenta[b]naphthalen-1-yl)-ethyl]-hexyl ester

Compound 48

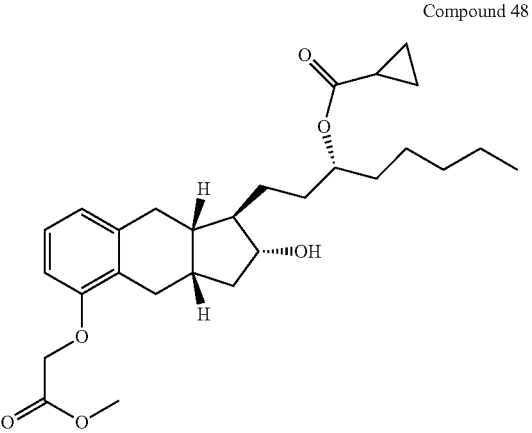 [SMILES: CCCCC[C@H](CC[C@@H]1[C@H]2Cc3cccc(OCC(=O)OC)c3C[C@H]2C[C@H]1O)OC(=O)C1CC1]

Cyclopropanecarboxylic acid 1-[2-(2-hydroxy-5-methoxycarbonylmethoxy-2,3,3a,4,9,9a-hexahydro-1H-cyclopenta[b]naphthalen-1-yl)-ethyl]-hexyl ester

Compound 49

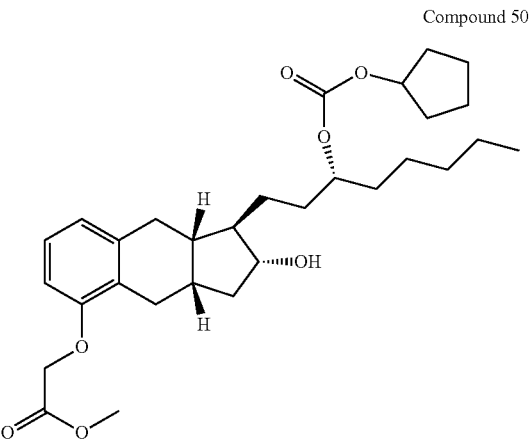 [SMILES: CCCCC[C@H](CC[C@@H]1[C@H]2Cc3cccc(OCC(=O)OC)c3C[C@H]2C[C@H]1O)OC(=O)OC1CCCC1]

2-Methyl-butyric acid 1-[2-(2-hydroxy-5-methoxycarbonylmethoxy-2,3,3a,4,9,9a-hexahydro-1H-cyclopenta[b]naphthalen-1-yl)-ethyl]-hexyl ester

Compound 50

[1-(3-Cyclopentyloxycarbonyloxy-octyl)-2-hydroxy-2,3,3a, 4,9,9a-hexahydro-1H-cyclopenta[b]naphthalen-5-yloxy]-acetic acid methyl ester

[2-Hydroxy-1-(3-hydroxy-octyl)-2,3,3a,4,9,9a-hexahydro-1H-cyclopenta[b]naphthalen-5-yloxy]-acetic acid 1-aza-bicyclo[2.2.2]oct-3-yl ester Compound 51

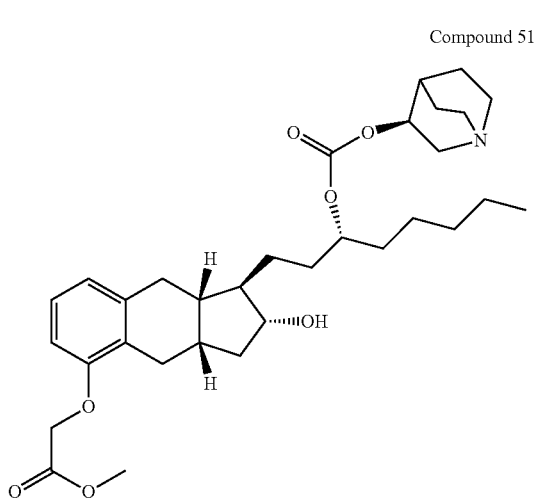 [SMILES: CCCCC[C@H](CC[C@@H]1[C@H]2Cc3cccc(OCC(=O)OC)c3C[C@H]2C[C@H]1O)OC(=O)O[C@@H]1CN2CCC1CC2]

{1-[3-(1-Aza-bicyclo[2.2.2]oct-3-yloxycarbonyloxy)-octyl]-2-hydroxy-2,3,3a,4,9,9a-hexahydro-1H-cyclopenta[b]naphthalen-5-yloxy}-acetic acid methyl ester Compound 54

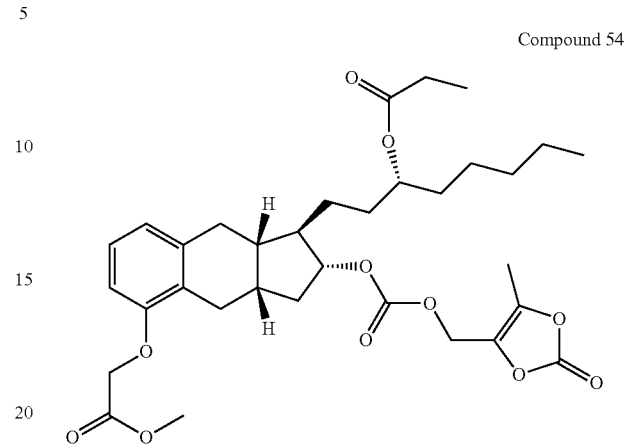

Propionic acid 1-{2-[5-methoxycarbonylmethoxy-2-(5-methyl-2-oxo-[1,3]dioxol-4-ylmethoxycarbonyloxy)-2,3,3a,4,9,9a-hexahydro-1H-cyclopenta[b]naphthalen-1-yl]-ethyl}-hexyl ester Compound 52

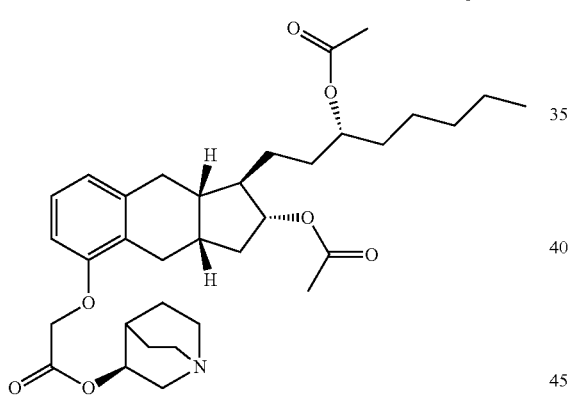

[2-Acetoxy-1-(3-acetoxy-octyl)-2,3,3a,4,9,9a-hexahydro-1H-cyclopenta[b]naphthalen-5-yloxy]-acetic acid 1-aza-bicyclo[2.2.2]oct-3-yl ester Compound 55

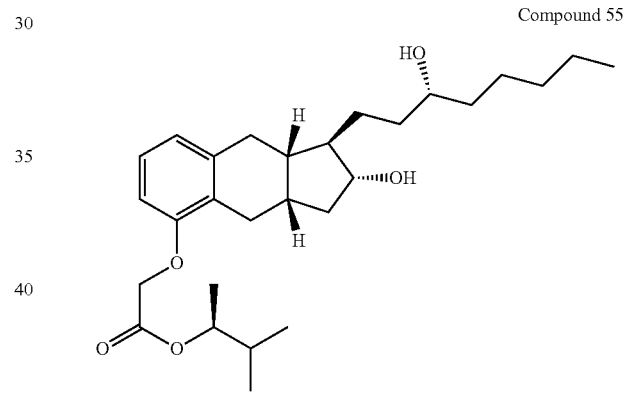

[2-Hydroxy-1-(3-hydroxy-octyl)-2,3,3a,4,9,9a-hexahydro-1H-cyclopenta[b]naphthalen-5-yloxy]-acetic acid 1,2-dimethyl-propyl ester Compound 53

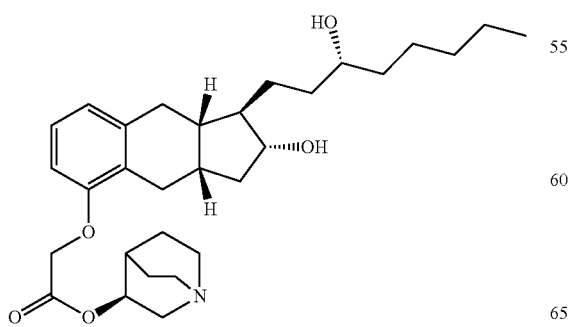

Compound 56

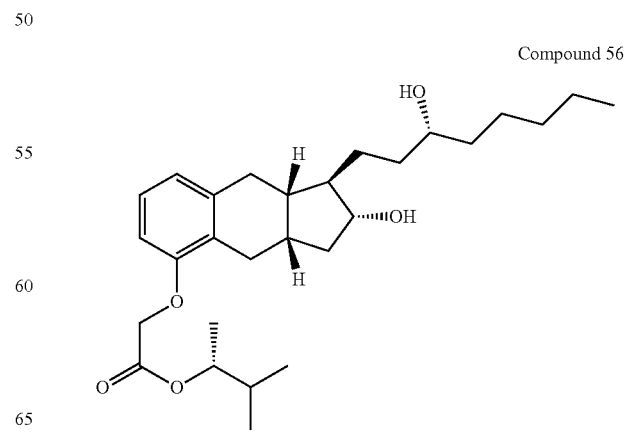

[2-Hydroxy-1-(3-hydroxy-octyl)-2,3,3a,4,9,9a-hexahydro-1H-cyclopenta[b]naphthalen-5-yloxy]-acetic acid 1,2-dimethyl-propyl ester Core Structure Formulae II and IIA In another embodiment, the present invention provides a compound represented by Formula II:

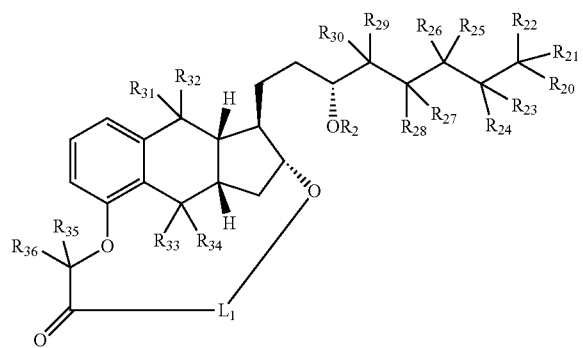

wherein, $R_2$ is selected from the group consisting of H and $P_2$;

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H, deuterium;

$L_1$ is a selected from the group consisting of —O-alkylene-C(O)—, —O-alkylene-OC(O)—, or a bond; wherein $P_2$ is selected from the group consisting of:

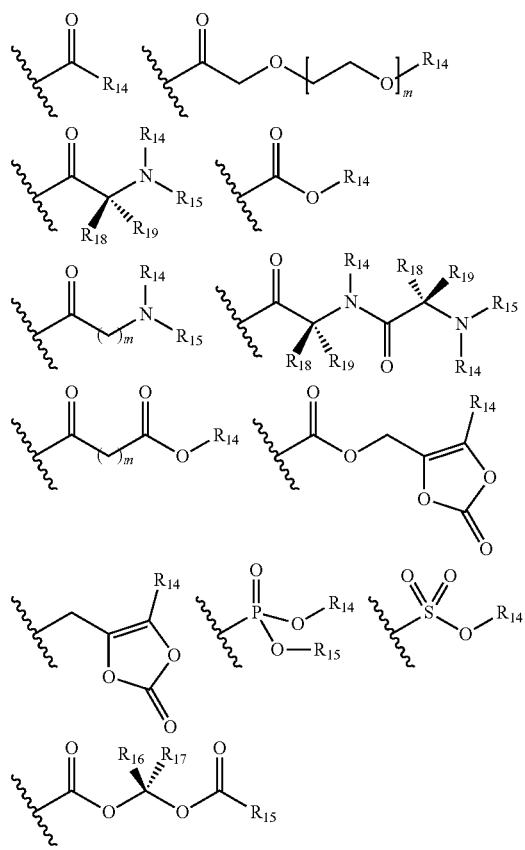

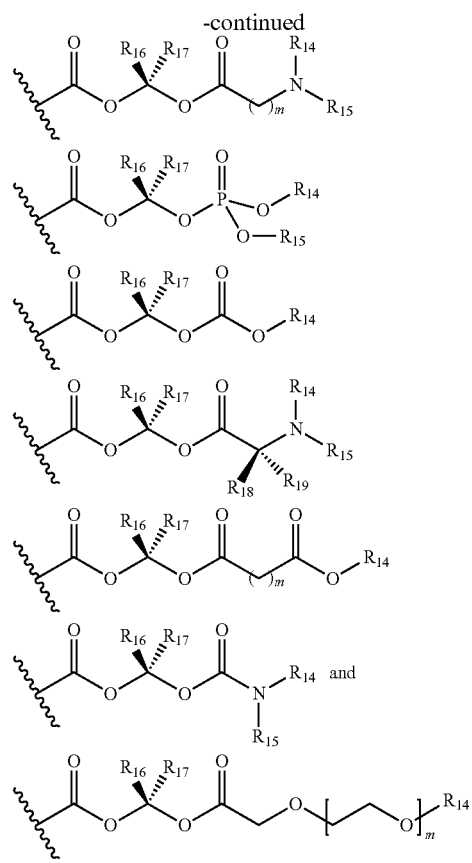

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula II includes enantiomers, pharmaceutically acceptable salts, and polymorphs of the compounds of Formula II.

In one embodiment, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are H. In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are deuterium.

In one embodiment, $L_1$ is selected from the group consisting of —O-alkyl-C(O)—, —O-alkyl-OC(O)—. In one embodiment, $L_1$ is —O-alkylene-C(O)—. In one embodiment, $L_1$ is —O-alkylene-OC(O)—. In one embodiment, the alkylene group is a C1-C5 alkylene group. In one embodiment, the alkylene group is a C1 alkylene group.

In one sub-embodiment for Formula II, provided is a compound, wherein the compound is represented by Formula IIA:

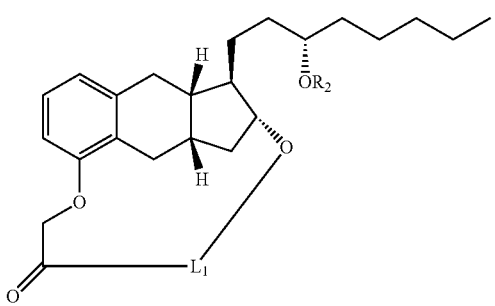

wherein $L_1$ and $R_2$ are defined as in Formula II.

Specific Compounds According to Formula II

The following represent specific compounds of Formula II:

Compound 57

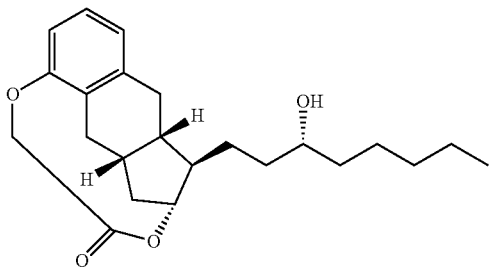

Treprostinil 2-hydroxy lactone

Compound 58

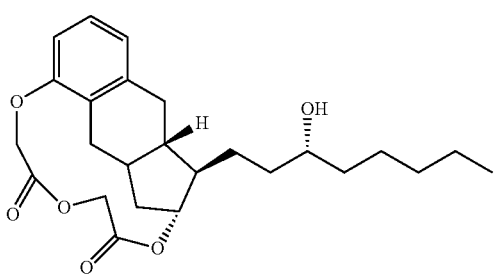

[2-Hydroxy-1-(3-hydroxy-octyl)-2,3,3a,4,9,9a-hexahydro-1H-cyclopenta[b]naphthalen-5-yloxy]-acetic acid carboxymethyl lactone Core Structure Formula III In one other embodiment, the present invention also provides a compound represented by Formula III:

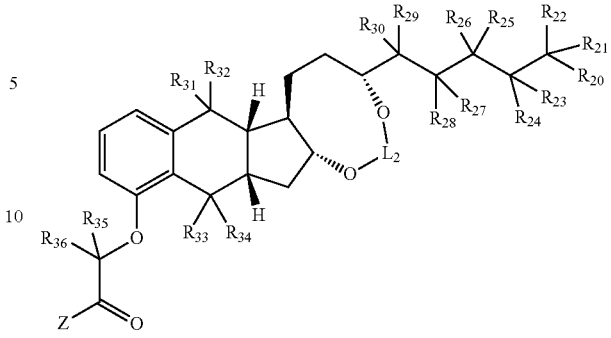

wherein $L_2$ is selected from the group consisting of:

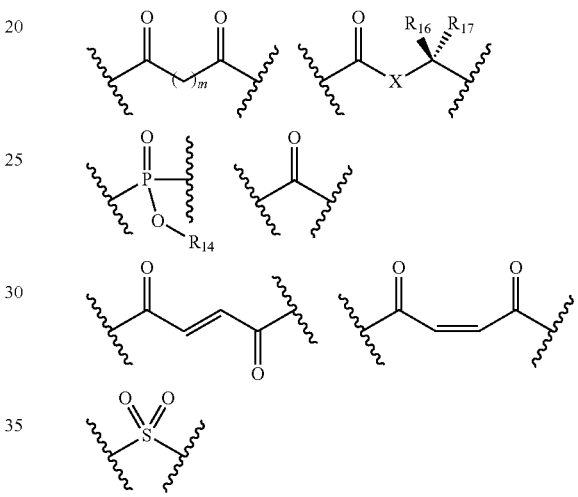

wherein, m is 1, 2, 3, or 4;

X is $NR_{14}$, or O;

$R_{14}$ is selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, substituted heteroarylalkyl;

$R_{16}$ and $R_{17}$ are independently in each occurrence H or alkyl;

$R_{16}$ and $R_{17}$ taken together with the atoms to which they attach optionally form a 3- to 6-membered ring; and $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H, deuterium;

wherein Z is —OH, —$OR_{11}$, —$N(R_{11})R_{12}$, —$SR_{11}$, or $P_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from the group consisting of:

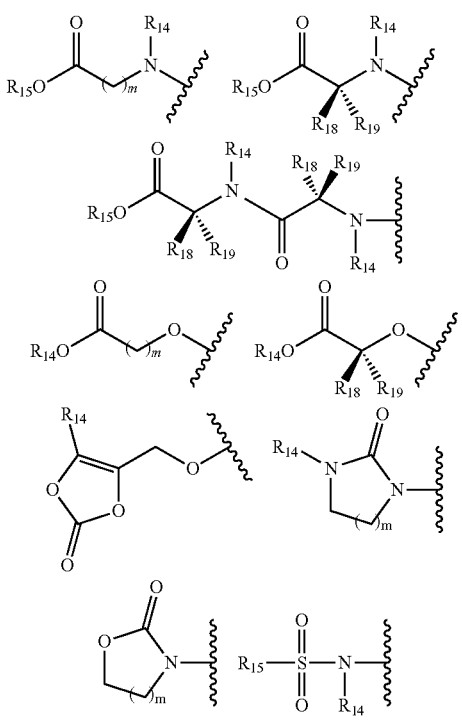

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the list consisting of alkyl, halo, haloalkyl, hydroxy, and alkoxy, haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

wherein Formula III includes enantiomers, pharmaceutically acceptable salts, and polymorphs of the compounds of Formula III.

In one embodiment, $L_2$ is selected from the group consisting of:

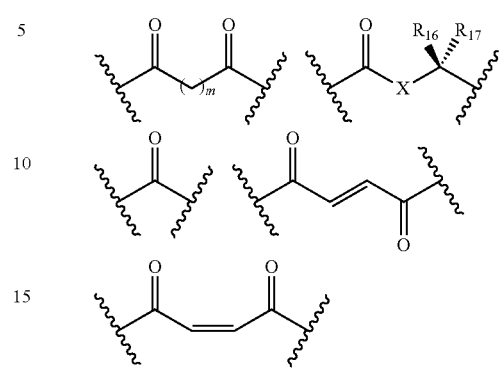

In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are deuterium, or they are all hydrogen.

One particular sub-embodiment of Formula III includes a compound represented by Formula IIIA:

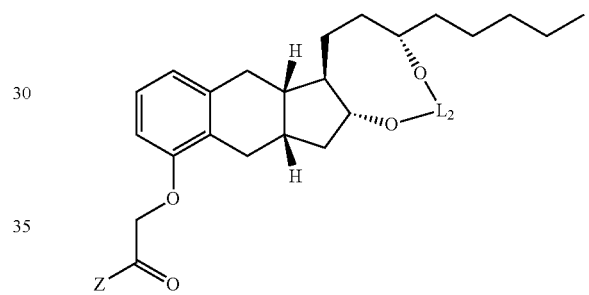

wherein Z and $L_2$ are defined as in Formula III.

Specific Examples of Formula III Compounds

The following compounds represent specific examples of Formula III compounds:

Compound 59

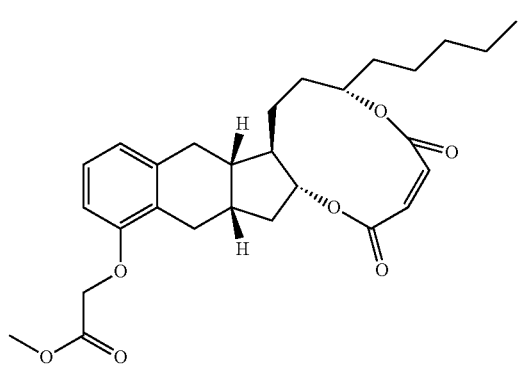

[2-Hydroxy-1-(3-hydroxy-octyl)-2,3,3a,4,9,9a-hexahydro-1H-cyclopenta[b]naphthalen-5-yloxy]-acetic acid methyl ester 2,3-maleate

Core Structure for Formula IV Compounds

Another embodiment is a compound represented by Formula IV, wherein unlike in Formula II, the $L_1$ group links to $R_2$ rather than $R_1$:

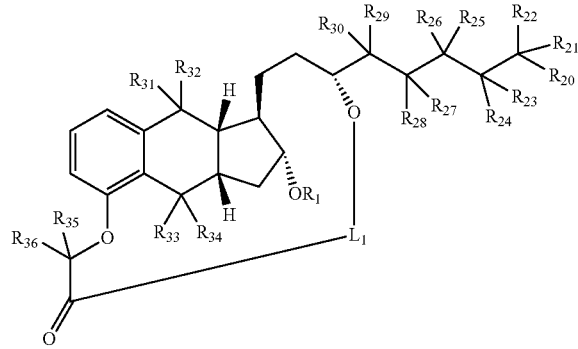

$R_1$ is selected from the group consisting of H and $P_2$;
$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;
$L_1$ is a selected from the group consisting of —O-alkylene-C(O)—, —O-alkylene-OC(O)—, or a bond; wherein $P_2$ is selected from the group consisting of:

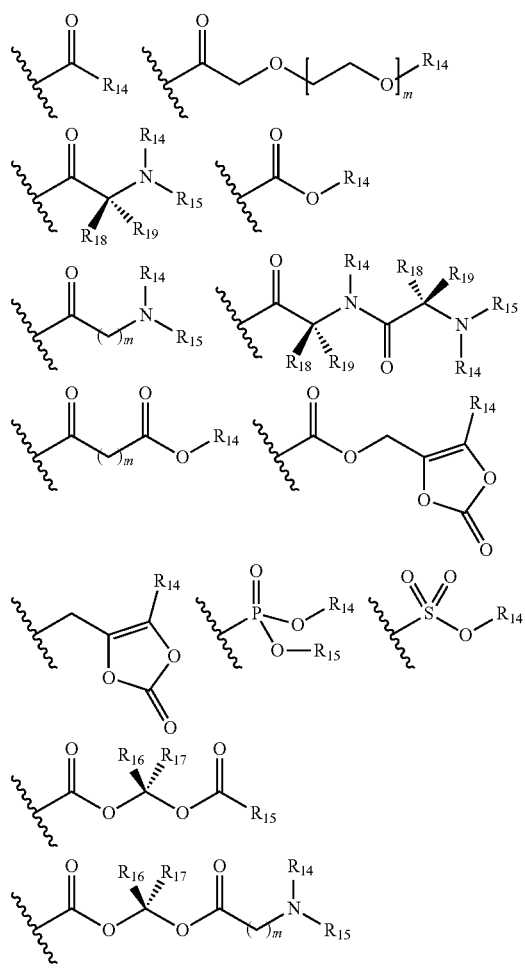

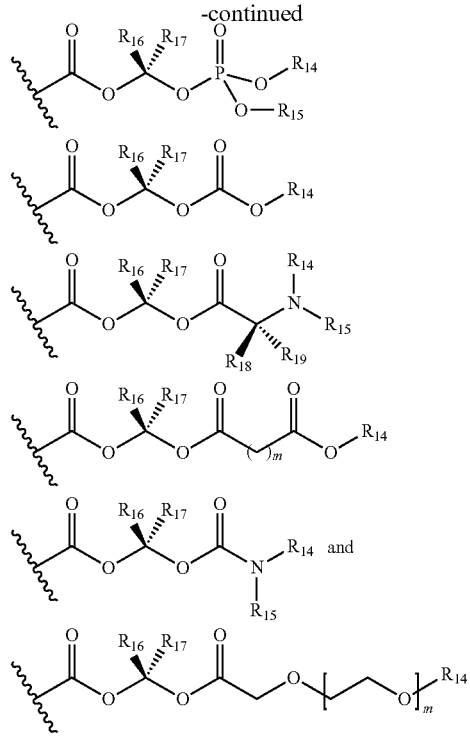

wherein,
m is 1, 2, 3, or 4;
$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;
$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;
$R_{16}$ and $R_{17}$ are independently in each occurrence H or alkyl;
$R_{16}$ and $R_{17}$ taken together with the atoms to which they attach optionally form a 3- to 6-membered ring;
$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the list consisting of alkyl, halo, haloalkyl, hydroxy, and alkoxy, haloalkoxy;
$R_{14}$ and $R_{18}$ taken together with the atoms to which they attach optionally form a 5- to 7-membered ring;
$R_{14}$ and $R_{19}$ taken together with the atoms to which they attach optionally form a 5- to 7-membered ring;
wherein Formula IV includes enantiomers, pharmaceutically acceptable salts, and polymorphs of the compounds of Formula IV.

In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are deuterium, or they are all hydrogen.

In a particular embodiment of Formula IV, a compound is represented by Formula IVA:

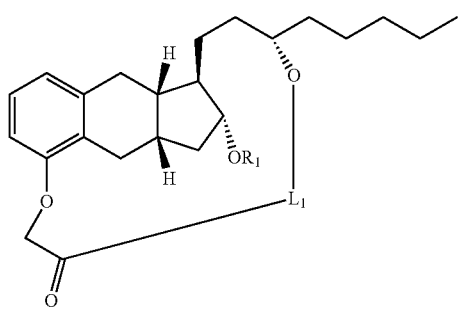

wherein $L_1$ and $R_1$ are defined as in Formula IV.

Similar approaches can be used to make and use Formula IV compounds as for Formula II compounds.

Embodiments from Priority Provisional 61/751,608

One embodiment from the priority provisional is a compound according to Formula (IAA).

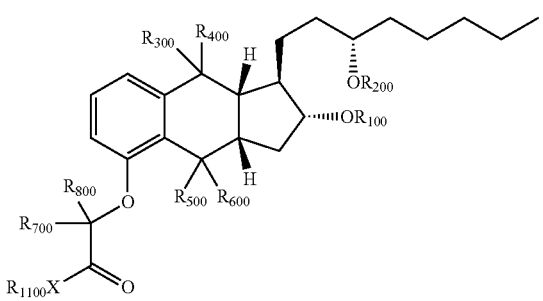

wherein,
$R_{100}$ and $R_{200}$ are independently selected from the group consisting of H, $CONR_{900}R_{1000}$, $CR_{900}R_{1000}OCOP_3R_{900}R_{1000}$ wherein, $R_{900}$ and $R_{1000}$ are independently selected from H, alkyl, and cycloalkyl.

$R_{300}$, $R_{400}$, $R_{500}$, $R_{600}$, $R_{700}$ and $R_{800}$ is independently selected from the group consisting of H and deuterium.

X is O, $NHR_{1200}$, or S $P_3$ is N or O $R_{1100}$ is haloalkyl, heteroalkyl, cycloheteroalkyl, alkylcycloalkyl, alkylcycloheteroalkyl, aryl, heteroaryl;

$R_{1200}$ is haloalkyl, heteroalkyl, cycloheteroalkyl, alkylcycloalkyl, alkylcycloheteroalkyl, aryl, heteroaryl.

In one embodiment, $R_{100}$, $R_{200}$ are H. In one embodiment, $R_{300}$, $R_{400}$, $R_{500}$, $R_{600}$, $R_{700}$ and $R_{800}$ are H. In one embodiment, X is O. In one embodiment, $R_{1100}$ is selected from

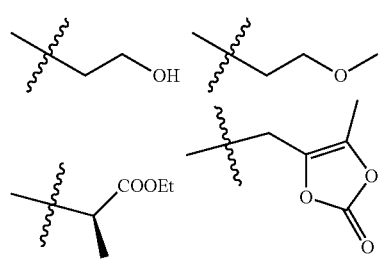

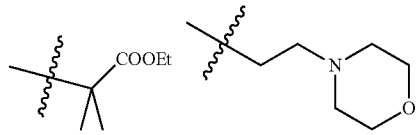

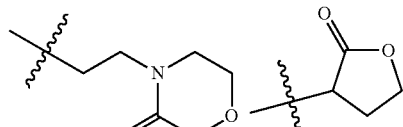

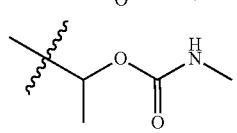

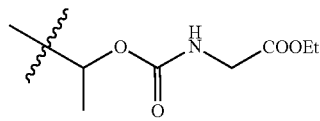

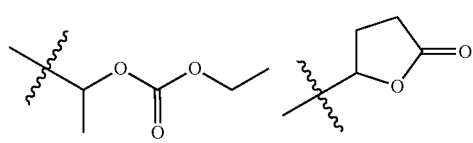

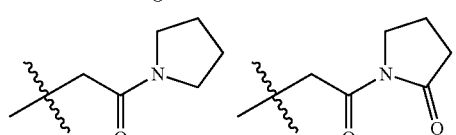

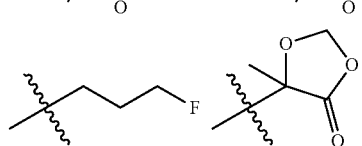

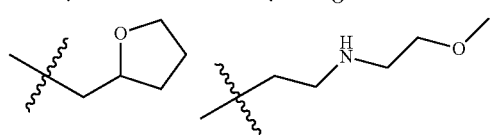

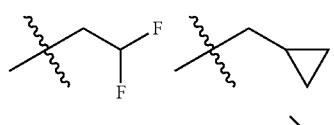

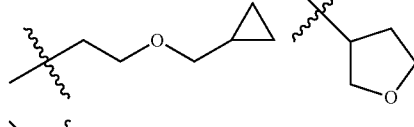

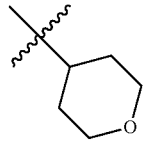

In one embodiment, X is $NHR_{1200}$.

In one embodiment, $R_{1100}$ is chosen from

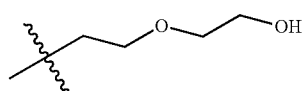

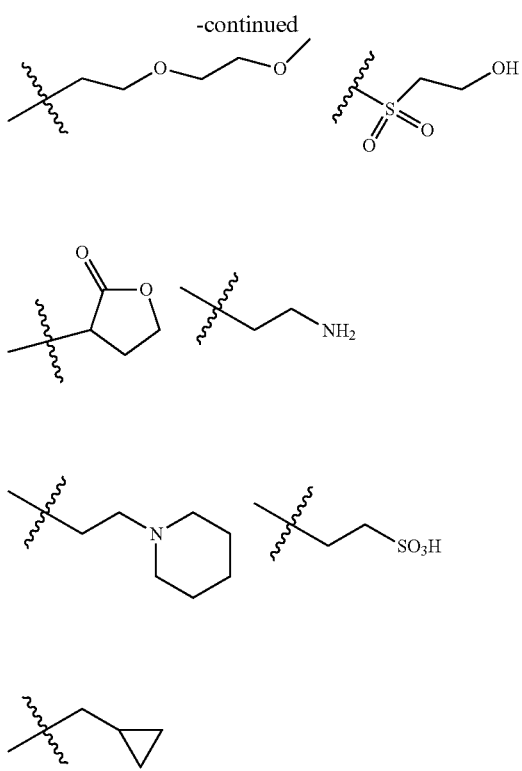

In one embodiment, X is O. In one embodiment, $R_{300}$, $R_{400}$, $R_{500}$, $R_{600}$, $R_{700}$ and $R_{800}$ are H. In one embodiment, $R_{1100}$ is alkyl.

Another embodiment from the priority provisional is a compound of Formula II(AA) represented by:

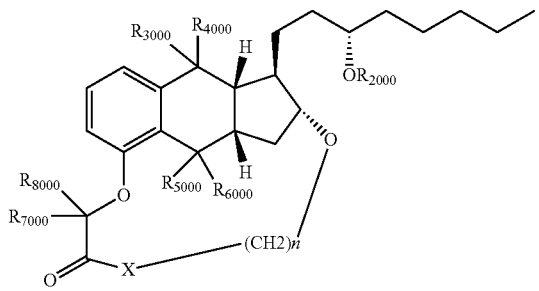

wherein, $R_{2000}$ is independently selected from the group consisting of H, $CONR_{9000}R_{10000}$, $CR_{9000}R_{10000}OCOPR_{9000}R_{10000}$. wherein, $R_{9000}$ and $R_{10000}$ are independently selected from H, alkyl, cycloalkyl.

$R_{3000}$, $R_{4000}$, $R_{5000}$, $R_{6000}$, $R_{7000}$ and $R_{8000}$ is independently selected from the group consisting of H, deuterium.

X is O, $NR_{12000}$, S

P is N, O $R_{12000}$ is haloalkyl, heteroalkyl, cycloheteroalkyl, alkylcycloalkyl, alkylcycloheteroalkyl, aryl, heteroaryl.

n is an integer between 1-7; and enantiomers of Formula II(AA), pharmaceutically acceptable salts of the compounds of Formula II(AA) and polymorphs of Formula II(AA).

Another embodiment from the priority provisional is a compound having Formula III(AA):

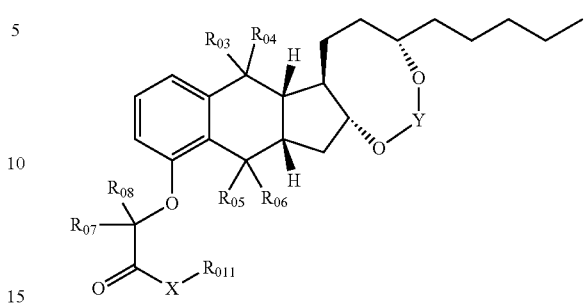

Wherein, $R_{11}$ is haloalkyl, heteroalkyl, cycloheteroalkyl, alkylcycloalkyl, alkylcycloheteroalkyl, aryl, heteroaryl.

wherein $R_{03}$, $R_{04}$, $R_{05}$, $R_{06}$, $R_{07}$ and $R_{08}$ is independently selected from the group consisting of H, deuterium.

wherein, X is O, $NR_{012}$, S $R_{012}$ is haloalkyl, heteroalkyl, cycloheteroalkyl, alkylcycloalkyl, alkylcycloheteroalkyl, aryl, heteroaryl.

Y is C=O, and enantiomers of the compound of formula III(AA); and pharmaceutically acceptable salts of the compounds of Formula III(AA) and polymorphs of Formula III(AA).

Methods of Making for Formula I Compounds

Organic synthesis is used to make the compounds. See, for example, *March's Advanced Organic Chemistry*, 6$^{th}$ Ed., Wiley, 2007.

The compounds of formula I where R1=R2=H can be synthesized according to scheme 1 by starting with the compound of formula I where Z is OH and R1 is H and R2 is PG which represents a protective group as described in *Protective Groups in Organic Synthesis* by Greene and Wuts. The carboxylic acid is activated using coupling conditions which involve the use of an activating agent, including but not limited to EDC, DCC, DIC, BOP, HATU, HBTU, CDI, thionyl chloride, or oxalyl chloride. Coupling conditions may also include or not include an additive, including but not limited to DMF, HOSu, HOBT, or HOAT, and may or may not include one or more nucleophilic or non-nucleophilic bases or additives including, but not limited to DMAP, TEA, DIPEA, N-methylmorpholine, pyridine, and/or imidazole. Coupling conditions also may be run in a suitable solvent or solvent mixture including, but not limited to DCM, THF, DMF, dioxane, ethyl acetate, acetonitrile. The activated acid can be isolated and purified or can be treated directly with ZH. Alternately, ZH can be present during the coupling conditions. Representative examples of coupling conditions and definitions of the activating agents, additives and bases can be found in in *Handbook of Reagents for Organic Synthesis: Activating Agents and Protecting Groups*, John Wiley and Sons. The resulting compound of formula I where Z is not OH, R1 is H and R2 is PG is deprotected using deprotection conditions suitable to the type of protective group represented by PG to give the compound of formula I. Examples of suitable deprotection conditions can be found in Protective Groups in Organic Synthesis by Greene and Wuts.

Scheme 1

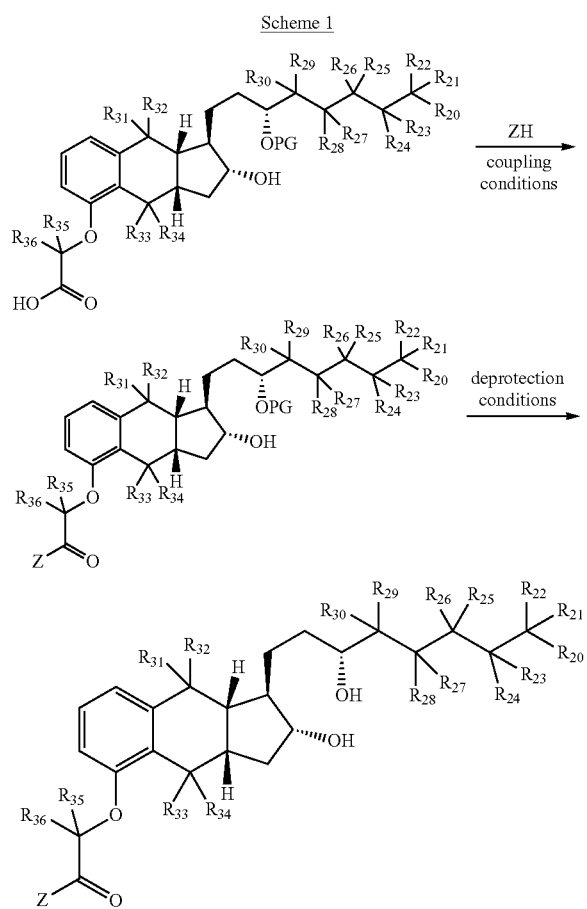

The compound of formula I where R1=R2 or where R1 is H can be synthesized according to scheme 2 starting from the compound of formula I where R1=R2=H by employing acylation conditions and the reactive molecule ROH or RY where Y is a leaving group including, but not limited to halogen, sulfonyl, phosphoryl, or acyl. In the case where the reactive molecule ROH is used, acylation conditions are identical to coupling conditions as described above. In the case where the reactive molecule RY is used, the acylation conditions may or may not include one or more nucleophilic or non-nucleophilic bases or additives including but not limited to DMAP, TEA, DIPEA, N-methylmorpholine, pyridine, and/or imidazole and may be run in a suitable solvent or solvent mixture including, but not limited to DCM, THF, DMF, dioxane, ethyl acetate, and acetonitrile.

Scheme 2

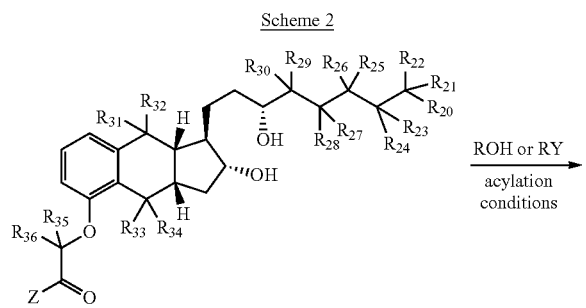

The compounds of formula I where R2 is H can be synthesized according to scheme 3 starting from the compound of formula I where R1 is H and R2 is PG as defined above, by employing acylation conditions using ROH or RY as defined above followed by deprotection conditions as defined above.

Scheme 3

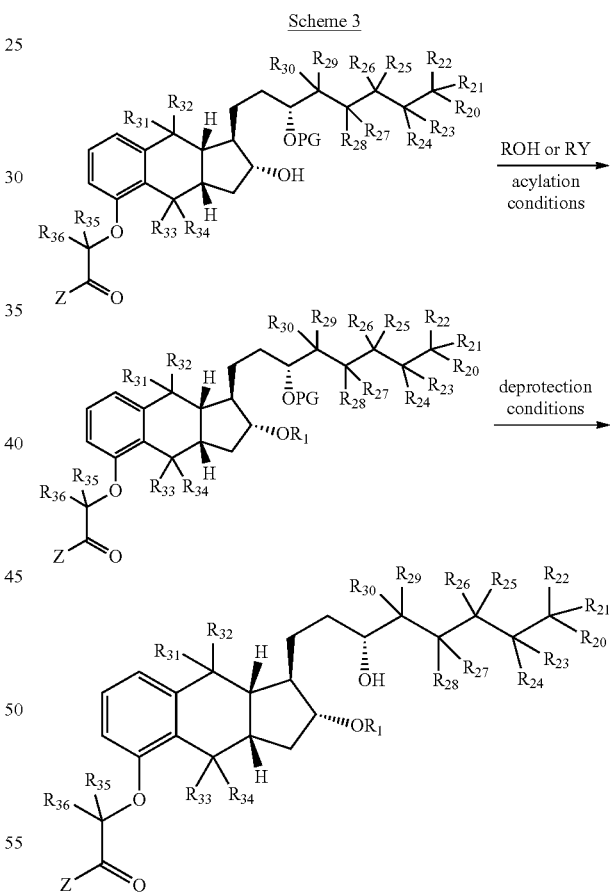

Method of Making Formula II Compounds

The compounds of scheme II can be synthesized according to Scheme 4 starting from the compound of scheme I where Z is OH and R2 is PG as defined above, by employing lactonization conditions. Examples of lactonization conditions can be found in *Chemical Reviews* (2007), 107, 239 and *Beilstein Journal of Organic Chemistry* (2012), 8, 1344, and include, but are not limited to 2,4,6-trichlorobenzoic anhydride, TEA and DMAP; 4-nitrobenzoic anhydride, TEA, and DMAP; 2-chloro-1-methylpyridinium iodide and tributyl amine; 2,2'-dipyridyl disulfide and triphenylphosphine; and the all the reactions in the coupling conditions and acylation conditions described above. The lactonization reactions may be run in a suitable solvent or solvent mixture including, but not limited to DCM, THF, DMF, dioxane, ethyl acetate, acetonitrile and toluene.

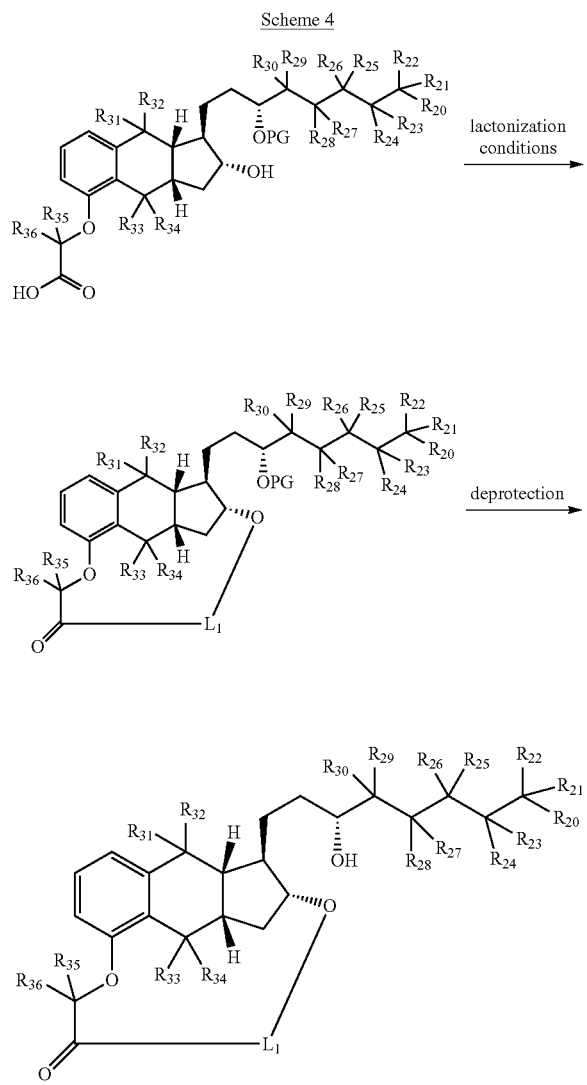

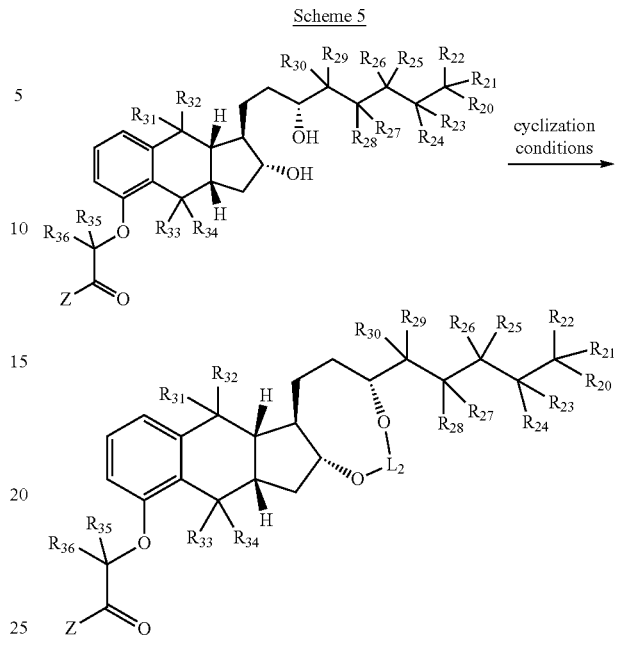

Method of Making Formula III Compounds

The compounds of formula III can be synthesized according to Scheme 5 starting with the compound of formula 1 where R1=R2=H, by reacting with an activated carbonyl equivalent including but not limited to phosgene, carbonyl diimidazole, or 4-nitrophenyl chloroformate, in the presence or absence of one or more nucleophilic or non-nucleophilic bases or additives including but not limited to DMAP, TEA, DIPEA, N-methylmorpholine, pyridine, and/or imidazole and may be run in a suitable solvent or solvent mixture including, but not limited to DCM, THF, DMF, dioxane, ethyl acetate, acetonitrile, and toluene.

Compositions

The compounds described herein can be used alone or in combination with other components as known in the art. In particular, formulations of multiple ingredients can be prepared that are adapted for use in prophylactic and therapeutic treatments. The composition can be in the form of, for example, a solid, liquid, semi-solid, solution, suspension, or emulsion formulation. Water can be used as a formulation agent. It can be in pure form or combined with one or more excipients.

In one embodiment, the compound is formulated in matrix form, comprising a matrix material in which drug is contained or dispersed. The matrix material further controls release of the drug by controlling dissolution and/or diffusion of the drug from the reservoir, and may enhance stability of the drug molecule while stored in the reservoir. In one embodiment, the drug is formulated with an excipient material that is useful for accelerating release, e.g., a water-swellable material that can aid in pushing the drug out of the reservoir and through any tissue capsule over the reservoir. Examples include hydrogels and osmotic pressure generating agents known in the art. In another embodiment, the drug is formulated with a penetration enhancer(s). The penetration enhancer further controls release of the drug by facilitating transport of the drug across the skin into the local administration site or systemic delivery.

More particularly, the drug can be dispersed in a matrix material, to further control the rate of release of drug. This matrix material can be a "release system," as described in U.S. Pat. No. 5,797,898, the degradation, dissolution, or diffusion properties of which can provide a method for controlling the release rate of the chemical molecules.

The release system may provide a temporally modulated release profile (e.g., pulsatile release) when time variation in plasma levels is desired or a more continuous or consistent release profile when a constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e., pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release). The active release systems described herein can be used alone or on combination with passive release systems, for example, as described in U.S. Pat. No. 5,797,898.

The pharmaceutical agent can be formulated with one or more pharmaceutically acceptable excipients. Representative examples include bulking agents, wetting agents, stabilizers, crystal growth inhibitors, antioxidants, antimicrobials, preservatives, buffering agents (e.g., acids, bases), surfactants, desiccants, dispersants, osmotic agents, binders (e.g., starch, gelatin), disintegrants (e.g., celluloses), glidants (e.g., talc), diluents (e.g., lactose, dicalcium phosphate), color agents, lubricants (e.g., magnesium stearate, hydrogenated vegetable oils) and combinations thereof. In some embodiments, the excipient is a wax or a polymer. In one embodiment, the polymer comprises polyethylene glycol (PEG), e.g., typically one having a molecular weight between about 100 and 10,000 Daltons (e.g., PEG 200, PEG 1450). In another embodiment, the polymer comprises poly lactic acid (PLA), poly glycolic acid (PGA), copolymers thereof (PLGA), or ethyl-vinyl acetate (EVA) polymers. In yet another embodiment, the excipient material comprises a pharmaceutically acceptable oil (e.g., sesame oil).

In one embodiment, the excipient material includes a saturated drug solution. That is, the excipient material comprises a liquid solution formed of the drug dissolved in a solvent for the drug. The solution is saturated so that the solvent does not dissolve the solid matrix form of the drug. The saturated solution acts as a non-solvent excipient material, substantially filling pores and voids in the solid matrix.

In another embodiment, the excipient material comprises a pharmaceutically-acceptable perhalohydrocarbon or unsubstituted saturated hydrocarbon. See, for example, U.S. Pat. No. 6,264,990 to Knepp et al., which describes anhydrous, aprotic, hydrophobic, non-polar liquids, such as biocompatible perhalohydrocarbons or unsubstituted saturated hydrocarbons, such as perfluorodecalin, perflurobutylamine, perfluorotripropylamine, perfluoro-N-methyldecahydroquindine, perfluoro-octohydro quinolidine, perfluoro-N-cyclohexylpyrilidine, perfluoro-N,N-dimethylcyclohexyl methylamine, perfluoro-dimethyl-adamantane, perfluorotrimethylbicyclo (3.3.1) nonane, bis(perfluorohexyl) ethene, bis(perfluorobutyl) ethene, perfluoro-1-butyl-2-hexyl ethene, tetradecane, methoxyflurane and mineral oil).

In one embodiment, the pharmaceutically acceptable excipient material comprises dimethyl sulfoxide (DMSO), glycerol, or ethanol.

Mixtures of compounds according to Formulae I, II, III, and IV can be used.

EXAMPLES

Additional embodiments are provided in the following, non-limiting examples.

Four assays on compounds were carried out by the following methods with the results shown in Table I:

(Test 1) Human liver microsomal stability assay was conducted by incubating 0.5 uM test compounds at 37° C. for up to 45 minutes in 50 mM of potassium phosphate buffer (pH 7.4) containing 0.5 mg of microsomal protein and 50 μL of NADPH generating system (7.8 mg of glucose 6-phosphate, 1.7 mg of NADPH and 6 U of glucose 6-phosphate dehydrogenase) per mL in 2% w/v of sodium bicarbonate). At 0, 5, 15, 30 and 45 min., an aliquot was taken, quenched with internal standard containing stop solution. No co-factor controls at 45 minutes were also prepared. After incubation, the samples were analyzed by LC-MS/MS. Peak area ratios of analyte to internal standard were used to calculate the intrinsic clearance. The intrinsic clearance (CLint) was determined from the first order elimination constant by non-linear regression. Formation of the active drug Compound A over the time course was also monitored by LCMS/MS analysis.

(Test 2) Human plasma stability assay was conducted by incubating 0.5 uM test compounds at 37° C. for up to 120 minutes in heparinated human plasma. At 0, 5, 15, 30, 60 and 120 min., an aliquot was taken, quenched with internal standard containing stop solution. After incubation, the samples were analyzed by LC-MS/MS. Peak area ratios of analyte to internal standard were used to calculate the half-life. Formation of the active drug Compound A over the time course was also monitored by LCMS/MS analysis.

(Test 3) Human skin homogenate stability assay was conducted, in the same way as in human liver microsomal stability assay, by incubating 0.5 uM test compounds at 37° C. for up to 45 minutes in 50 mM of potassium phosphate buffer (pH 7.4) containing 0.5 mg of human skin homogenate protein and 50 μL of NADPH generating system (7.8 mg of glucose 6-phosphate, 1.7 mg of NADPH and 6 U of glucose 6-phosphate dehydrogenase) per mL in 2% w/v of sodium bicarbonate). At 0, 5, 15, 30 and 45 min., an aliquot was taken, quenched with internal standard containing stop solution. No co-factor controls at 45 minutes were also prepared. After incubation, the samples were analyzed by LC-MS/MS. Peak area ratios of analyte to internal standard were used to calculate the intrinsic clearance. The intrinsic clearance (CLint) was determined from the first order elimination constant by non-linear regression. Formation of the active drug Compound A over the time course was also monitored by LCMS/MS analysis.

(Test 4) Human hepatocyte stability assay was conducted by incubating 0.5 uM test compound at 37° C. for up to 240 minutes. Cryopreserved human hepatocytes were obtained from Celsis IVT (Baltimore Md.). Cells were thawed according to vendor's instructions and were suspended in William's Medium E to 0.5 million cells/mL. Test compounds were spiked into the cell suspension to initiate the reactions. At 0, 10, 30, 60, 120 and 240 min., an aliquot was taken, quenched with internal standard containing stop solution. After incubation, the samples were analyzed by LC-MS/MS. Peak area ratios of analyte to internal standard were used to calculate the intrinsic clearance. The intrinsic clearance (CLint) was determined from the first order elimination constant by non-linear regression. Formation of the active drug Compound A over the time course was also monitored by LCMS/MS analysis.

Assay results (half life) are shown in Table I. In Table I, the code for the results of the assay testing are:
A=<15 min
B=15-30 min
C=31-60 min
D=>60 min

TABLE I

| Compound No. | MW (g/mol) | m/z [M + Na]+ | Test 1 T₁/₂ | Test 2 T₁/₂ | Test 3 T₁/₂ | Test 4 T₁/₂ |
|---|---|---|---|---|---|---|
| 1 | 444.62 | 467.62 | A | A | | |
| 2 | 443.63 | 466.63 | A | D | | C |
| 3 | 503.68 | 526.68 | | | | |
| 4 | 450.6 | 473.6 | A | A | | |
| 5 | 460.62 | 483.62 | A | A | | |
| 6 | 476.62 | 499.62 | A | A | | |
| A | 390 | 413 | | | | |
| 7 | 433.59 | 456.59 | A | D | | B |
| 8 | 432.61 | 455.61 | A | | | |
| 9 | 434 | 457 | A | | | |
| 10 | 448 | 471 | A | | | |
| 11 | 447 | 470 | A | D | | |
| 12 | 461 | 484 | A | D | | |
| 13 | 475 | 498 | A | D | | A |
| 14 | 471 | 494 | A | D | D | A |
| 57 | 372 | 395 | D | D | | D |
| 15 | 404 | 427 | A | A | A | |
| 16 | 460 | 483 | A | B | A | |
| 17 | 460 | 483 | A | C | A | |
| 18 | 474 | 497 | A | D | D | |
| 19 | 484 | 507 | A | C | A | |
| 20 | 432 | 455 | A | C | A | |
| 21 | 521 | 544 | A | D | | |
| 22 | 488 | 511 | A | D | D | |
| 23 | 488 | 511 | A | D | | |
| 24 | 472 | 495 | A | D | | |
| 25 | 476 | 499 | A | D | C | |
| 26 | 446 | 489 | A | C | B | |
| 27 | 532 | 555 | A | D | | |
| 28 | 446 | 469 | A | C | | |

Examples for Synthesis

In addition, the following representative syntheses are shown for compounds according to Formulae I, II, and III.

Example 1: Synthesis of: 2-[2-Hydroxy-1-(3-hydroxy-octyl)-2,3,3a,4,9,9a-hexahydro-1H-cyclopenta[b]naphthalen-5-yloxy]-N-(2,2,2-trifluoro-ethyl)-acetamide

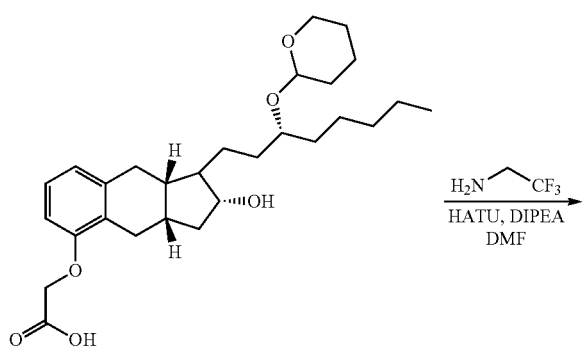

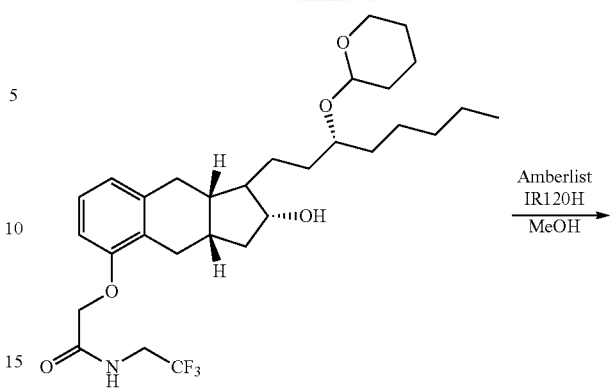

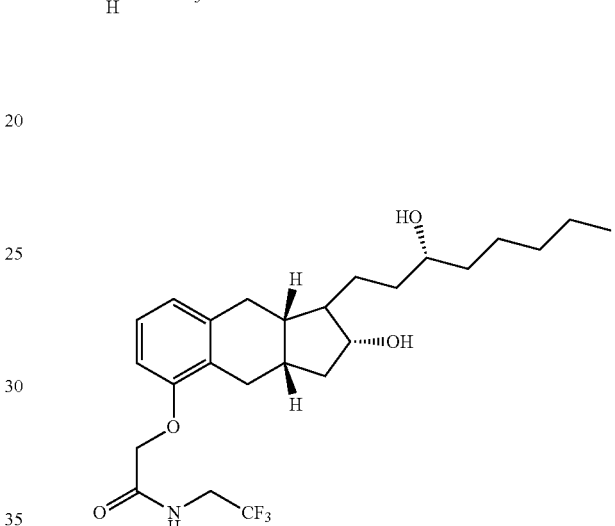

A solution of {2-Hydroxy-1-[3-(tetrahydro-pyran-2-yloxy)-octyl]-2,3,3a,4,9,9a-hexahydro-1H-cyclopenta[b]naphthalen-5-yloxy}-acetic acid (94 mg, 0.2 mmol), trifluoroethylamine (54 mg, 0.6 mmol) and DIPEA (104 μl, 0.6 mmol) in DMF (2 ml) was treated with HATU and stirred 24 hr at RT. The reaction mixture was diluted with MTBE and washed with saturated sodium bicarbonate solution and brine, dried over sodium sulfate and concentrated under vacuum. The residue was purified by silica gel chromatography. This resulting material was dissolved in MeOH (4 ml), treated with Amberlite IR120H and stirred 24 hr. The reaction mixture was filtered and concentrated to yield 2-[2-hydroxy-1-(3-hydroxy-octyl)-2,3,3a,4,9,9a-hexahydro-1H-cyclopenta[b]naphthalen-5-yloxy]-N-(2,2,2-trifluoro-ethyl)-acetamide (46 mg) as an oil. $^1$HNMR (400 MHz, CDCl$_3$) δ 7.06 (d, 1H, J=7.6); 6.80 (d, 1H, J=7.2); 6.63 (d, 1H, J=8.0); 4.86 (quint., 1H, J=6.4); 4.60 (s, 2H); 3.7-3.8 (m, 1H); 3.55-3.65 (m, 1H); 2.85-2.95 (ddd, 1H); 2.70-2.80 (dd, 1H); 2.50-2.60 (ddd, 1H); 2.40-2.50 (dd, 1H); 2.15-2.3 (m, 2H); 1.75-1.95 (m, 2H); 1.24-1.70 (m, 17H); 1.20 (d, 3H, J=6.4); 0.85-0.95 (m, 8H); MS: m/z 494 [M+Na]$^+$ Example 2: Synthesis of: [2-Hydroxy-1-(3-hydroxy-octyl)-2,3,3a,4,9,9a-hexahydro-1H-cyclopenta[b]naphthalen-5-yloxy]-acetic Acid 1,2-dimethyl-propyl Ester Example 3: Synthesis of: treprostinil 2-hydroxy lactone

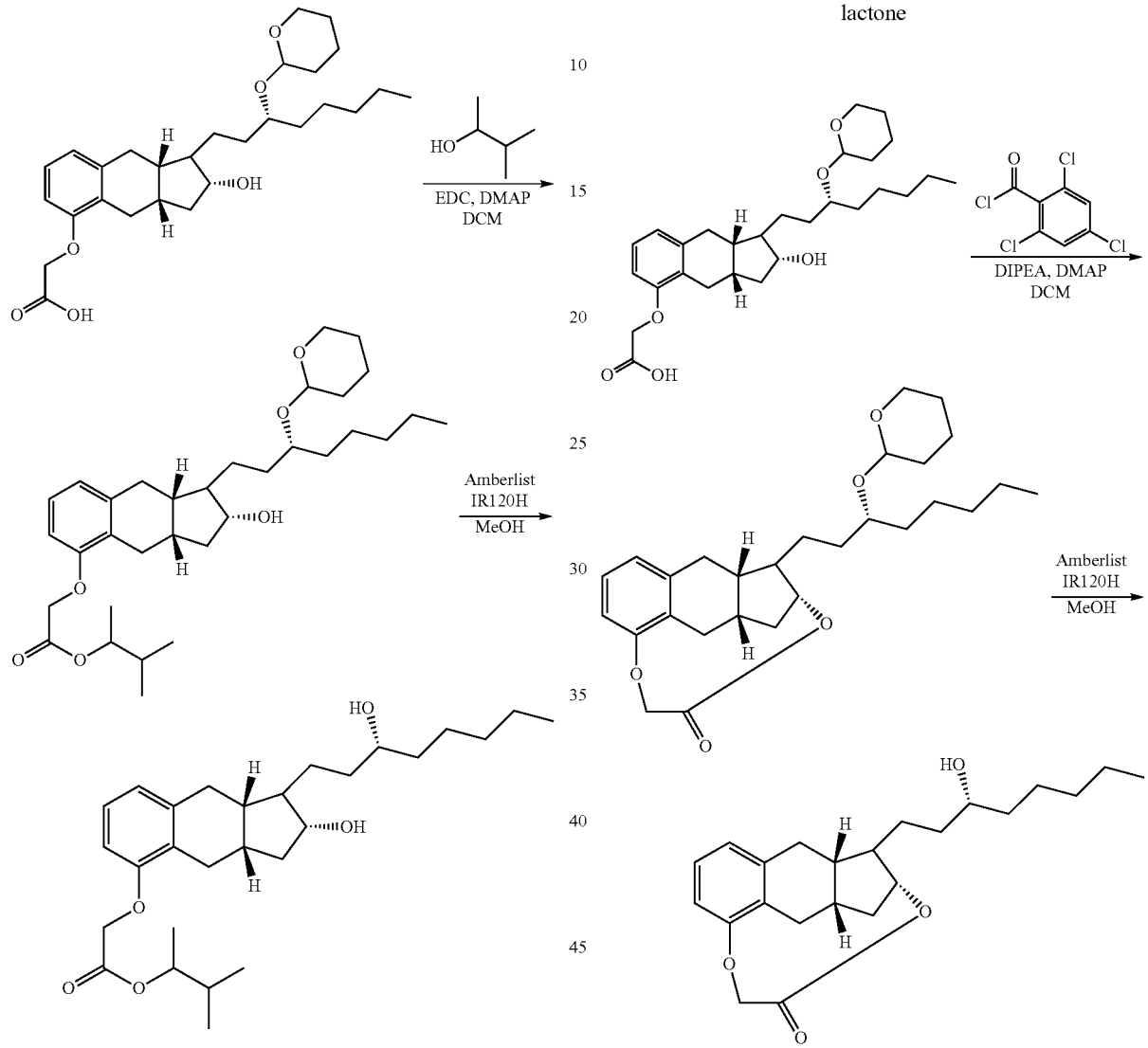

A solution of {2-Hydroxy-1-[3-(tetrahydro-pyran-2-yloxy)-octyl]-2,3,3a,4,9,9a-hexahydro-1H-cyclopenta[b]naphthalen-5-yloxy}-acetic acid (47 mg, 0.1 mmol), 3-methyl-2-butanol (26 mg, 0.3 mmol) and DMAP (12 mg, 0.1 mmol) in DCM (1 ml) was treated with EDC (26 mg, 0.14 mmol) and stirred 24 hr at RT. The reaction mixture was diluted with MTBE and washed with saturated sodium bicarbonate solution and brine, dried over sodium sulfate and concentrated under vacuum. The residue was purified by silica gel chromatography. This resulting material was dissolved in MeOH/THF (4 ml), treated with Amberlite IR120H and stirred 24 hr. The reaction mixture was filtered and concentrated to yield [2-hydroxy-1-(3-hydroxy-octyl)-2,3,3a,4,9,9a-hexahydro-1H-cyclopenta[b]naphthalen-5-yloxy]-acetic acid 1,2-dimethyl-propyl ester (16 mg) as an oil. $^1$HNMR (400 MHz, CDCl$_3$) δ 7.06 (d, 1H, J=7.6); 6.80 (d, 1H, J=7.2); 6.63 (d, 1H, J=8.0); 4.86 (quint., 1H, J=5.6); 4.60 (s, 2H); 3.7-3.8 (m, 1H); 3.55-3.80 (m, 1H); 3.55-3.70 (m, 1H); 2.85-2.95 (dd, 1H); 2.50-2.80 (dd, 1H); 2.50-2.60 (dd, 1H); 2.40-2.60 (dd, 1H); 2.15-2.30 (m, 2H); 1.75-1.95 (m, 2H); 1.35-1.80 (m, 17H); 1.19 (d, 3H, J=6.4); 0.85-0.95 (m, 8H); MS: m/z 483 [M+Na]$^+$ A solution of {2-Hydroxy-1-[3-(tetrahydro-pyran-2-yloxy)-octyl]-2,3,3a,4,9,9a-hexahydro-1H-cyclopenta[b]naphthalen-5-yloxy}-acetic acid (47 mg, 0.1 mmol) and DMAP (26 mg, 0.2 mmol) in DCM (1 ml) was treated with 2,4,6-trichlorobenzoyl chloride (27 mg, 0.11 mmol) and stirred 24 hr at RT. The reaction mixture was diluted with ethyl acetate and washed with saturated sodium bicarbonate solution and brine, dried over sodium sulfate and concentrated under vacuum. The residue was purified by silica gel chromatography. This resulting material was dissolved in MeOH/THF (4 ml), treated with Amberlite IR120H and stirred 24 hr. The reaction mixture was filtered and concentrated to yield treprostinil 2-hydroxy lactone (8 mg) as an oil. $^1$HNMR (400 MHz, CDCl$_3$) δ 7.03 (dd, 1H, J=8.4 Hz, J=7.6 Hz); 6.74 (d, 1H, J=7.6 Hz); 6.55 (d, 1H, J=8.4 Hz) 4.53 (m, 1H); 4.46 (d, 1H, J=15.2 Hz); 4.31 (d, 1H, J=15.2 Hz); 3.53 (m, 1H); 2.5 (m, 1H); 2.8 (dd, 1H); 2.6 (dd, 1H);

2.2-2.55 (m, 4H); 1.53 (m, 4H); 1.35-1.47 (m, 4H); 1.3 (m, 6H); 0.89 (m, 3H); MS: m/z 395 [M+Na]+

Example 4: Synthesis of: Cyclopropanecarboxylic Acid 1-(3-hydroxy-octyl)-5-methoxycarbonyl-methoxy-2,3,3a,4,9,9a-hexahydro-1H-cyclopenta[b]naphthalen-2-yl Ester

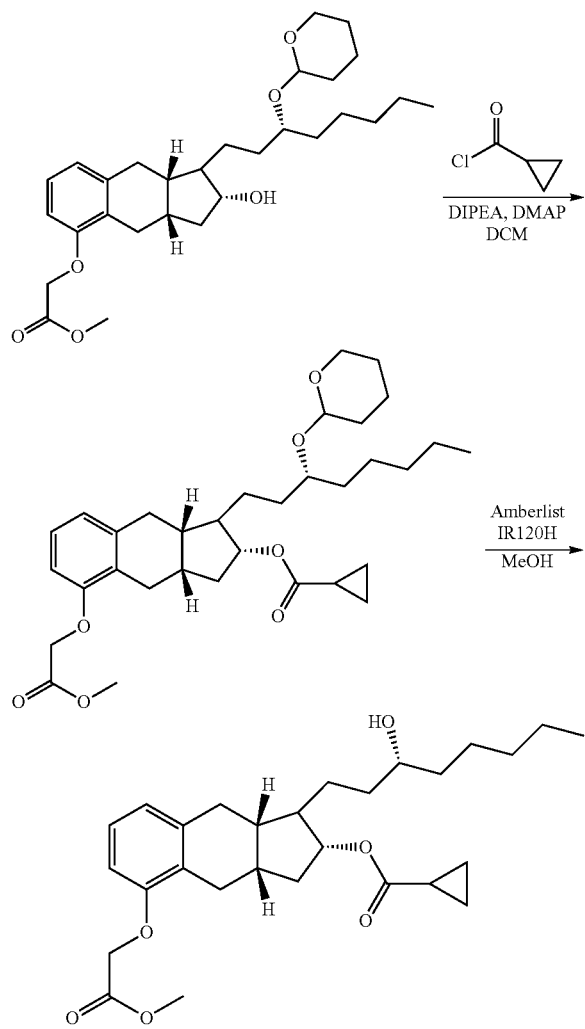

A solution of [2-Hydroxy-1-(3-hydroxy-octyl)-2,3,3a,4,9,9a-hexahydro-1H-cyclopenta[b]naphthalen-5-yloxy]-acetic acid methyl ester (32 mg, 0.06 mmol), DIPEA (31 µl, 0.18 mmol) and DMAP (1 crystal) in DCM (2 ml) was treated with cyclopropanecarbonyl chloride (8 µl, 0.08 mmol) and stirred for 24 hr at RT under nitrogen. The reaction mixture was diluted with MTBE and washed with saturated sodium bicarbonate solution and brine, dried over sodium sulfate and concentrated under vacuum. The residue was purified by silica gel chromatography. This resulting material was dissolved in MeOH/THF (4 ml), treated with Amberlite IR120H and stirred 24 hr. The reaction mixture was filtered and concentrated to yield cyclopropanecarboxylic acid 1-(3-hydroxy-octyl)-5-methoxycarbonylmethoxy-2,3,3a,4,9,9a-hexahydro-1H-cyclopenta[b]naphthalen-2-yl ester (32 mg) as an oil. $^1$HNMR: (400 MHz, DMSO-d$_6$) δ 7.06 (d, 1H, J=7.6); 6.80 (d, 1H, J=7.2); 6.63 (d, 1H, J=8.8); 4.78 (s, 2H); 4.1-4.2 (m, 1H); 4.05-4.50 (m, 1H); 3.68 (s, 3H); 2.6-2.8 (m, 2H); 2.4-2.5 (m, 2H); 2.20-2.35 (m, 1H); 2.10-2.20 (m, 1H); 1.8-1.95 (m, 1H); 1.10-1.16 (m, 15H); 0.95-1.10 (m, 1H); 0.70-0.90 (m, 7H); MS: m/z 495 [M+Na]+

Example 5: Synthesis of Formula III Compound

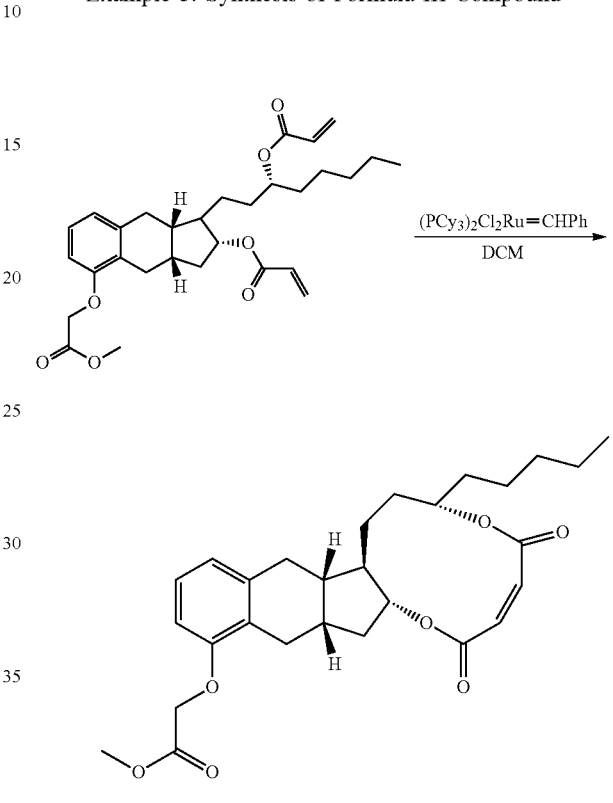

A solution of acrylic acid 1-[2-(2-acryloyloxy-5-methoxycarbonylmethoxy-2,3,3a,4,9,9a-hexahydro-1H-cyclopenta[b]naphthalen-1-yl)-ethyl]-hexyl ester (51 mg, 0.1 mmol) in chloroform (20 ml) is treated with a solution of (PCy3)2Cl2Ru=CHPh (19 mg, 0.023 mmol) in chloroform (3 ml) and stirred 24 hr at RT. TEA (1 ml) is added and the solution is concentrated under vacuum. The residue is purified by silica gel chromatography to yield the title compound.

Additional synthetic schemes are shown below:

Example 6 (Formula I Compound)

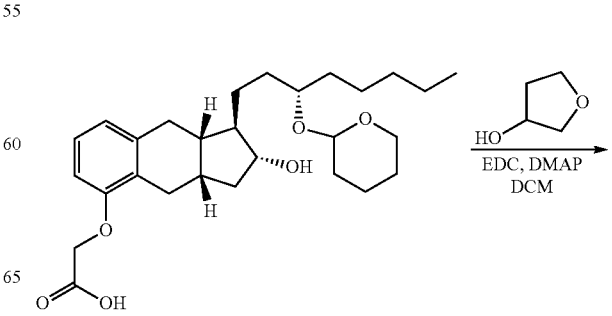

-continued

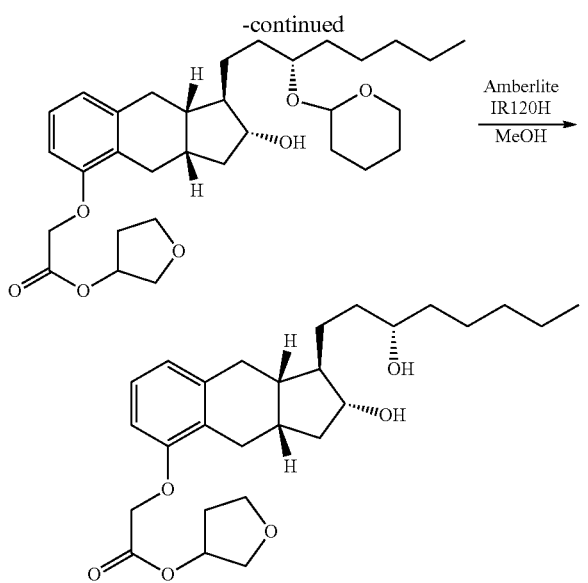

Example 7 (Formula I Compound)

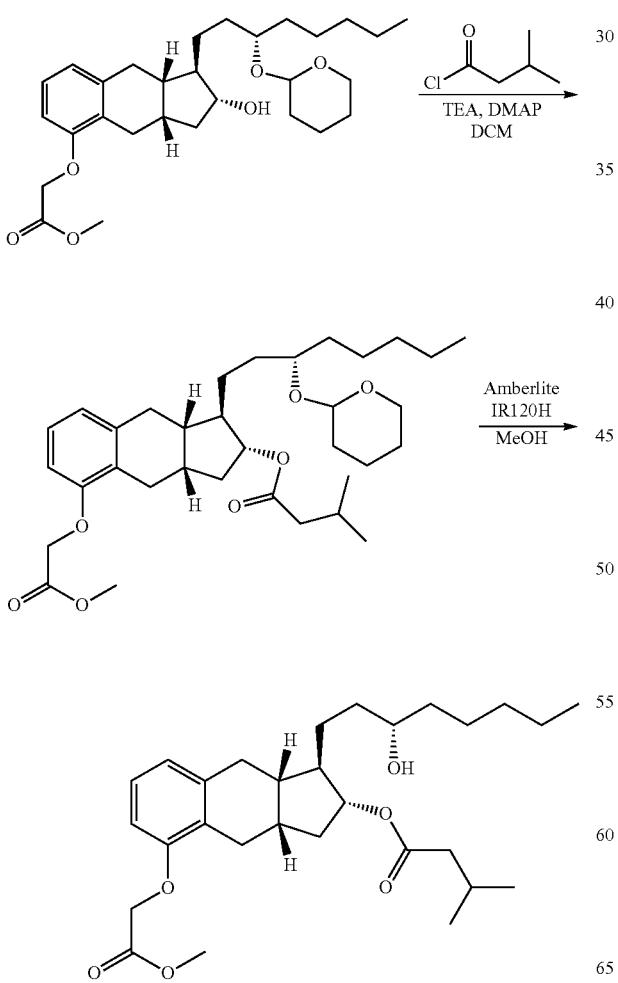

What is claimed is:
1. A compound represented by Formula (I):

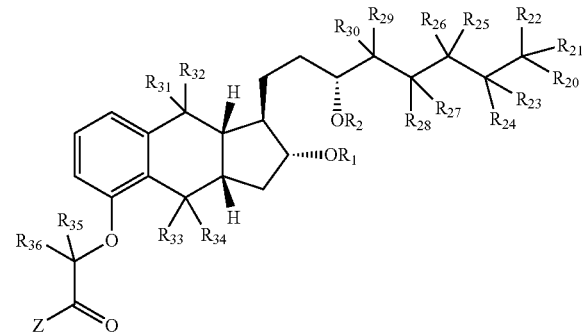

wherein:
$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$ are independently H or deuterium;

Z is —OH, —$OR_{11}$, —N($R_{11}$)$R_{12}$, —$SR_{11}$ or $P_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from the group consisting of:

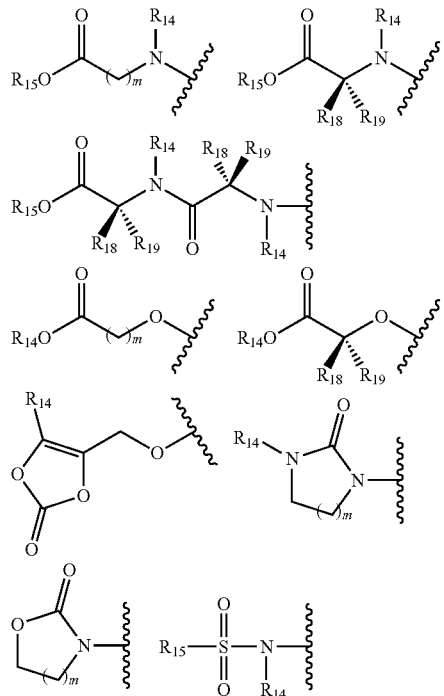

wherein:
m is 1, 2, 3 or 4;
$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl; or $R_{14}$ and $R_{15}$ taken together with the atoms to which they are attached optionally form a 5- to 7-membered ring incorporating two ring heteroatoms chosen from N, O and S, which is unsubstituted or substituted with 1, 2 or 3 substituents independently selected from the group consisting of halo, methyl and methoxy;

$R_{18}$ and $R_{19}$ are independently in each occurrence hydrogen or alkyl, wherein the alkyl is unsubstituted or substituted with 1 substituent selected from the group consisting of halo, hydroxy, alkoxy, amino, thio, methylthio, —C(O)OH, —C(O)O-(alkyl), —CONH$_2$, aryl and heteroaryl, wherein the aryl or heteroaryl is unsubstituted or substituted with a substituent selected from the group consisting of alkyl, halo, haloalkyl, hydroxy, alkoxy, and haloalkoxy;

$R_{14}$ and $R_{18}$ taken together with the atoms to which they are attached optionally form a 5- to 7-membered ring;

$R_{14}$ and $R_{19}$ taken together with the atoms to which they are attached optionally form a 5- to 7-membered ring;

$R_{15}$ and $R_{18}$ taken together with the atoms to which they are attached optionally form a 5- to 7-membered ring; and $R_{15}$ and $R_{19}$ taken together with the atoms to which they are attached optionally form a 5- to 7-membered ring; and $R_1$ and $R_2$ are independently H or $P_2$, wherein at least one of $R_1$ and $R_2$ is $P_2$, wherein $P_2$ is selected from the group consisting of:

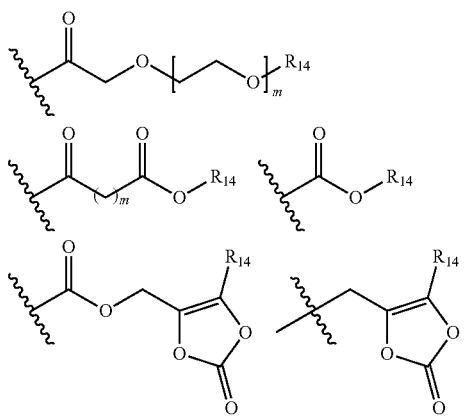

wherein:
m is 1, 2, 3 or 4; and
$R_{14}$ is independently in each occurrence alkyl or substituted alkyl;

or an enantiomer, a pharmaceutically acceptable salt or a polymorph thereof.

2. The compound of claim 1, wherein $R_1$ is $P_2$ and $R_2$ is H.
3. The compound of claim 1, wherein $R_1$ is H and $R_2$ is $P_2$.
4. The compound of claim 1, wherein $R_1$ is $P_2$ and $R_2$ is $P_2$.
5. The compound of claim 1, wherein each of $R_{20}$ to $R_{36}$ is H.
6. The compound of claim 1, wherein at least one of $R_{20}$ to $R_{36}$ is deuterium.

7. The compound of claim 1, wherein Z is —OR$_{11}$.
8. The compound of claim 1, wherein Z is $P_1$.
9. The compound of claim 1, wherein Z is —N(R$_{11}$)R$_{12}$.
10. The compound of claim 1, wherein Z is —OH.
11. The compound of claim 1, which is represented by Formula (IA):

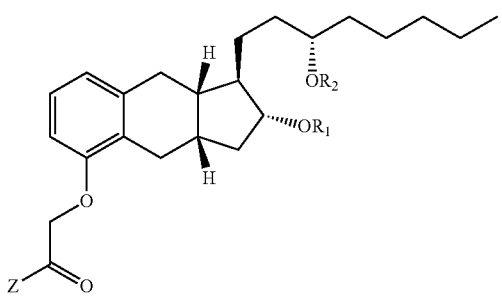

wherein:
Z is —OH, —OR$_{11}$ or $P_1$;
$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, or substituted alkylcycloheteroalkyl;
$P_1$ is selected from the group consisting of:

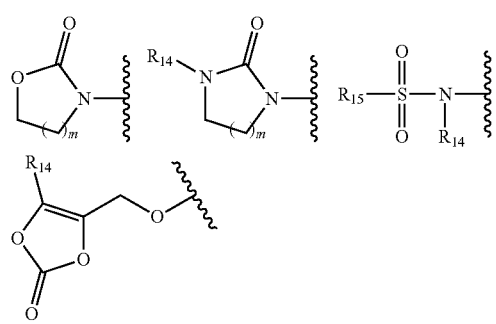

wherein:
m is 1, 2, 3 or 4;
$R_{14}$ and $R_{15}$ are independently selected from the group consisting of H, alkyl, cycloalkyl, alkylcycloalkyl, haloalkyl, aryl, heteroaryl, arylalkyl, heteroarylalkyl, substituted aryl, substituted heteroaryl, substituted arylalkyl, and substituted heteroarylalkyl; or
$R_{14}$ and $R_{15}$ taken together with the atoms to which they are attached optionally form a 5- to 7-membered ring; and
$R_1$ and $R_2$ are independently H or $P_2$, wherein at least one of $R_1$ and $R_2$ is $P_2$,
wherein $P_2$ is selected from the group consisting of:

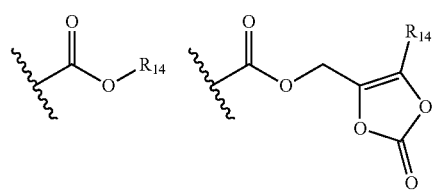

-continued

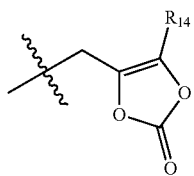

wherein $R_{14}$ is alkyl;
or an enantiomer, a pharmaceutically acceptable salt or a polymorph thereof.

12. A composition comprising a compound of claim 1 or a pharmaceutically acceptable salt thereof and one or more pharmaceutically acceptable excipients.

13. The composition of claim 12, which is formulated for transdermal delivery.

14. The composition of claim 13, which is formulated for transdermal delivery with a patch.

15. The composition of claim 12, further comprising at least one solvent.

16. A method of treating pulmonary hypertension, comprising administering to a subject in need of treatment a therapeutically effective amount of a compound of claim 1 or a pharmaceutically acceptable salt thereof.

17. The method of claim 16, wherein the pulmonary hypertension is pulmonary arterial hypertension.

18. The method of claim 16, wherein the compound is administered transdermally.

19. The method of claim 18, wherein the compound is administered via a transdermal patch.

* * * * *